United States Patent
Smith et al.

(10) Patent No.: US 10,112,960 B2
(45) Date of Patent: Oct. 30, 2018

(54) METHODS FOR PRODUCING BORYLATED ARENES

(71) Applicants: Dow AgroSciences, LLC, Indianapolis, IN (US); Board of Trustees of Michigan State University, East Lansing, MI (US)

(72) Inventors: Milton R. Smith, East Lansing, MI (US); Robert E. Maleczka, Dewitt, MI (US); Hao Li, East Lansing, MI (US); Chathurika R. K. Jayasundara, East Lansing, MI (US); Jossian Oppenheimer, Midland, MI (US); Dmitrijs Sabasovs, Haslett, MI (US)

(73) Assignees: Dow AgroSciences LLC, Indianapolis, IN (US); The Board of Regents of the Michigan State University, Ann Arbor, MI (US)

( * ) Notice: Subject to any disclaimer, the term of this patent is extended or adjusted under 35 U.S.C. 154(b) by 480 days.

(21) Appl. No.: 14/478,581

(22) Filed: Sep. 5, 2014

(65) Prior Publication Data
US 2015/0065743 A1 Mar. 5, 2015

Related U.S. Application Data

(60) Provisional application No. 61/874,249, filed on Sep. 5, 2013, provisional application No. 62/012,684, filed on Jun. 16, 2014.

(51) Int. Cl.
*C07F 5/02* (2006.01)
*C07F 15/04* (2006.01)
*C07C 67/343* (2006.01)
*C07C 253/30* (2006.01)

(52) U.S. Cl.
CPC ............ *C07F 5/025* (2013.01); *C07C 67/343* (2013.01); *C07C 253/30* (2013.01); *C07F 15/04* (2013.01)

(58) Field of Classification Search
CPC .................................. C07F 5/025; C07F 15/04
See application file for complete search history.

(56) References Cited

U.S. PATENT DOCUMENTS

| | | |
|---|---|---|
| 6,867,302 B2 | 3/2005 | Smith et al. |
| 6,878,830 B2 | 4/2005 | Smith |
| 6,969,716 B2 | 11/2005 | Blackaby et al. |
| 7,314,849 B2 | 1/2008 | Balko et al. |
| 7,514,563 B2 | 4/2009 | Smith et al. |
| 7,611,647 B2 | 11/2009 | Arndt et al. |
| 7,915,200 B2 | 3/2011 | Epp et al. |
| 8,426,591 B2 | 4/2013 | Guenthenspberger et al. |
| 2004/0192692 A1 | 9/2004 | Blackaby et al. |
| 2006/0281939 A1* | 12/2006 | Smith, III ............ C07D 207/34 558/384 |
| 2009/0088322 A1 | 4/2009 | Epp et al. |
| 2009/0182168 A1* | 7/2009 | Arndt .................. C07F 1/02 562/474 |
| 2010/0292227 A1 | 11/2010 | Yoakim et al. |
| 2011/0086759 A1 | 4/2011 | Aspinall et al. |
| 2012/0040936 A1 | 2/2012 | Kanno et al. |
| 2012/0115724 A1 | 5/2012 | Whittingham et al. |
| 2012/0190549 A1 | 7/2012 | Eckelbarger et al. |
| 2012/0190551 A1 | 7/2012 | Yerkes et al. |
| 2013/0005574 A1 | 1/2013 | Epp et al. |
| 2013/0172566 A1 | 7/2013 | Oppenheimer et al. |
| 2013/0172567 A1 | 7/2013 | Oppenheimer et al. |

FOREIGN PATENT DOCUMENTS

| | | |
|---|---|---|
| GB | 2484982 | 5/2012 |
| WO | 2001064689 A1 | 9/2001 |
| WO | 2007/082098 | 7/2007 |
| WO | 2009/023438 | 2/2009 |
| WO | 2009/029735 | 3/2009 |
| WO | 2009/081112 | 7/2009 |
| WO | 2010/125332 | 11/2010 |
| WO | 2010/149956 | 12/2010 |
| WO | 2011/073845 | 6/2011 |
| WO | 2011/075613 | 6/2011 |
| WO | 2011/103546 | 8/2011 |
| WO | 2012/033735 | 3/2012 |
| WO | 2010/116915 | 10/2012 |
| WO | 2013/003740 | 1/2013 |
| WO | 2013016557 A2 | 1/2013 |
| WO | 2013/101665 | 7/2013 |

OTHER PUBLICATIONS

Rahaim et al. "Room temperature dehalogenation of chloroarenes by polymethylhydrosiloxane (PMHS) under palladium catalysis" Tetrahedron Letters, 2002, vol. 43, pp. 8823-8826.*
Tagata et al. "Development of recyclable iridium catalyst for C—H borylation" Tetrahedron Letters, 2009, vol. 50, pp. 6176-6179.*
Kikuchi et al. "Iridium-catalyzed Vinylic C—H Borylation of Cyclic Vinyl Ethers by Bis(pinacolato)diboron" 2008, vol. 37, pp. 664-665.*
International Search Report and Written Opinion issued in related International Application No. PCT/US2015/036054 dated Sep. 2, 2015.
Atienza et al. *Angewandte Chemie Int. Ed.* 2011, 50, 8143-8147.
Boller et al. *JACS* 2005, 127, 14263-14278.
Campos K. *Chemical Society Reviews* 2007, 36, 1069-1084.
Cheng et al. *Chemical Communications* 2012, 48, 8440-8442.
Cho et al. *JACS* 2000, 122, 12868-12869.

(Continued)

*Primary Examiner* — Joseph R Kosack
(74) *Attorney, Agent, or Firm* — Meunier Carlin & Curfman LLC

(57) ABSTRACT

Methods for the selective borylation of arenes, including arenes substituted with an electron-withdrawing group (e.g., 1-chloro-3-fluoro-2-substituted benzenes) are provided. The methods can be used, in some embodiments, to efficiently and regioselectively prepare borylated arenes without the need for expensive cryogenic reaction conditions.

13 Claims, No Drawings

(56) References Cited

OTHER PUBLICATIONS

Cho et al. *Science* 2002, 295, 305-308.
Chotana et al. *JACS* 2005, 126, 10539-10544.
Chotana et al. *Tetrahedron* 2008, 64, 6103-6114.
Chotanta et al. *Chemical Communications* 2009, 38, 5731-5733.
Frieman, et al., *Synthesis* 2005, 17, 2989-2993.
Gilman et al. *JACS* 1939, 61, 109-112.
Hung-Low F et al. *Chemical Communications* 2012, 48, 368-370.
Hung-Low F et al. *Dalton Transactions* 2012, 41, 8190-8197.
International Search Report and Written Opinion dated Dec. 22, 2014 in related matter PCT/US2014/054366.
Ishiyama et al. *Angewandte Chemie Int. Ed.* 2002, 41, 3056-3058.
Ishiyama et al. *JACS* 2002, 124, 390-391.
Ishiyama T et al. *Chemical Communications* 2010, 46, 159-161.
Ito et al. *Organometallics* 2012, 31, 4442-4449.
Itoh H et al. *Chemistry Letters* 2011, 40, 1007-1008.
Iverson et al. *JACS* 1999, 121, 7696-7697.
Chen et al. *Science* 2000, 287, 1995-1997.
Kawamorita S et al. *JACS* 2009, 131, 5058.
Lipshutz, et al., *Organic Letters* 2008, 10, 4279.
Liskey et al. *Chemical Commununications* 2009, 37, 5603-5605.
Liskey et al. *JACS* 2010, 132, 11389-11391.
Maleczka et al. *Tetrahedron Letters* 2002, 43, 7087-7090.
Miyaura, N. and Suzuki, A. *Chem. Rev.* 1995, 95, 2457.
Mkhalid IA et al. *Chemical Reviews* 2010, 110, 890-931.
Obligacion et al. *JACS* 2014, 136(11), 4133-4136.
Obligacion et al. *Organic Letters* 2013, 15(11), 2680-2683.
Partridge et al. *Organic Letters* 2013, 15, 140-143.
Preshlock et al. *JACS* 2013, 135, 7572-7582.
Rahaim RJ and Maleczka RE. *Tetrahedron Letters,* 2002, 40, 8823-8826.
Robbins et al. *Organic Letters* 2012, 14, 4266-4269.
Roering AJ et al. *Organic Lett.* 2012, 14, 3558.
Schlosser M. *Angewandte Chemie International Edition* 2005, 44, 376-393.
Shimada et al. *Angewandte Chemie Int. Ed.* 2001, 40, 2168-2171.
Snieckus V. *Chemical Reviews* 1990, 90, 879-933.
Stanforth, S. P. *Tetrahedron* 1998, 54, 263.
Tajuddin et al. *Chemical Science* 2012, 3, 3505-3515.
Takagi et al. *Tetrahedron Letters* 2002, 43, 5649-5654.
Tilly et al. *Tetrahedron Letters* 2002, 43, 8347-8350.
Tse et al. *Organic Letters* 2001, 3, 2831-2833.
Tsukamoto, H.; Kondo, Y. *Org. Lett.* 2007, 9, 4227.
Vanchura et al. *Chemical Communications* 2010, 46, 7724-7726.
Wang et al. *Tetrahedron Letters* 1991, 32, 4883-4884.
Watanabe et al. *Chemical and Pharmaceutical Bulletin* 1983, 31, 2662-2668.
Whisler, M. C., et al., *Angew. Chem., Int. Ed.* 2004, 43, 2206-2225.
Winkle et al. *Journal of Organic Chemistry* 1982, 47, 2101-2108.
Yu et al. *JACS* 2013, 135, 13168-13184.
Zeni et al. *Tetrahedron Letters* 2003, 44, 1387-1390.
Harrisson, P., et a. "Microwave-Accelerated Iridium-Catalyzed Borylation of Aromatic C—H Bonds." Organic Letters, 2009, 11(16): 3586-3589.
Ishiyama, T. et al., "Room temperature borylation of arenes and heteroarenes using stoichiometric amounts of pinacolborane catalyzed by iridium complexes in an inert solvent." Chemical Commnunications, 2003, 23: 2924-2925.
Ishiyama, T., et al. "Ortho-C—H borylation of benzoate esters with bis(pinacolato)diboron catalyzed by iridium-phosphine complexes." Chemical Communications, 2010, 46: 159-161.
Murphy, J.M., et al. "One-Pot Synthesis of Arylboronic Acids and Aryl Trifuroborates by Ir-Catalyzed Borylation of Arenes," Organic Letters, 2007, 9(5): 757-760.

\* cited by examiner

METHODS FOR PRODUCING BORYLATED ARENES

CROSS REFERENCE TO RELATED APPLICATIONS

This application claims the benefit of U.S. Provisional Patent Application Ser. No. 61/874,249 filed Sep. 5, 2013, and U.S. Provisional Patent Application Ser. No. 62/012,684 filed Jun. 16, 2014, the disclosures of which are expressly incorporated herein by reference.

TECHNICAL FIELD

This application relates generally to methods of forming borylated arenes, as well as methods of using thereof.

BACKGROUND

Arylboronic acids and arylboronic acid esters are versatile reagents in organic chemistry. In particular, arylboronic acids and arylboronic acid esters can participate in a variety of cross-coupling reactions, such as Suzuki-type cross-coupling reactions, which can result in carbon-carbon bond formation, as generally illustrated below.

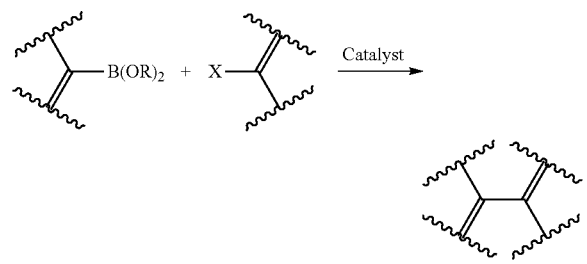

As a consequence, arylboronic acid esters and arylboronic acids are frequently key intermediates in the synthesis of highly functionalized organic compounds, including pharmaceuticals and agrochemicals. Improved methods for preparing arylboronic acids and arylboronic acid esters, including regioselective methods of preparing substituted arylboronic acids and substituted arylboronic acid esters, offer the potential to improve synthesis of important classes of organic compounds, including pharmaceuticals and agrochemicals.

SUMMARY

Metal-catalyzed C—H activation-borylation can be used to prepare arylboronic acids and arylboronic acid esters from their aromatic precursors in a single step. Metal-catalyzed C—H activation-borylation offers many advantages relative to alternative methods of borylation. For example, metal-catalyzed C—H activation-borylation does not require the cryogenic reaction temperatures that are typically required when using classical lithium-hydrogen exchange reactions to activate the C—H position for borylation.

In the case of arenes that are substituted with an electron-withdrawing group and that are unsubstituted in a position ortho to the electron-withdrawing group and unsubstituted in a position meta to the electron-withdrawing group, iridium-catalyzed C—H activation-borylation of the arene is typically governed by steric effects. For example, in the case of 1-chloro-3-fluoro-2-substituted benzenes, iridium-catalyzed C—H activation-borylation would be expected to favor borylation at the sterically-favored 5-position of the benzene ring (meta to the electron-withdrawing fluoro substituent, termed the "steric product") as opposed to borylation at the electronically-favored 4-position of the benzene ring (ortho to the electron-withdrawing fluoro substituent, termed the "electronic product")

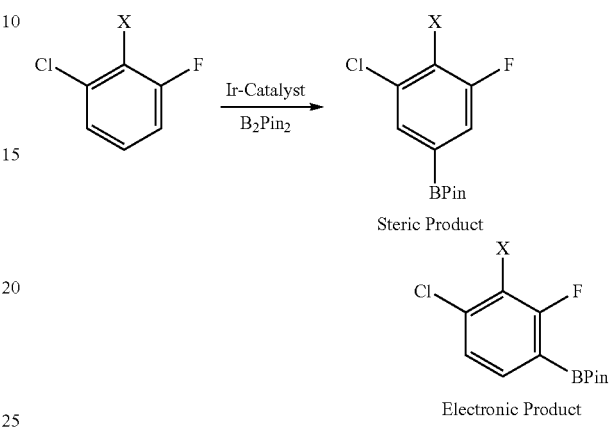

It has been unexpectedly discovered that certain iridium catalyst systems can effectively catalyze the borylation of arenes that are substituted with an electron-withdrawing group, including 1-chloro-3-fluoro-2-substituted benzenes, at positions ortho to the fluoro substituent (i.e., they can effectively catalyze formation of the electronic product).

Accordingly, provided are methods for preparing borylated arenes. In some embodiments, the borylated arenes can comprise a phenyl ring substituted with an electron-withdrawing group selected from the group consisting of —F and —CF$_3$, and a boronic acid or a boronic acid derivative in a position ortho to the electron-withdrawing group. Methods of forming borylated arenes can comprise contacting a suitable substrate with an iridium precursor complex, a ligand chosen from a monodentate ligand and a bidentate ligand, and a borylation reagent under conditions effective to form a first borylated arene and optionally a second borylated arene. The molar ratio of the first borylated arene to the second borylated arene, as determined using gas chromatography (e.g., a gas chromatograph equipped with a flame ionization detector; GC-FID), can be at least 1:1.

The substrate for the preparation of borylated arenes can comprise a phenyl ring which is substituted with an electron-withdrawing group selected from the group consisting of —F and —CF$_3$, and which is unsubstituted in a position ortho to the electron-withdrawing group and unsubstituted in a position meta to the electron-withdrawing group. The first borylated arene can comprise a phenyl ring substituted with an electron-withdrawing group selected from the group consisting of —F and —CF$_3$, and a boronic acid or a boronic acid derivative in a position ortho to the electron-withdrawing group. The second borylated arene can comprise a phenyl ring substituted with an electron-withdrawing group selected from the group consisting of —F and —CF$_3$, and a boronic acid or a boronic acid derivative in a position meta to the electron-withdrawing group.

For example, in some embodiments, the substrate can comprise a compound defined by Formula I

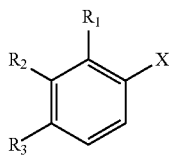

Formula I wherein
X is F or CF$_3$;

R$_1$ is hydrogen, a halogen, —OR$_4$, —NR$_5$R$_6$, —C(=O)R$_7$, a nitrile group, a C$_1$-C$_6$ alkyl group, or a C$_1$-C$_6$ haloalkyl group;

R$_2$ is hydrogen, a halogen, —OR$_4$, —NR$_5$R$_6$, —C(=O)R$_7$, a nitrile group, a C$_1$-C$_6$ alkyl group, or a C$_1$-C$_6$ haloalkyl group;

R$_3$ is hydrogen, a halogen, —OR$_4$, —NR$_5$R$_6$, —C(=O)R$_7$, a nitrile group, a C$_1$-C$_6$ alkyl group, or a C$_1$-C$_6$ haloalkyl group;

R$_4$, R$_5$, and R$_6$ are each, individually for each occurrence, hydrogen or a C$_1$-C$_6$ alkyl group; and R$_7$ is, individually for each occurrence, hydrogen, —OR$_4$, —NR$_5$R$_6$, or a C$_1$-C$_6$ alkyl group.

In these embodiments, the first borylated arene can comprise a compound defined by Formula II

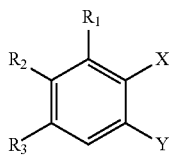

Formula II wherein X, R$_1$, R$_2$, and R$_3$ are as described above, and Y is a boronic acid or a boronic acid derivative; and the second borylated arene can comprise a compound defined by Formula III

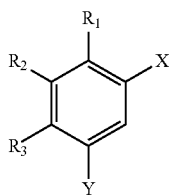

Formula III wherein X, R$_1$, R$_2$, and R$_3$ are as described above, and Y is a boronic acid or a boronic acid derivative.

In certain embodiments, the substrate can comprise 1-chloro-3-fluoro-2-methoxybenzene, the structure of which is shown below.

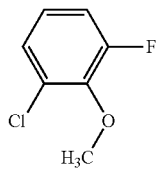

In some of these embodiments, the first borylated arene formed from 1-chloro-3-fluoro-2-methoxybenzene can comprise (4-chloro-2-fluoro-3-methoxyphenyl)boronic acid or a (4-chloro-2-fluoro-3-methoxyphenyl)boronic acid derivative (e.g., a (4-chloro-2-fluoro-3-methoxyphenyl)boronic acid ester such as 2-(4-chloro-2-fluoro-3-methoxyphenyl)-4,4,5,5-tetramethyl-1,3,2-dioxaborolane).

In some embodiments, the ligand can be a monodentate ligand (e.g., a pyridine ligand). In some embodiments, the pyridine ligand can be a compound defined by the formula below

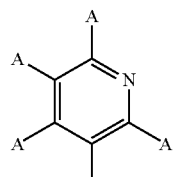

wherein A is, independently for each occurrence, hydrogen, halogen, —OR$_{13}$, —NR$_{14}$R$_{15}$, —C(=O)R$_{16}$, —OC(=O)R$_{16}$, a nitrile group, a C$_1$-C$_6$ alkyl group, a C$_1$-C$_6$ haloalkyl group, and a C$_1$-C$_6$ aminoalkyl group, wherein R$_{13}$, R$_{14}$, and R$_{15}$ are each, individually for each occurrence, hydrogen, a C$_1$-C$_6$ alkyl group, or an aryl group, and R$_{16}$ is, individually for each occurrence, hydrogen, —OR$_{13}$, —NR$_{14}$R$_{15}$, a C$_1$-C$_6$ alkyl group, or an aryl group, with the proviso that one or more of A is not hydrogen.

In certain embodiments, the pyridine ligand can be a compound defined by the formula below

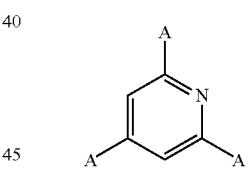

wherein A is, independently for each occurrence, hydrogen, halogen, —OR$_{13}$, —NR$_{14}$R$_{15}$, —C(=O)R$_{16}$, —OC(=O)R$_{16}$, a nitrile group, a C$_1$-C$_6$ alkyl group, a C$_1$-C$_6$ haloalkyl group, and a C$_1$-C$_6$ aminoalkyl group, wherein R$_{13}$, R$_{14}$, and R$_{15}$ are each, individually for each occurrence, hydrogen, a C$_1$-C$_6$ alkyl group, or an aryl group, and R$_{16}$ is, individually for each occurrence, hydrogen, —OR$_{13}$, —NR$_{14}$R$_{15}$, a C$_1$-C$_6$ alkyl group, or an aryl group, with the proviso that one or more of A is not hydrogen.

In some embodiments, the ligand can be a bidentate ligand. The bidentate ligand can be an electron-deficient bidentate ligand. For example, in some embodiments, the bidentate ligand can comprises a 2,2'-bipyridine substituted with one or more electron-withdrawing substituents (e.g., a 2,2'-bipyridine substituted with one or more trifluoromethyl groups). In certain embodiments, the bidentate ligand can comprise a compound defined by Formula IVa, Formula IVb, or Formula IVc

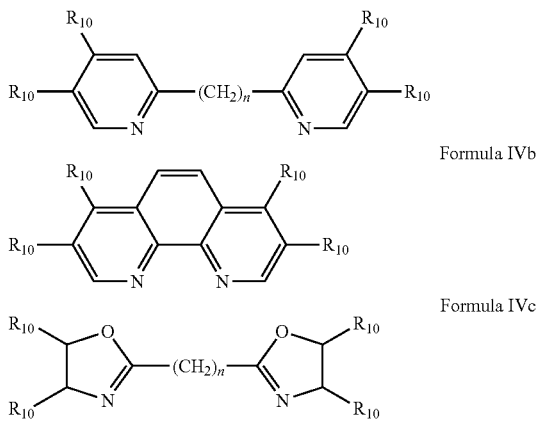

Formula IVa

Formula IVb

Formula IVc wherein n is 0, 1, 2, or 3 and $R_{10}$ is, independently for each occurrence, hydrogen, a halogen, a nitrile group, a nitro group, a $C_1$-$C_6$ alkyl group, or a $C_1$-$C_6$ perfluoroalkyl group, with the proviso that one or more of $R_{10}$ is not hydrogen when the bidentate ligand comprises a compound defined by Formula IVa or Formula IVb.

Also provided are methods of forming borylated arenes from a substrate that comprises an aromatic ring substituted with a moiety chosen from an electron-withdrawing group and a directed metalating group, and unsubstituted in a position ortho to the moiety. The methods can comprise contacting the substrate with an iridium precursor complex, a monodentate ligand, and a borylation reagent under conditions effective to form a first borylated arene (i.e., an aromatic ring substituted with a moiety chosen from an electron withdrawing group and a directed metalating group, and a boronic acid or a boronic acid derivative in a position ortho to the moiety).

In certain embodiments, the aromatic ring can be unsubstituted in a position ortho to the moiety and unsubstituted in a position meta to the moiety. In these embodiments, the methods can comprise contacting the substrate with an iridium precursor complex, a monodentate ligand, and a borylation reagent under conditions effective to form the first borylated arene and a second borylated arene, wherein the second borylated arene comprises an aromatic ring substituted with a moiety chosen from an electron-withdrawing group and a directed metalating group, and a boronic acid or a boronic acid derivative in a position meta to the moiety. In some embodiments, the molar ratio of the first borylated arene to the second borylated arene is at least 1:1, as determined by GC-FID.

The substrate can be a substituted aryl compound, a substituted six-membered heteroaromatic compound, a substituted five-membered heteroaromatic compound, or a combination thereof. In some cases, the moiety can be an electron-withdrawing group selected from the group consisting of —F and —CF$_3$. In some cases, the moiety can be a directed metalating group. In certain embodiments, the directed metalating group can be selected from the group consisting of –OR$_{13}$, —NR$_{14}$R$_{15}$, —C(=O)R$_{16}$, —OC(=O)R$_{16}$, a nitrile group, —SO$_2$R$_{16}$, —SOR$_{16}$, or a $C_1$-$C_6$ aminoalkyl group, wherein R$_{13}$, R$_{14}$, and R$_{15}$ are each, individually for each occurrence, hydrogen, a $C_1$-$C_6$ alkyl group, or an aryl group, and R$_{16}$ is, individually for each occurrence, hydrogen, —OR$_{13}$, —NR$_{14}$R$_{15}$, a $C_1$-$C_6$ alkyl group, or an aryl group.

In some embodiments, the monodentate ligand can be a monodentate pyridine ligand. In some embodiments, the pyridine ligand can be a compound defined by the formula below

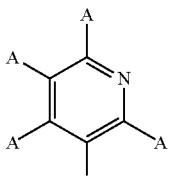

wherein A is, independently for each occurrence, hydrogen, halogen, —OR$_{13}$, —NR$_{14}$R$_{15}$, —C(=O)R$_{16}$, —OC(=O)R$_{16}$, a nitrile group, a $C_1$-$C_6$ alkyl group, a $C_1$-$C_6$ haloalkyl group, and a $C_1$-$C_6$ aminoalkyl group, wherein R$_{13}$, R$_{14}$, and R$_{15}$ are each, individually for each occurrence, hydrogen, a $C_1$-$C_6$ alkyl group, or an aryl group, and R$_{16}$ is, individually for each occurrence, hydrogen, —OR$_{13}$, —NR$_{14}$R$_{15}$, a $C_1$-$C_6$ alkyl group, or an aryl group, with the proviso that one or more of A is not hydrogen.

In certain embodiments, the pyridine ligand can be a compound defined by the formula below

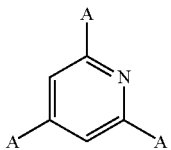

wherein A is, independently for each occurrence, hydrogen, halogen, —OR$_{13}$, —NR$_{14}$R$_{15}$, —C(=O)R$_{16}$, —OC(=O)R$_{16}$, a nitrile group, a $C_1$-$C_6$ alkyl group, a $C_1$-$C_6$ haloalkyl group, and a $C_1$-$C_6$ aminoalkyl group, wherein R$_{13}$, R$_{14}$, and R$_{15}$ are each, individually for each occurrence, hydrogen, a $C_1$-$C_6$ alkyl group, or an aryl group, and R$_{16}$ is, individually for each occurrence, hydrogen, —OR$_{13}$, —NR$_{14}$R$_{15}$, a $C_1$-$C_6$ alkyl group, or an aryl group, with the proviso that one or more of A is not hydrogen.

Also provided are methods of forming borylated arenes from a substrate that comprises a substituted arene ring comprising from 1 to 4 substituents (e.g., from 1 to 3 substituents), wherein the arene ring is unsubstituted at a first position that is electronically favored for CH-activation and unsubstituted at a second position that is sterically favored for CH-activation. In these embodiments, methods can comprise contacting the substrate with an iridium precursor complex, a ligand chosen from a monodentate ligand and a bidentate ligand, and a borylation reagent under conditions effective to form a first borylated arene and optionally a second borylated arene. The first borylated arene can comprise a substituted arene ring comprising from 1 to 4 substituents (e.g., from 1 to 3 substituents) and a boronic acid or a boronic acid derivative in the first position. The second borylated arene, when formed, can comprise a substituted arene ring comprising from 1 to 4 substituents (e.g., from 1 to 3 substituents) and a boronic acid or a boronic acid derivative in the second position. The molar ratio of the first borylated arene to the second borylated arene can be at least 1:1, as determined by GC-FID.

In some cases, the arene ring can comprise a phenyl ring. For example, in some embodiments, the substrate can comprise a compound defined by Formula I

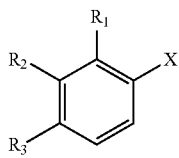

Formula I wherein

X is F or $CF_3$;

$R_1$ is hydrogen, a halogen, —$OR_4$, —$NR_5R_6$, —C(=O)$R_7$, a nitrile group, a $C_1$-$C_6$ alkyl group, or a $C_1$-$C_6$ haloalkyl group;

$R_2$ is hydrogen, a halogen, —$OR_4$, —$NR_5R_6$, —C(=O)$R_7$, a nitrile group, a $C_1$-$C_6$ alkyl group, or a $C_1$-$C_6$ haloalkyl group;

$R_3$ is hydrogen, a halogen, —$OR_4$, —$NR_5R_6$, —C(=O)$R_7$, a nitrile group, a $C_1$-$C_6$ alkyl group, or a $C_1$-$C_6$ haloalkyl group;

$R_4$, $R_5$, and $R_6$ are each, individually for each occurrence, hydrogen or a $C_1$-$C_6$ alkyl group; and $R_7$ is, individually for each occurrence, hydrogen, —$OR_4$, —$NR_5R_6$, or a $C_1$-$C_6$ alkyl group.

In these embodiments, the first borylated arene can comprise a compound defined by Formula II

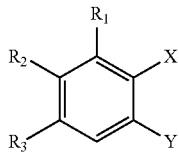

Formula II wherein X, $R_1$, $R_2$, and $R_3$ are as described above, and Y is a boronic acid or a boronic acid derivative; and the second borylated arene can comprise a compound defined by Formula III

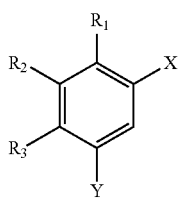

Formula III wherein X, $R_1$, $R_2$, and $R_3$ are as described above, and Y is a boronic acid or a boronic acid derivative.

In certain embodiments, the substrate can comprise 1-chloro-3-fluoro-2-methoxybenzene, the structure of which is shown below.

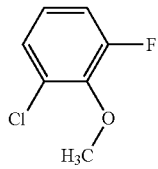

In some of these embodiments, the first borylated arene formed from 1-chloro-3-fluoro-2-methoxybenzene can comprise (4-chloro-2-fluoro-3-methoxyphenyl)boronic acid or a (4-chloro-2-fluoro-3-methoxyphenyl)boronic acid derivative (e.g., a (4-chloro-2-fluoro-3-methoxyphenyl)boronic acid ester such as 2-(4-chloro-2-fluoro-3-methoxyphenyl)-4,4,5,5-tetramethyl-1,3,2-dioxaborolane).

In some cases, the arene ring can comprise a pyridine ring. In certain cases, the pyridine ring can comprise a 2-substituted pyridine ring. In certain cases, the pyridine ring can comprises a 2,4-disubstituted pyridine ring, a 2,6-disubstituted pyridine ring, or a 2,4,6-trisubstituted pyridine ring. The 1 to 3 substituents present on the arene ring can be individually selected from halogen, —$OR_{13}$, —$NR_{14}R_{15}$, —C(=O)$R_{16}$, —OC(=O)$R_{16}$, a nitrile group, a $C_1$-$C_6$ alkyl group, a $C_1$-$C_6$ haloalkyl group, and a $C_1$-$C_6$ aminoalkyl group, wherein $R_{13}$, $R_{14}$, and $R_{15}$ are each, individually for each occurrence, hydrogen, a $C_1$-$C_6$ alkyl group, or an aryl group, and $R_{16}$ is, individually for each occurrence, hydrogen, —$OR_{13}$, —$NR_{14}R_{15}$, a $C_1$-$C_6$ alkyl group, or an aryl group. In certain cases, the arene ring comprises an electron-withdrawing group selected from the group consisting of —F and —$CF_3$.

In some embodiments, the ligand can be a monodentate ligand (e.g., a pyridine ligand). In some embodiments, the pyridine ligand can be a compound defined by the formula below

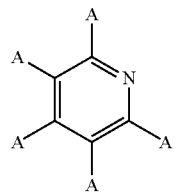

wherein A is, independently for each occurrence, hydrogen, halogen, —$OR_{13}$, —$NR_{14}R_{15}$, —C(=O)$R_{16}$, —OC(=O)$R_{16}$, a nitrile group, a $C_1$-$C_6$ alkyl group, a $C_1$-$C_6$ haloalkyl group, and a $C_1$-$C_6$ aminoalkyl group, wherein $R_{13}$, $R_{14}$, and $R_{15}$ are each, individually for each occurrence, hydrogen, a $C_1$-$C_6$ alkyl group, or an aryl group, and $R_{16}$ is, individually for each occurrence, hydrogen, —$OR_{13}$, —$NR_{14}R_{15}$, a $C_1$-$C_6$ alkyl group, or an aryl group, with the proviso that one or more of A is not hydrogen.

In certain embodiments, the pyridine ligand can be a compound defined by the formula below

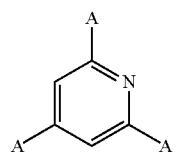

wherein A is, independently for each occurrence, hydrogen, halogen, —$OR_{13}$, —$NR_{14}R_{15}$, —C(=O)$R_{16}$, —OC(=O)$R_{16}$, a nitrile group, a $C_1$-$C_6$ alkyl group, a $C_1$-$C_6$ haloalkyl group, and a $C_1$-$C_6$ aminoalkyl group, wherein $R_{13}$, $R_{14}$, and $R_{15}$ are each, individually for each occurrence, hydrogen, a $C_1$-$C_6$ alkyl group, or an aryl group, and $R_{16}$ is, individually for each occurrence, hydrogen, —$OR_{13}$, —$NR_{14}R_{15}$, a $C_1$-$C_6$ alkyl group, or an aryl group, with the proviso that one or more of A is not hydrogen.

In some embodiments, the ligand can be a bidentate ligand. The bidentate ligand can be an electron-deficient bidentate ligand. For example, in some embodiments, the bidentate ligand can comprises a 2,2'-bipyridine substituted with one or more electron-withdrawing substituents (e.g., a 2,2'-bipyridine substituted with one or more trifluoromethyl groups). In certain embodiments, the bidentate ligand can comprise a compound defined by Formula IVa, Formula IVb, or Formula IVc

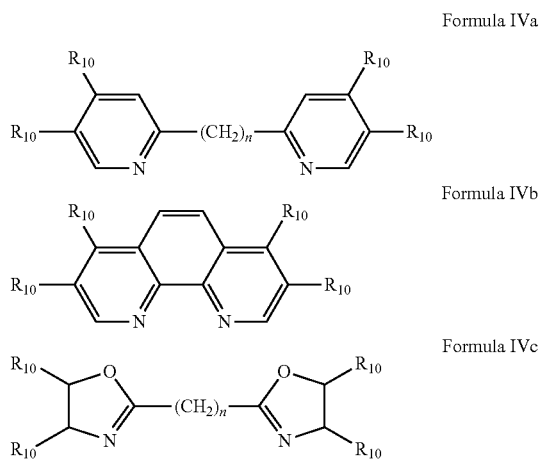

Formula IVa

Formula IVb

Formula IVc wherein n is 0, 1, 2, or 3 and $R_{10}$ is, independently for each occurrence, hydrogen, a halogen, a nitrile group, a nitro group, a $C_1$-$C_6$ alkyl group, or a $C_1$-$C_6$ perfluoroalkyl group, with the proviso that one or more of $R_{10}$ is not hydrogen when the bidentate ligand comprises a compound defined by Formula IVa or Formula IVb.

Also provided are methods for the regioselective borylation of substrates, including methods of forming exclusively the electronic borylation product. In some embodiments, regioselective borylation methods can comprise tandem borylation/dehalogenation. For example, methods for the regioselective borylation of arenes can comprise contacting a suitable substrate with an iridium precursor complex, a ligand chosen from a monodentate ligand and a bidentate ligand, and a borylation reagent under conditions effective to form a first borylated arene and optionally a second borylated arene, wherein the molar ratio of the first borylated arene to the second borylated arene, as determined using GC-FID is at least 25:1. The substrate can comprise, for example, a phenyl ring which is substituted with an electron-withdrawing group selected from the group consisting of —F and —CF$_3$, which is unsubstituted in a position ortho to the electron-withdrawing group, and which further includes a sacrificial moiety (e.g., a halogen such as Cl or Br) positioned so as to hinder steric attack of the iridium catalyst at the otherwise sterically favored position meta to the electron-withdrawing group (e.g., a Cl or Br substituent para to the electron-withdrawing group). As a result, iridium-catalyzed C—H activation-borylation of the arene exclusively generates the ortho-borylated electronic product (i.e., the first borylated arene).

Methods can further comprise reductively dehalogenating the first borylated arene to obtain a dehalogenated borylated arene. The first borylated arene can be reductively dehalogenated using any suitable synthetic method. For example, methods for reductively dehalogenating the first borylated arene can comprise contacting the first borylated arene with polymethylhydrosiloxane (PMHS), a base (e.g., potassium fluoride (KF) or a tetraalkylammonium salt such as tetra-n-butylammonium fluoride (TBAF)), and a metal catalyst (e.g., palladium(II) acetate) under conditions effective to reductively dehalogenate the first borylated arene. The metal catalyst can comprise a variety of metal catalysts which can accept a hydride from PMHS, and subsequently participate in the reductive dehalogenation of the first borylated arene. Suitable metal catalysts can be selected in view of a number of factors, including the identity of the first borylated arene (e.g., the identity of the halogen being hydrodehalogenated). For example, the metal catalyst can comprise palladium (Pd), tin (Sn), titanium (Ti), zinc (Zn), or copper (Cu). In certain embodiments, the metal catalyst can comprise a palladium(II) catalyst, such as palladium(II) acetate (Pd (OAc)$_2$), or a palladium(0) catalyst, such as tetrakis(triphenylphosphine)palladium(0) (Pd(Ph$_3$P)$_4$).

In certain embodiments, the methods for reductively dehalogenating the first borylated arene can comprise contacting the first borylated arene with a formate salt and a transition metal catalyst under conditions effective to reductively dehalogenate the first borylated arene. The formate salt can be any suitable formate salt, such as ammonium formate. The transition metal catalyst can comprise a palladium(0) catalyst, such as palladium on carbon. In certain embodiments, the borylation and dehalogenation described above can be performed using a one-pot synthetic methodology.

Borylated arenes prepared using the methods described herein can be utilized in additional chemical reactions, including cross-coupling reactions, such as Suzuki-type cross-coupling reactions. In some embodiments, the methods described herein can further comprise contacting the first borylated arene or the dehalogenated borylated arene with a reactant selected from the group consisting of an aryl halide, an aryl pseudohalide, a vinyl halide, and a vinyl pseudohalide, and a transition metal catalyst to cross-couple the reactant and the first borylated arene or the dehalogenated borylated arene.

Also provided are catalytic iridium complexes that can catalyze the borylation of arenes that are substituted with an electron-withdrawing group, including 1-chloro-3-fluoro-2-substituted benzenes, at positions ortho to the fluoro substituent. Catalytic iridium complexes can be formed by combination of the iridium precursor complex, the monodentate or bidentate ligand, and the borylation reagent.

DETAILED DESCRIPTION

Definitions

Terms used herein will have their customary meaning in the art unless specified otherwise. The organic moieties mentioned in the definitions of the variables of the formulae described herein are—like the term halogen—collective terms for individual listings of the individual group members. The prefix $C_n$-$C_m$ indicates in each case the possible number of carbon atoms in the group.

The term "alkyl," as used herein, refers to saturated straight, branched, cyclic, primary, secondary or tertiary hydrocarbons, including those having 1 to 6 carbon atoms. In some embodiments, alkyl groups will include $C_1$, $C_1$-$C_2$, $C_1$-$C_3$, $C_1$-$C_4$, $C_1$-$C_5$ or $C_1$-$C_6$ alkyl groups. Examples of $C_1$-$C_6$ alkyl groups include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, and their isomers. $C_1$-$C_4$-alkyl groups can include, for example, methyl, ethyl, propyl, 1-methylethyl, butyl, 1-methylpropyl, 2-methylpropyl, and 1,1-dimethylethyl.

Cyclic alkyl groups or "cycloalkyl" groups, which are encompassed by alkyl, include those with 3 to 6 carbon atoms having single or multiple condensed rings. In some embodiments, cycloalkyl groups include $C_4$-$C_6$ or $C_3$-$C_4$ cyclic alkyl groups. Non-limiting examples of cycloalkyl groups include cyclopropyl, cyclobutyl, cyclopentyl, and cyclohexyl groups.

Alkyl groups can be unsubstituted or substituted with one or more moieties, such as alkyl, halo, haloalkyl, hydroxyl, carboxyl, acyl, acyloxy, amino, alkyl- or dialkylamino, amido, nitro, cyano, azido, thiol, or any other viable functional group that does not preclude the synthetic methods described herein, either unprotected, or protected as necessary, as known to those skilled in the art, for example, as taught in Greene, et al., *Protective Groups in Organic Synthesis*, John Wiley and Sons, Fourth Edition, 2007, hereby incorporated by reference.

The term "haloalkyl," as used herein, refers to an alkyl group, as defined above, which is substituted by one or more halogen atoms. For example $C_1$-$C_4$-haloalkyl includes, but is not limited to, chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like.

The term "alkoxy," also defined as —OR where R is alkyl, refers to —O- alkyl, wherein alkyl is as defined above. Similarly, the term haloalkoxy can be used to refer to —O- haloalkyl, wherein haloalkyl is as defined above. In some embodiments, alkoxy groups can include 1 to 6 carbon atoms. Examples of $C_1$-$C_6$-alkoxy groups include, but are not limited to, methoxy, ethoxy, $C_2H_5$—$CH_2O$—, $(CH_3)_2CHO$—, n-butoxy, $C_2H_5$—$CH(CH_3)O$—, $(CH_3)_2CH$—$CH_2O$—, $(CH_3)_3CO$—, n-pentoxy, 1-methylbutoxy, 2-methylbutoxy, 3-methylbutoxy, 1,1-dimethylpropoxy, 1,2-dimethylpropoxy, 2,2-dimethyl-propoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, and 1-ethyl-2-methylpropoxy.

The terms "alkylamino" and "dialkylamino" refer to alkyl-NH— and $(alkyl)_2N$— where alkyl is as defined above. Similarly, the terms haloalkylamino and halodialkylamino refer to haloalkyl-NH— and $(haloalkyl)_2$-NH—, where haloalkyl is as defined above. The term "aminoalkyl" refers to an alkyl group, as defined above, substituted with an amino group.

The terms "alkylcarbonyl," "alkoxycarbonyl," "alkylaminocarbonyl," and "dialkylaminocarbonyl" refer to —C(=O)-alkyl, —C(O)-alkoxy, —C(O)-alkylamino, and —C(O)-dialkylamino, where alkyl, alkoxy, alkylamino, and dialkylamino are as defined above.

The term "boronic acid," as used herein, refers to a —B(OH)$_2$ moiety. The term boronic acid derivative refers to boron-containing moieties which differ from boronic acid in the presence or absence of one or more atoms, functional groups, or substructures, and which can be imagined to be formed, at least theoretically, from boronic acid via some chemical or physical process. Examples of boronic acid derivatives include boronic acid esters, also referred to as boronates, boronate esters, or boronic esters; aminoboranes, including cyclic aminoboranes such as 1,3,2-diazaborolidyl group; and boronic acid anhydrides. The term boronic acid ester refers to an esterified boronic acid moiety, such as —B(OR)$_2$ where R is an alkyl group as defined above, and cyclic boronic acid moieties represented by —B(OR)$_2$ wherein the two R substituents are linked together so as to form a $C_2$-$C_6$ cyclic moiety optionally including one or more additional heteroatoms (e.g., N, O, S, or combinations thereof), and optionally further substituted with one or more substituents and/or fused with (sharing at least one bond) one or more further carbocyclyl or heterocarbocyclyl groups. Examples of cyclic boronic esters include, but are not limited to, pinanediol boronic esters, pinacol boronic esters, 1,2-ethanediol boronic esters, 1,3-propanediol boronic esters, 1,2-propanediol boronic esters, 2,3-butanediol boronic esters, 1,1,2,2-tetramethylethanediol boronic esters, 1,2-diisopropylethanediol boronic esters, 5,6-decanediol boronic esters, 1,2-dicyclohexylethanediol boronic esters, bicyclohexyl-1,1'-diol boronic esters, diethanolamine boronic esters, and 1,2-diphenyl-1,2-ethanediol boronic esters.

The term "halogen" refers to the atoms fluorine, chlorine, bromine and iodine. The prefix halo- (e.g., as illustrated by the term haloalkyl) refers to all degrees of halogen substitution, from a single substitution to a perhalo substitution (e.g., as illustrated with methyl as chloromethyl (—$CH_2Cl$), dichloromethyl (—$CHCl_2$), trichloromethyl (—$CCl_3$)).

The term "arene" is used herein generally to refer to an aromatic ring or multiple aromatic rings that are fused together. Examples of arenes include, for example, benzene, naphthalene, anthracene, and the like. The term arene also includes heteroarenes (i.e., aromatic compounds in which one or more of the carbon atoms in an aromatic ring has been replaced by a heteroatom, such as O, N, or S). Examples of heteroarenes include, for example, pyridine, furan, indole, benzimidazole, thiophene, benzthiazole, and the like.

Methods

Provided are methods for preparing borylated arenes. The borylated arenes can comprise a phenyl ring substituted with an electron-withdrawing group selected from the group consisting of —F and —$CF_3$, and a boronic acid or a boronic acid derivative in a position ortho to the electron withdrawing group. Methods of forming borylated arenes can comprise contacting a suitable substrate with an iridium precursor complex, a ligand chosen from a monodentate ligand and a bidentate ligand, and a borylation reagent under conditions effective to form a first borylated arene and optionally a second borylated arene. The molar ratio of the first borylated arene to the second borylated arene, as determined using gas chromatography (e.g., a gas chromatograph equipped with a flame ionization detector; GC-FID), can be at least 1:1.

The substrate for the preparation of borylated arenes can comprise a phenyl ring which is substituted with an electron-withdrawing group selected from the group consisting of —F and —$CF_3$, and which is unsubstituted in a position ortho to the electron-withdrawing group and unsubstituted in a position meta to the electron-withdrawing group. The phenyl ring can further include one or more additional substituents, such as a halogen (e.g., F, Cl, Br, I), a hydroxy group, an alkoxy group, an amino group (e.g., a primary amine, an alkyl amine, or a dialkylamine), a carboxylic acid, an alkylcarbonyl group, an alkoxycarbonyl group, an alkylaminocarbonyl group, a dialkylaminocarbonyl group, a nitrile group, an alkyl group (e.g., a $C_1$-$C_6$ alkyl group, or a $C_1$-$C_4$ alkyl group), a haloalkyl group (e.g., a $C_1$-$C_6$ haloalkyl group, or a $C_1$-$C_4$ haloalkyl group), or combinations thereof. In some embodiments, the substrate does not include a substituent which coordinates with an iridium metal center, such as a hydrosilyl group, a —$CO_2Me$ group, a —$CO_2tBu$ group, a —$CONMe_2$ group, an —$SO_3Me$ group, or a —$CH(O(CH_2)_3O)$ group.

The first borylated arene can comprise a phenyl ring substituted with an electron-withdrawing group selected from the group consisting of —F and —$CF_3$, and a boronic acid or a boronic acid derivative in a position ortho to the electron-withdrawing group. The second borylated arene can comprise a phenyl ring substituted with an electron-withdrawing group selected from the group consisting of —F and —$CF_3$, and a boronic acid or a boronic acid derivative in a position meta to the electron withdrawing group. The phenyl ring of the first borylated arene and the second borylated arene can further include one or more additional substituents present on the substrate from which they are formed, such as a halogen (e.g., F, Cl, Br, I), a hydroxy group, an alkoxy group, an amino group (e.g., a primary amine, an alkyl amine, or a dialkylamine), a carboxylic acid, an alkylcarbonyl group, an alkoxycarbonyl group, an alkylaminocarbonyl group, a dialkylaminocarbonyl group, a nitrile group, an alkyl group (e.g., a $C_1$-$C_6$ alkyl group, or a $C_1$-$C_4$ alkyl group), a haloalkyl group (e.g., a $C_1$-$C_6$ haloalkyl group, or a $C_1$-$C_4$ haloalkyl group), or combinations thereof.

For example, in some embodiments, the substrate can comprise a compound defined by Formula I

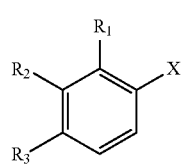

Formula I wherein

X is F or $CF_3$;

$R_1$ is hydrogen, a halogen, —$OR_4$, —$NR_5R_6$, —C(=O)$R_7$, a nitrile group, a $C_1$-$C_6$ alkyl group, or a $C_1$-$C_6$ haloalkyl group;

$R_2$ is hydrogen, a halogen, —$OR_4$, —$NR_5R_6$, —C(=O)$R_7$, a nitrile group, a $C_1$-$C_6$ alkyl group, or a $C_1$-$C_6$ haloalkyl group;

$R_3$ is hydrogen, a halogen, —$OR_4$, —$NR_5R_6$, —C(=O)$R_7$, a nitrile group, a $C_1$-$C_6$ alkyl group, or a $C_1$-$C_6$ haloalkyl group;

$R_4$, $R_5$, and $R_6$ are each, individually for each occurrence, hydrogen or a $C_1$-$C_6$ alkyl group; and $R_7$ is, individually for each occurrence, hydrogen, —$OR_4$, —$NR_5R_6$, or a $C_1$-$C_6$ alkyl group.

In these embodiments, the first borylated arene can comprise a compound defined by Formula II

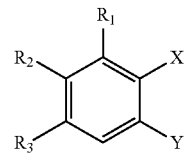

Formula II wherein X, $R_1$, $R_2$, and $R_3$ are as described above, and Y is a boronic acid or a boronic acid derivative; and the second borylated arene can comprise a compound defined by Formula III

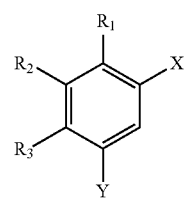

Formula III wherein X, $R_1$, $R_2$, and $R_3$ are as described above, and Y is a boronic acid or a boronic acid derivative.

Y can be boronic acid moiety (—$B(OH)_2$). Y can also be a boronic acid derivative, such as a boronic acid ester, aminoborane, or a boronic acid anhydride. In some embodiments, Y can be a boronic acid ester defined by the formula —$B(OR_{12})_2$, where each $R_{12}$ is independently an alkyl group (e.g., a $C_1$-$C_6$ alkyl group) as defined above. In other embodiments, Y can be a cyclic boronic acid ester defined by the formula —$B(OR_{12})_2$, wherein the two $R_{12}$ groups, taken together with the atoms to which they are attached, form a $C_2$-$C_6$ cyclic moiety. The $C_2$-$C_6$ cyclic moiety can optionally be substituted (e.g., with one or more $C_1$-$C_6$ alkyl groups). The $C_2$-$C_6$ cyclic moiety can optionally be fused with (sharing at least one bond) one or more carbocyclyl or heterocarbocyclyl groups. For example, Y can be a pinanediol boronic ester, pinacol boronic ester, 1,2-ethanediol boronic ester, 1,3-propanediol boronic ester, 1,2-propanediol boronic ester, 2,3-butanediol boronic ester, 1,1,2,2-tetramethylethanediol boronic ester, 1,2-diisopropylethanediol boronic ester, 5,6-decanediol boronic ester, 1,2-dicyclohexylethanediol boronic ester, bicyclohexyl-1,1'-diol boronic ester, diethanolamine boronic ester, or a 1,2-diphenyl-1,2-ethanediol boronic ester. In certain embodiments, Y is selected from one of the moieties below.

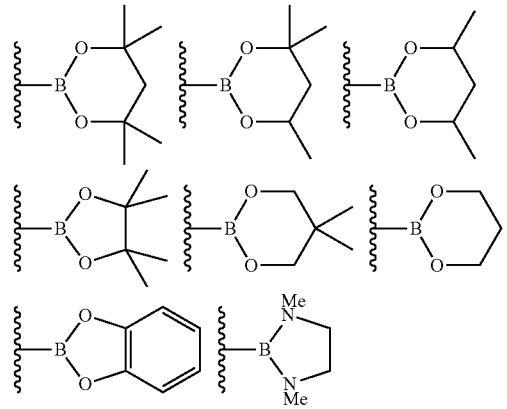

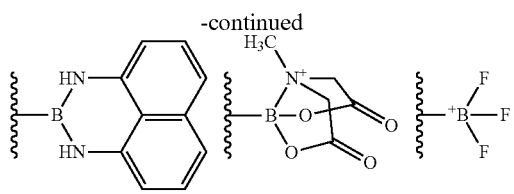

In some embodiments, the substrate can comprise a compound defined by Formula I, wherein $R_2$ is a halogen. In certain cases, $R_2$ can be a chloro group. In some embodiments, the substrate can comprise a compound of Formula I which is substituted at the $R_1$ position (e.g., $R_1$ can be a halogen, $-OR_4$, $-NR_5R_6$, $-C(=O)R_7$, a nitrile group, a $C_1$-$C_6$ alkyl group, or a $C_1$-$C_6$ haloalkyl group). In certain embodiments, the substrate can comprise a 1-chloro-3-fluoro-2-substituted benzene, a 1-chloro-3-trifluoromethyl-2-substituted benzene, a 1-bromo-3-fluoro-2-substituted benzene, or a 1-bromo-3-trifluoromethyl-2-substituted benzene, wherein the 2-position of the benzene ring is substituted with a halogen, $-OR_4$, $-NR_5R_6$, $-C(=O)R_7$, a nitrile group, a $C_1$-$C_6$ alkyl group, or a $C_1$-$C_6$ haloalkyl group.

In certain embodiments, the substrate can comprise 1-chloro-3-fluoro-2-methoxybenzene, the structure of which is shown below.

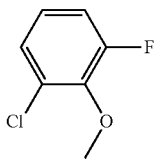

In some of these embodiments, the first borylated arene formed from 1-chloro-3-fluoro-2-methoxybenzene can comprise (4-chloro-2-fluoro-3-methoxyphenyl)boronic acid or a (4-chloro-2-fluoro-3-methoxyphenyl)boronic acid ester, such as 2-(4-chloro-2-fluoro-3-methoxyphenyl)-4,4,5,5-tetramethyl-1,3,2-dioxaborolane, the structure of which is shown below.

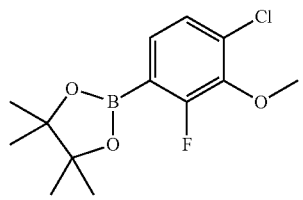

In other embodiments, the substrate can comprise a compound defined by Formula Ia

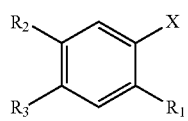

Formula Ia wherein
X is F or $CF_3$;
$R_1$ is hydrogen, a halogen, $-OR_4$, $-NR_5R_6$, $-C(=O)R_7$, a nitrile group, a $C_1$-$C_6$ alkyl group, or a $C_1$-$C_6$ haloalkyl group;
$R_2$ is hydrogen, a halogen, $-OR_4$, $-NR_5R_6$, $-C(=O)R_7$, a nitrile group, a $C_1$-$C_6$ alkyl group, or a $C_1$-$C_6$ haloalkyl group;
$R_3$ is hydrogen, a halogen, $-OR_4$, $-NR_5R_6$, $-C(=O)R_7$, a nitrile group, a $C_1$-$C_6$ alkyl group, or a $C_1$-$C_6$ haloalkyl group;
$R_4$, $R_5$, and $R_6$ are each, individually for each occurrence, hydrogen or a $C_1$-$C_6$ alkyl group; and
$R_7$ is, individually for each occurrence, hydrogen, $-OR_4$, $-NR_5R_6$, or a $C_1$-$C_6$ alkyl group.

In these embodiments, the first borylated arene can comprise a compound defined by Formula IIa

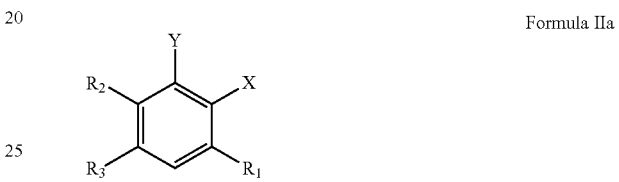

Formula IIa wherein X, $R_1$, $R_2$, and $R_3$ are as described above, and Y is a boronic acid or a boronic acid derivative, as described above; and the second borylated arene can comprise a compound defined by Formula IIIa

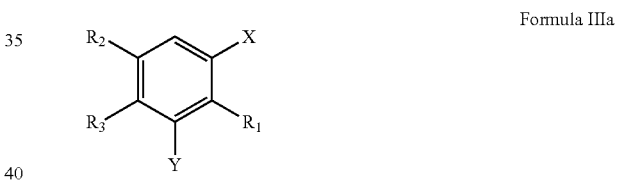

Formula IIIa wherein X, $R_1$, $R_2$, and $R_3$ are as described above, and Y is a boronic acid or a boronic acid derivative, as described above.

As described above, the substrate can comprise a phenyl ring which is substituted with an electron-withdrawing group selected from the group consisting of —F and —$CF_3$, and which is unsubstituted in a position ortho to the electron-withdrawing group and unsubstituted in a position meta to the electron-withdrawing group. The methods provided herein can favor borylation of the substrate at a position ortho to the electron-withdrawing group (the electronically-favored reaction product, termed the "electronic product") so as to form the first borylated arene, relative to borylation of the substrate at a position meta to the electron-withdrawing group (the sterically favored reaction product, termed the "steric product") so as to form the second borylated arene.

The molar ratio of the first borylated arene to the second borylated arene can be determined using standard methods known in the art, including gas chromatography (e.g., a gas chromatograph equipped with a flame ionization detector; GC-FID) and/or $^{19}$F nuclear magnetic resonance (NMR) spectroscopy. The molar ratio of the first borylated arene to the second borylated arene, as determined using GC-FID, can be at least 1:1 (e.g., at least 1.1:1, at least 1.2:1, at least 1.3:1, at least 1.4:1, at least 1.5:1, at least 1.6:1, at least 1.7:1, at least 1.8:1, at least 1.9:1, at least 2.0:1, at least 2.1:1, at least 2.2:1, at least 2.3:1, at least 2.4:1, at least 2.5:1, at least 2.6:1, at least 2.7:1, at least 2.8:1, at least 2.9:1, at least 3.0:1, at least 3.1:1, at least 3.2:1, at least 3.3:1, at least 3.4:1, at least 3.5:1, at least 3.6:1, at least 3.7:1, at least 3.8:1, at least 3.9:1, at least 4.0:1, at least 4.1:1, at least 4.2:1, at least 4.3:1, at least 4.4:1, at least 4.5:1, at least 4.6:1, at least 4.7:1, at least 4.8:1, at least 4.9:1, at least 5:1, at least 5.5:1, at least 6:1, at least 6.5:1, at least 7:1, at least 7.5:1, at least 8:1, at least 8.5:1, at least 9:1, at least 9.5:1, at least 10:1, at least 15:1, or at least 20:1). In some embodiments, the molar ratio of the first borylated arene to the second borylated arene, as determined using GC-FID, is 25:1 or less (e.g., 20:1 or less, 15:1 or less, 10:1 or less, 9.5:1 or less, 9:1 or less, 8.5:1 or less, 8:1 or less, 7.5:1 or less, 7:1 or less, 6.5:1 or less, 6:1 or less, 5.5:1 or less, 5:1 or less, 4.9:1 or less, 4.8:1 or less, 4.7:1 or less, 4.6:1 or less, 4.5:1 or less, 4.4:1 or less, 4.3:1 or less, 4.2:1 or less, 4.1:1 or less, 4:1 or less, 3.9:1 or less, 3.8:1 or less, 3.7:1 or less, 3.6:1 or less, 3.5:1 or less, 3.4:1 or less, 3.3:1 or less, 3.2:1 or less, 3.1:1 or less, 3:1 or less, 2.9:1 or less, 2.8:1 or less, 2.7:1 or less, 2.6:1 or less, 2.5:1 or less, 2.4:1 or less, 2.3:1 or less, 2.2:1 or less, 2.1:1 or less, 2:1 or less, 1.9:1 or less, 1.8:1 or less, 1.7:1 or less, 1.6:1 or less, 1.5:1 or less, 1.4:1 or less, 1.3:1 or less, 1.2:1 or less, or 1.1:1 or less).

The molar ratio of the first borylated arene to the second borylated arene, as determined using GC-FID, can range from any of the minimum values described above to any of the maximum values described above. For example, the molar ratio of the first borylated arene to the second borylated arene, as determined using GC-FID, can range from 1:1 to 25:1 (e.g., from 1.5:1 to 25:1, from 3:1 to 25:1, from 1:1 to 10:1, from 1.5:1 to 10:1, or from 3:1 to 10:1).

Percent conversion of the substrate to the first borylated arene and the second borylated arene can vary depending on a number of factors, including the reactivity of the substrate, the identity of the ligand, and the identity of the borylation reagent. In some embodiments, percent conversion of the substrate to the first borylated arene and the second borylated arene can be at least 30% (e.g., at least 35%, at least 40%, at least 45%, at least 50%, at least 55%, at least 60%, at least 65%, at least 70%, at least 75%, at least 80%, at least 85%, at least 90%, or at least 95%).

Also provided are methods of forming borylated arenes from a substrate that comprises an aromatic ring substituted with a moiety chosen from an electron-withdrawing group and a directed metalating group, and unsubstituted in a position ortho to the moiety. The methods can comprise contacting the substrate with an iridium precursor complex, a monodentate ligand, and a borylation reagent under conditions effective to form a first borylated arene. The first borylated arene can comprise an aromatic ring substituted with a moiety chosen from an electron-withdrawing group and a directed metalating group, and a boronic acid or a boronic acid derivative in a position ortho to the moiety.

In certain embodiments, the aromatic ring can be unsubstituted in a position ortho to the moiety and unsubstituted in a position meta to the moiety. In these embodiments, the methods can comprise contacting the substrate with an iridium precursor complex, a monodentate ligand, and a borylation reagent under conditions effective to form the first borylated arene and a second borylated arene. The second borylated arene can comprise an aromatic ring substituted with a moiety chosen from an electron-withdrawing group and a directed metalating group, and a boronic acid or a boronic acid derivative in a position meta to the moiety. In some embodiments, the molar ratio of the first borylated arene to the second borylated arene is at least 1:1, as determined by GC-FID.

The substrate can be a substituted aryl compound, a substituted six-membered heteroaromatic compound, a substituted five-membered heteroaromatic compound, or a combination thereof. In some embodiments, the substrate can comprise a phenyl ring, such as those described above. In some embodiments, the substrate can comprise a pyridine ring.

As described above, the aromatic ring can be substituted with a moiety chosen from an electron-withdrawing group and a directed metalating group. In some cases, the moiety can be an electron-withdrawing group. In certain embodiments, the moiety can be an electron-withdrawing group selected from the group consisting of —F and —$CF_3$.

In some cases, the moiety can be a directed metalating group. Directed metalating groups are known in the art. See, for example, Whisler, M. C., et al., *Angew. Chem., Int. Ed.* 2004, 43, 2206-2225. In certain embodiments, the directed metalating group can be selected from the group consisting of —$OR_{13}$, —$NR_{14}R_{15}$, —C(=O)$R_{16}$, —OC(=O)$R_{16}$, a nitrile group, —$SO_2R_{16}$, —$SOR_{16}$, or a $C_1$-$C_6$ aminoalkyl group, wherein $R_{13}$, $R_{14}$, and $R_{15}$ are each, individually for each occurrence, hydrogen, a $C_1$-$C_6$ alkyl group, or an aryl group, and $R_{16}$ is, individually for each occurrence, hydrogen, —$OR_{13}$, —$NR_{14}R_{15}$, a $C_1$-$C_6$ alkyl group, or an aryl group.

In these methods, the molar ratio of the first borylated arene to the second borylated arene, as determined using GC-FID, can be at least 1:1 (e.g., at least 1.1:1, at least 1.2:1, at least 1.3:1, at least 1.4:1, at least 1.5:1, at least 1.6:1, at least 1.7:1, at least 1.8:1, at least 1.9:1, at least 2.0:1, at least 2.1:1, at least 2.2:1, at least 2.3:1, at least 2.4:1, at least 2.5:1, at least 2.6:1, at least 2.7:1, at least 2.8:1, at least 2.9:1, at least 3.0:1, at least 3.1:1, at least 3.2:1, at least 3.3:1, at least 3.4:1, at least 3.5:1, at least 3.6:1, at least 3.7:1, at least 3.8:1, at least 3.9:1, at least 4.0:1, at least 4.1:1, at least 4.2:1, at least 4.3:1, at least 4.4:1, at least 4.5:1, at least 4.6:1, at least 4.7:1, at least 4.8:1, at least 4.9:1, at least 5:1, at least 5.5:1, at least 6:1, at least 6.5:1, at least 7:1, at least 7.5:1, at least 8:1, at least 8.5:1, at least 9:1, at least 9.5:1, at least 10:1, at least 15:1, or at least 20:1). In some embodiments, the molar ratio of the first borylated arene to the second borylated arene, as determined using GC-FID, is 25:1 or less (e.g., 20:1 or less, 15:1 or less, 10:1 or less, 9.5:1 or less, 9:1 or less, 8.5:1 or less, 8:1 or less, 7.5:1 or less, 7:1 or less, 6.5:1 or less, 6:1 or less, 5.5:1 or less, 5:1 or less, 4.9:1 or less, 4.8:1 or less, 4.7:1 or less, 4.6:1 or less, 4.5:1 or less, 4.4:1 or less, 4.3:1 or less, 4.2:1 or less, 4.1:1 or less, 4:1 or less, 3.9:1 or less, 3.8:1 or less, 3.7:1 or less, 3.6:1 or less, 3.5:1 or less, 3.4:1 or less, 3.3:1 or less, 3.2:1 or less, 3.1:1 or less, 3:1 or less, 2.9:1 or less, 2.8:1 or less, 2.7:1 or less, 2.6:1 or less, 2.5:1 or less, 2.4:1 or less, 2.3:1 or less, 2.2:1or less, 2.1:1 or less, 2:1 or less, 1.9:1 or less, 1.8:1 or less, 1.7:1 or less, 1.6:1 or less, 1.5:1 or less, 1.4:1 or less, 1.3:1 or less, 1.2:1 or less, or 1.1:1 or less).

The molar ratio of the first borylated arene to the second borylated arene, as determined using GC-FID, can range from any of the minimum values described above to any of the maximum values described above. For example, the molar ratio of the first borylated arene to the second borylated arene, as determined using GC-FID, can range from 1:1 to 25:1 (e.g., from 1.5:1 to 25:1, from 3:1 to 25:1, from 1:1 to 10:1, from 1.5:1 to 10:1, or from 3:1 to 10:1).

Percent conversion of the substrate to the first borylated arene and the second borylated arene can vary depending on a number of factors, including the reactivity of the substrate, the identity of the ligand, and the identity of the borylation reagent. In some embodiments, percent conversion of the substrate to the first borylated arene and the second borylated arene can be at least 30% (e.g., at least 35%, at least 40%, at least 45%, at least 50%, at least 55%, at least 60%, at least 65%, at least 70%, at least 75%, at least 80%, at least 85%, at least 90%, or at least 95%).

Also provided are methods of forming borylated arenes from a substrate that comprise a substituted arene ring comprising from 1 to 4 substituents (e.g., from 1 to 3 substituents), wherein the arene ring is unsubstituted at a first position that is electronically favored for CH-activation and unsubstituted at a second position that is sterically favored for CH-activation. In these embodiments, methods can comprise contacting the substrate with an iridium precursor complex, a ligand chosen from a monodentate ligand and a bidentate ligand, and a borylation reagent under conditions effective to form a first borylated arene and optionally a second borylated arene. The first borylated arene can comprises a substituted arene ring comprising from 1 to 4 substituents (e.g., from 1 to 3 substituents) and a boronic acid or a boronic acid derivative in the first position. The second borylated arene, when formed, can comprise a substituted arene ring comprising from 1 to 4 substituents (e.g., from 1 to 3 substituents) and a boronic acid or a boronic acid derivative in the second position. The molar ratio of the first borylated arene to the second borylated arene can be at least 1:1, as determined by GC-FID.

In some cases, the arene ring can comprise a phenyl ring, such as those described above. In some cases, the arene ring can comprise a pyridine ring. In certain cases, the pyridine ring can comprise a 2-substituted pyridine ring. In certain cases, the pyridine ring can comprises a 2,4-disubstituted pyridine ring, a 2,6-disubstituted pyridine ring, or a 2,4,6-trisubstituted pyridine ring. The 1 to 4 substituents (e.g., the 1 to 3 substituents) present on the arene ring can individually selected from halogen, —$OR_{13}$, —$NR_{14}R_{15}$, —$C(=O)R_{16}$, —$OC(=O)R_{16}$, a nitrile group, a $C_1$-$C_6$ alkyl group, a $C_1$-$C_6$ haloalkyl group, and a $C_1$-$C_6$ aminoalkyl group, wherein $R_{13}$, $R_{14}$, and $R_{15}$ are each, individually for each occurrence, hydrogen, a $C_1$-$C_6$ alkyl group, or an aryl group, and $R_{16}$ is, individually for each occurrence, hydrogen, —$OR_{13}$, —$NR_{14}R_{15}$, a $C_1$-$C_6$ alkyl group, or an aryl group. In certain cases, the arene ring comprises an electron-withdrawing group selected from the group consisting of —F and —$CF_3$.

In these methods, the molar ratio of the first borylated arene to the second borylated arene, as determined using GC-FID, can be at least 1:1 (e.g., at least 1.1:1, at least 1.2:1, at least 1.3:1, at least 1.4:1, at least 1.5:1, at least 1.6:1, at least 1.7:1, at least 1.8:1, at least 1.9:1, at least 2.0:1, at least 2.1:1, at least 2.2:1, at least 2.3:1, at least 2.4:1, at least 2.5:1, at least 2.6:1, at least 2.7:1, at least 2.8:1, at least 2.9:1, at least 3.0:1, at least 3.1:1, at least 3.2:1, at least 3.3:1, at least 3.4:1, at least 3.5:1, at least 3.6:1, at least 3.7:1, at least 3.8:1, at least 3.9:1, at least 4.0:1, at least 4.1:1, at least 4.2:1, at least 4.3:1, at least 4.4:1, at least 4.5:1, at least 4.6:1, at least 4.7:1, at least 4.8:1, at least 4.9:1, at least 5:1, at least 5.5:1, at least 6:1, at least 6.5:1, at least 7:1, at least 7.5:1, at least 8:1, at least 8.5:1, at least 9:1, at least 9.5:1, at least 10:1, at least 15:1, or at least 20:1). In some embodiments, the molar ratio of the first borylated arene to the second borylated arene, as determined using GC-FID, is 25:1 or less (e.g., 20:1 or less, 15:1 or less, 10:1 or less, 9.5:1 or less, 9:1 or less, 8.5:1 or less, 8:1 or less, 7.5:1 or less, 7:1 or less, 6.5:1 or less, 6:1 or less, 5.5:1 or less, 5:1 or less, 4.9:1 or less, 4.8:1 or less, 4.7:1 or less, 4.6:1 or less, 4.5:1 or less, 4.4:1 or less, 4.3:1 or less, 4.2:1 or less, 4.1:1 or less, 4:1 or less, 3.9:1 or less, 3.8:1 or less, 3.7:1 or less, 3.6:1 or less, 3.5:1 or less, 3.4:1 or less, 3.3:1 or less, 3.2:1 or less, 3.1:1 or less, 3:1 or less, 2.9:1 or less, 2.8:1 or less, 2.7:1 or less, 2.6:1 or less, 2.5:1 or less, 2.4:1 or less, 2.3:1 or less, 2.2:1 or less, 2.1:1 or less, 2:1 or less, 1.9:1 or less, 1.8:1 or less, 1.7:1 or less, 1.6:1 or less, 1.5:1 or less, 1.4:1 or less, 1.3:1 or less, 1.2:1 or less, or 1.1:1 or less).

The molar ratio of the first borylated arene to the second borylated arene, as determined using GC-FID, can range from any of the minimum values described above to any of the maximum values described above. For example, the molar ratio of the first borylated arene to the second borylated arene, as determined using GC-FID, can range from 1:1 to 25:1 (e.g., from 1.5:1 to 25:1, from 3:1 to 25:1, from 1:1 to 10:1, from 1.5:1 to 10:1, or from 3:1 to 10:1).

Percent conversion of the substrate to the first borylated arene and the second borylated arene can vary depending on a number of factors, including the reactivity of the substrate, the identity of the ligand, and the identity of the borylation reagent. In some embodiments, percent conversion of the substrate to the first borylated arene and the second borylated arene can be at least 30% (e.g., at least 35%, at least 40%, at least 45%, at least 50%, at least 55%, at least 60%, at least 65%, at least 70%, at least 75%, at least 80%, at least 85%, at least 90%, or at least 95%).

The methods of forming borylated arenes described above can comprise contacting the substrate to be reacted with an iridium precursor complex, a ligand, and a borylation reagent. The substrate can be contacted with the iridium precursor complex, the ligand, and the borylation reagent in any suitable fashion, such that the substrate and the borylation reagent are present in combination with a catalytically effective amount of a catalytically active iridium complex formed by reaction of the iridium precursor complex, the ligand, and the borylation reagent. For example, the substrate can be contacted with the iridium precursor complex, the ligand, and the borylation reagent by combining in any order or fashion the substrate, the iridium precursor complex, the ligand, and the borylation reagent in a single reaction vessel or solution (e.g., by sequential or simultaneous addition of the substrate, the iridium precursor complex, the ligand, and the borylation reagent to a reaction vessel). Contacting the substrate with an iridium precursor complex, a ligand, and a borylation reagent can thus encompass methods whereby the iridium precursor complex, the ligand, and the borylation reagent or the iridium precursor complex and the ligand are combined to form a catalytically active iridium complex, which is subsequently combined with the substrate and/or the borylation reagent.

The iridium precursor complex can be any iridium complex which can react with the ligand and the borylation reagent to form a catalytically active iridium complex. The iridium precursor complex can comprise an iridium complex with three or more substituents, excluding hydrogen, bonded to the iridium. Suitable iridium precursor complexes can include one or more organic ligands, such as a cyclooctene (coe), mesitylene (MesH), cyclooctadiene (cod), 1,2,3,4,5-methylcyclopentadienyl (CP*), indenyl (Ind), or phosphine, and optionally one or more additional ligands, including monodentate ligands such as a halogen, —OMe, —OH, —OAc, or —OPh, which can be readily displaced upon combination of the iridium precursor complex with the ligand and/or borylation reagent. Suitable iridium precursor complexes can include the iridium catalysts described in U.S. Pat. No. 6,878,830 to Smith and U.S. Pat. No. 7,514,563 to Smith et al., which are hereby incorporated herein by reference in their entirety.

By way of example, the iridium precursor complex can comprise an Ir(I)-cyclooctadiene precursor complex. Suitable Ir(I)-cyclooctadiene precursor complexes are known in the art, and include [Ir(OMe)cod]$_2$, [Ir(Cl)cod]$_2$, [Ir(cod)$_2$]BF$_4$, [Ir(OH)cod]$_2$, [Ir(OPh)cod]$_2$, [Ir(OAc)cod]$_2$, (Ind)Ir(cod), Ir(acac)cod, (dtbpy)Ir(BPin)$_3$(cod), (tmp)Ir(BPin)$_3$(cod), and combinations thereof. In some embodiments, the iridium precursor complex can comprise [Ir(OMe)cod]$_2$. The iridium precursor complex can also comprise an Ir(I)-cyclooctene precursor complex, such as [Ir(OMe)coe]$_2$, [Ir(Cl)coe]$_2$, [Ir(coe)$_2$]BF$_4$, [Ir(OH)coe]$_2$, [Ir(OPh)coe]$_2$, [Ir(OAc)coe]$_2$, (Ind)Ir(coe), Ir(acac)coe, (dtbpy)Ir(BPin)$_3$(coe), (tmp)Ir(BPin)$_3$(coe), [IrCl(coe)$_2$]$_2$, and combinations thereof. The iridium precursor complex can also comprise an Ir(I)-mesitylene precursor complex. Exemplary Ir(I)-mesitylene precursor complexes can include (MesH)Ir(BPin)(B(OR$_{11}$)$_2$) and (MesH)Ir(BPin)$_3$, wherein BPin is pinacolborane and R$_{11}$ is hydrogen, a linear or branched C$_1$-C$_8$ alkyl group, an aryl group, or a C$_3$-C$_8$ cycloalkyl group. The iridium precursor complex can also comprise an Ir(I)-phosphine precursor complex. Exemplary Ir(I)-phosphine precursor complexes include (dppbz)Ir(BPin)$_3$, (Ind)Ir(dppe), (PMe$_3$)$_2$IrH$_5$, ((R$_{11}$)$_3$P)$_2$IrH$_5$, ((R$_{11}$)$_3$P)Ir(B(OR$_{11}$)$_2$)$_3$, (R$_{11}$)$_2$P)$_2$Ir(BPin)$_3$, (((R$_{11}$)$_2$P)$_3$Ir((R$_{11}$O)$_2$B)$_3$)$_2$, ((R$_{11}$)$_3$P)$_4$Ir(BPin), ((R$_{11}$)$_3$P)$_2$IrH$_x$(B(OR$_{11}$)$_2$)$_{5-x}$, and combinations thereof, wherein x is an integer between 0-4, dppbz is 1,2-bis(diphenylphosphino)benzene, BPin is pinacolborane and R$_{11}$ is hydrogen, a linear or branched C$_1$-C$_8$ alkyl group, an aryl group, or a C$_3$-C$_8$ cycloalkyl group. The iridium precursor complex can also comprise an Ir(I)-1,2,3,4,5-methylcyclopentadienyl precursor complex. Exemplary Ir(I)-1,2,3,4,5-methylcyclopentadienyl precursor complexes include (Cp*)Ir(H)$_2$(Me$_3$P), (Cp*)Ir(H)(BPin)(Me$_3$P), (CP*)Ir(H)(C$_6$H$_5$)(Me$_3$P), and combinations thereof.

Methods can involve contacting the substrate with any catalytically effective amount of the iridium precursor complex. In some cases, the substrate can be contacted with from 0.5 mole percent (mol %) to 5.0 mol % of the iridium precursor complex (e.g., from 1.0 mol % to 3.0 mol %), based on the number of moles of substrate present in the borylation reaction.

In some embodiments, the ligand can be a bidentate ligand. The bidentate ligand can comprise a bidentate ligand that includes two or more heteroatoms (e.g., nitrogen atoms) configured to chelate the iridium center. Suitable bidentate ligands can be selected in view of a number of factors, including the nature of the iridium precursor complex, the identity of the substrate, the desired regioselectivity for the borylation reaction, and the desired percent conversion of the substrate to the first borylated arene and the second borylated arene. For example, in some cases, by selecting an electron-deficient bidentate ligand, higher molar ratios of the first borylated arene to the second borylated arene can be favored. Similarly, in some cases, by selecting a bidentate ligand having low steric bulk, higher molar ratios of the first borylated arene to the second borylated arene can be favored.

Suitable bidentate ligands include heterocyclic bidentate ligands which include two or more heteroatoms (e.g., nitrogen atoms) within one or more heterocyclic rings that are configured to chelate an iridium center. Examples of heterocyclic bidentate ligands include bipyridine- and phenanthroline-based ligands.

In some embodiments, the bidentate ligand can comprise an electron-deficient bidentate ligand. Electron-deficient bidentate ligands can include, for example, heterocyclic bidentate ligands substituted with one or more electron-withdrawing moieties. Examples of electron-withdrawing moieties include halogens (e.g., F and Cl), nitriles, nitro groups, haloalkyl groups (e.g., a perfluorinated haloalkyl group such as —CF$_3$), and combinations thereof. In some embodiments, the electron-deficient bidentate ligand can comprise a bipyridine-based ligand (e.g., 2,2'-bipyridine) or a phenanthroline-based ligand (e.g., phenanthroline) substituted with one or more electron-withdrawing substituents.

In certain embodiments, the ligand can comprise a compound defined by Formula IVa, Formula IVb, or Formula IVc

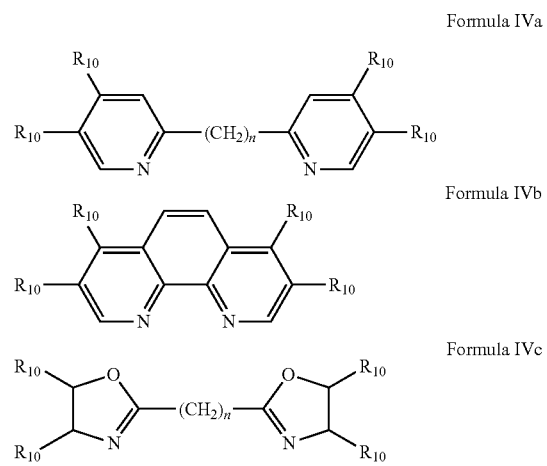

Formula IVa

Formula IVb

Formula IVc wherein n is 0, 1, 2, or 3, and R$_{10}$ is, independently for each occurrence, hydrogen, a halogen, a nitrile group, a nitro group, or a C$_1$-C$_6$ perfluoroalkyl group, with the proviso that one or more of R$_{10}$ is not hydrogen when the bidentate ligand comprises a compound defined by Formula IVa or Formula IVb. In some cases, one or more of R$_{10}$ is not hydrogen when the bidentate ligand comprises a compound defined by Formula IVa, Formula IVb, or Formula IVc. In certain embodiments, one or more of R$_{10}$ is selected from —F and —CF$_3$.

In some embodiments, the bidentate ligand can be selected from one or more of the ligands below.

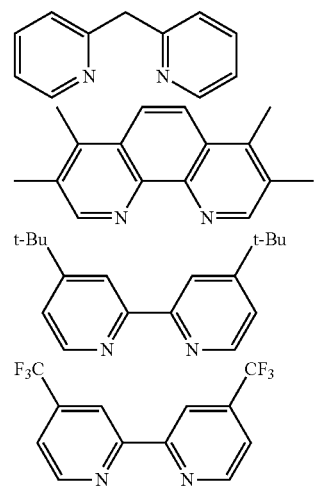

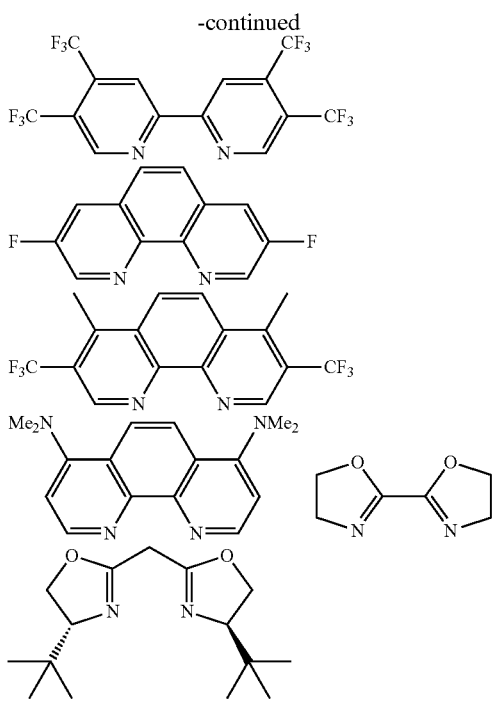

In certain embodiments, the bidentate ligand can be selected from 4,4'-bis(trifluoromethyl)-2,2'-bipyridine (btfbpy), 4,4', 5,5'-tetrakis(trifluoromethyl)-2,2'-bipyridine (ttfbpy), and 4,4',5,5'-tetrahydro-2,2'-bioxazole (box).

In some embodiments, the ligand can be a monodentate ligand. The monodentate ligand can comprise a monodentate ligand that includes a single heteroatom (e.g., a nitrogen atom) that is configured to chelate the iridium center. Suitable monodentate ligands can be selected in view of a number of factors, including the nature of the iridium precursor complex, the identity of the substrate, the desired regioselectivity for the borylation reaction, and the desired percent conversion of the substrate to the first borylated arene and the second borylated arene. For example, in some cases, by selecting a monodentate ligand that is electron-deficient, higher molar ratios of the first borylated arene to the second borylated arene can be favored. Similarly, in some cases, by selecting a monodentate ligand that is sterically hindered (e.g., that includes a substituent in a position adjacent to the heteroatom in the ring of the monodentate ligand), higher molar ratios of the first borylated arene to the second borylated arene can be favored.

In some embodiments, the monodentate ligand can comprise a pyridine ligand. In some cases, the pyridine ligand can comprise from 1 to 3 substituents. In certain cases, the pyridine ligand can comprise a 2-substituted pyridine ring. In certain cases, the pyridine ligand can comprises a 2,4-disubstituted pyridine ligand, a 2,6-disubstituted pyridine ligand, or a 2,4,6-trisubstituted pyridine ligand. The 1 to 3 substituents present on the pyridine ligand can individually selected from halogen, —OR$_{13}$, —NR$_{14}$R$_{15}$, —C(=O)R$_{16}$, —OC(=O)R$_{16}$, a nitrile group, a C$_1$-C$_6$ alkyl group, a C$_1$-C$_6$ haloalkyl group, and a C$_1$-C$_6$ aminoalkyl group, wherein R$_{13}$, R$_{14}$, and R$_{15}$ are each, individually for each occurrence, hydrogen, a C$_1$-C$_6$ alkyl group, or an aryl group, and R$_{16}$ is, individually for each occurrence, hydrogen, —OR$_{13}$, —NR$_{14}$R$_{15}$, a C$_1$-C$_6$ alkyl group, or an aryl group. In certain cases, the pyridine ligand can comprise an electron-withdrawing substituent selected from the group consisting of —F and —CF$_3$.

In some embodiments, the pyridine ligand can comprise a compound defined by the formula below

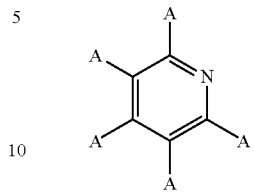

wherein
A is, independently for each occurrence, hydrogen, halogen, —OR$_{13}$, —NR$_{14}$R$_{15}$, —C(=O)R$_{16}$, —OC(=O)R$_{16}$, a nitrile group, a C$_1$-C$_6$ alkyl group, a C$_1$-C$_6$ haloalkyl group, and a C$_1$-C$_6$ aminoalkyl group, wherein R$_{13}$, R$_{14}$, and R$_{15}$ are each, individually for each occurrence, hydrogen, a C$_1$-C$_6$ alkyl group, or an aryl group, and R$_{16}$ is, individually for each occurrence, hydrogen, —OR$_{13}$, —NR$_{14}$R$_{15}$, a C$_1$-C$_6$ alkyl group, or an aryl group, with the proviso that one or more of A is not hydrogen.

In some embodiments, the pyridine ligand can comprise a compound defined by the formula below

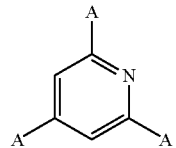

wherein
A is, independently for each occurrence, hydrogen, halogen, —OR$_{13}$, —NR$_{14}$R$_{15}$, —C(=O)R$_{16}$, —OC(=O)R$_{16}$, a nitrile group, a C$_1$-C$_6$ alkyl group, a C$_1$-C$_6$ haloalkyl group, and a C$_1$-C$_6$ aminoalkyl group, wherein R$_{13}$, R$_{14}$, and R$_{15}$ are each, individually for each occurrence, hydrogen, a C$_1$-C$_6$ alkyl group, or an aryl group, and R$_{16}$ is, individually for each occurrence, hydrogen, —OR$_{13}$, —NR$_{14}$R$_{15}$, a C$_1$-C$_6$ alkyl group, or an aryl group, with the proviso that one or more of A is not hydrogen.

In some embodiments, the pyridine ligand can comprise a compound defined by the formula below

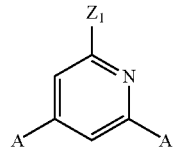

wherein
A is, independently for each occurrence, hydrogen, halogen, —OR$_{13}$, —NR$_{14}$R$_{15}$, —C(=O)R$_{16}$, —OC(=O)R$_{16}$, a nitrile group, a C$_1$-C$_6$ alkyl group, a C$_1$-C$_6$ haloalkyl group, and a C$_1$-C$_6$ aminoalkyl group, wherein R$_{13}$, R$_{14}$, and R$_{15}$ are each, individually for each occurrence, hydrogen, a C$_1$-C$_6$ alkyl group, or an aryl group, and R$_{16}$ is, individually for each occurrence, hydrogen, —OR$_{13}$, —NR$_{14}$R$_{15}$, a C$_1$-C$_6$ alkyl group, or an aryl group, and Z$_1$ is halogen, —OR$_{13}$, —NR$_{14}$R$_{15}$, —C(=O)R$_{16}$, —OC(=O)R$_{16}$, a nitrile group, a C$_1$-C$_6$ alkyl group, a C$_1$-C$_6$ haloalkyl group, and a C$_1$-C$_6$ aminoalkyl group, wherein $R_{13}$, $R_{14}$, and $R_{15}$ are each, individually for each occurrence, hydrogen, a $C_1$-$C_6$ alkyl group, or an aryl group, and $R_{16}$ is, individually for each occurrence, hydrogen, —$OR_{13}$, —$NR_{14}R_{15}$, a $C_1$-$C_6$ alkyl group, or an aryl group.

In certain embodiments, $Z_1$ is —F, —Cl, —$CF_3$, -Me, —OMe, —$CH_2NH_2$, —NHMe, —$NMe_2$, —$NPh_2$, phenyl, isopropyl, tert-butyl, or —$COCH_3$.

In some embodiments, the pyridine ligand can comprise a compound defined by the formula below

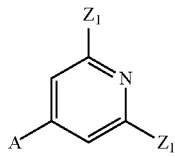

wherein

A is hydrogen, halogen, —$OR_{13}$, —$NR_{14}R_{15}$, —C(=O)$R_{16}$, —OC(=O)$R_{16}$, a nitrile group, a $C_1$-$C_6$ alkyl group, a $C_1$-$C_6$ haloalkyl group, and a $C_1$-$C_6$ aminoalkyl group, wherein $R_{13}$, $R_{14}$, and $R_{15}$ are each, individually for each occurrence, hydrogen, a $C_1$-$C_6$ alkyl group, or an aryl group, and $R_{16}$ is, individually for each occurrence, hydrogen, —$OR_{13}$, —$NR_{14}R_{15}$, a $C_1$-$C_6$ alkyl group, or an aryl group, and $Z_1$ is, independently for each occurrence, halogen, —$OR_{13}$, —$NR_{14}R_{15}$, —C(=O)$R_{16}$, —OC(=O)$R_{16}$, a nitrile group, a $C_1$-$C_6$ alkyl group, a $C_1$-$C_6$ haloalkyl group, and a $C_1$-$C_6$ aminoalkyl group, wherein $R_{13}$, $R_{14}$, and $R_{15}$ are each, individually for each occurrence, hydrogen, a $C_1$-$C_6$ alkyl group, or an aryl group, and $R_{16}$ is, individually for each occurrence, hydrogen, —$OR_{13}$, —$NR_{14}R_{15}$, a $C_1$-$C_6$ alkyl group, or an aryl group.

In certain embodiments, $Z_1$ is, independently for each occurrence, —F, —Cl, —$CF_3$, -Me, —OMe, —$CH_2NH_2$, —NHMe, —$NMe_2$, —$NPh_2$, phenyl, isopropyl, tert-butyl, or —$COCH_3$.

In some embodiments, the pyridine ligand can comprise a compound defined by the formula below

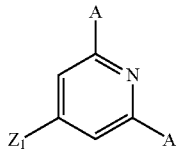

wherein

A is, independently for each occurrence, hydrogen, halogen, —$OR_{13}$, —$NR_{14}R_{15}$, —C(=O)$R_{16}$, —OC(=O)$R_{16}$, a nitrile group, a $C_1$-$C_6$ alkyl group, a $C_1$-$C_6$ haloalkyl group, and a $C_1$-$C_6$ aminoalkyl group, wherein $R_{13}$, $R_{14}$, and $R_{15}$ are each, individually for each occurrence, hydrogen, a $C_1$-$C_6$ alkyl group, or an aryl group, and $R_{16}$ is, individually for each occurrence, hydrogen, —$OR_{13}$, —$NR_{14}R_{15}$, a $C_1$-$C_6$ alkyl group, or an aryl group, and $Z_1$ is halogen, —$OR_{13}$, —$NR_{14}R_{15}$, —C(=O)$R_{16}$, —OC(=O)$R_{16}$, a nitrile group, a $C_1$-$C_6$ alkyl group, a $C_1$-$C_6$ haloalkyl group, and a $C_1$-$C_6$ aminoalkyl group, wherein $R_{13}$, $R_{14}$, and $R_{15}$ are each, individually for each occurrence, hydrogen, a $C_1$-$C_6$ alkyl group, or an aryl group, and $R_{16}$ is, individually for each occurrence, hydrogen, —$OR_{13}$, —$NR_{14}R_{15}$, a $C_1$-$C_6$ alkyl group, or an aryl group.

In certain embodiments, $Z_1$ is —F, —Cl, —$CF_3$, -Me, —OMe, —$CH_2NH_2$, —NHMe, —$NMe_2$, —$NPh_2$, phenyl, isopropyl, tert-butyl, or —$COCH_3$.

In some embodiments, the pyridine ligand can comprise a compound defined by the formula below

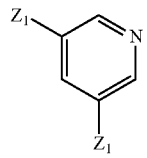

wherein $Z_1$ is, independently for each occurrence, halogen, —$OR_{13}$, —$NR_{14}R_{15}$, —C(=O)$R_{16}$, —OC(=O)$R_{16}$, a nitrile group, a $C_1$-$C_6$ alkyl group, a $C_1$-$C_6$ haloalkyl group, and a $C_1$-$C_6$ aminoalkyl group, wherein $R_{13}$, $R_{14}$, and $R_{15}$ are each, individually for each occurrence, hydrogen, a $C_1$-$C_6$ alkyl group, or an aryl group, and $R_{16}$ is, individually for each occurrence, hydrogen, —$OR_{13}$, —$NR_{14}R_{15}$, a $C_1$-$C_6$ alkyl group, or an aryl group.

In certain embodiments, $Z_1$ is, independently for each occurrence, —F, —Cl, —$CF_3$, -Me, —OMe, —$CH_2NH_2$, —NHMe, —$NMe_2$, —$NPh_2$, phenyl, isopropyl, tert-butyl, or —$COCH_3$.

In some embodiments, the ligand can be present in the borylation reaction in an amount ranging from 0.5 molar equivalents of ligand per mole of iridium present in the borylation reaction to 5 molar equivalents of ligand per mole of iridium present in the borylation reaction (e.g., from 1 molar equivalents of ligand per mole of iridium present in the borylation reaction to 3 molar equivalents of ligand per mole of iridium present in the borylation reaction).

The borylation reagent can be any suitable HB or B—B organic compound known in the art as a borylation reagent. Suitable borylation reagents can be selected in view of a variety of factors, including considerations regarding the reactivity of the resulting borylated arenes. Exemplary borylation reagents include the HB or B—B organic compounds shown below.

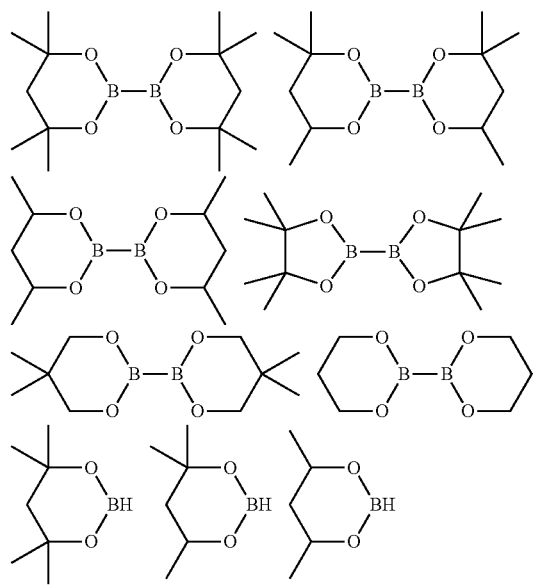

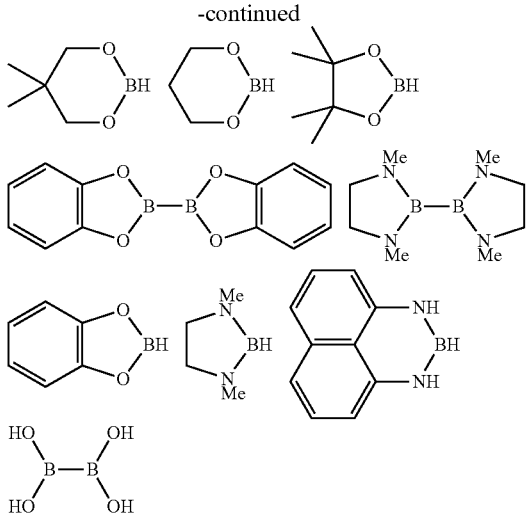

In some embodiments, the borylation reagent is selected from pinacolborane (HBPin), catecholborane, bis(neopentyl glycolato)diboron, bis(pinacolato)diboron ($B_2Pin_2$), bis(hexylene glycolato)diboron, and bis(catecholato)diboron. In certain embodiments, the borylation reagent is pinacolborane (HBPin) or bis(pinacolato)diboron ($B_2Pin_2$).

The borylation reagent can be incorporated in the borylation reaction in any suitable amount. For example, in some embodiments, the borylation reagent can be present in the borylation reaction in an amount ranging from 1 molar equivalent of borylation reagent per mole of substrate present in the borylation reaction to 5 molar equivalents of borylation reagent per mole of substrate present in the borylation reaction (e.g., from 1 molar equivalent of borylation reagent per mole of substrate present in the borylation reaction to 3 molar equivalents of borylation reagent per mole of substrate present in the borylation reaction).

In some embodiments, the methods provided herein can provide for the regioselective borylation of substrates. As described above, the substrate can comprise a substituted arene ring comprising from 1 to 4 substituents (e.g., from 1 to 3 substituents), such as a phenyl ring which is substituted with an electron-withdrawing group selected from the group consisting of —F and —$CF_3$, and which is unsubstituted in a position ortho to the electron-withdrawing group and unsubstituted in a position meta to the electron-withdrawing group. Regioselective borylation methods are borylation methods which can afford borylation of the substrate at a position ortho to the electron-withdrawing group and form the first borylated arene (the electronic product), while not affording a significant amount of borylation of the substrate at a position meta to the electron-withdrawing group and forming the second borylated arene (the steric product). Borylation methods can be said to be regioselective when the molar ratio of the first borylated arene to the second borylated arene formed by the method, as determined using GC-FID, is at least 25:1 (e.g., at least 50:1, at least 75:1, or at least 100:1). In some embodiments, regioselective borylation methods can produce no detectable amount of the second borylated arene (the steric product). Such regioselective methods can be described as forming exclusively the electronic borylation product (the first borylated arene).

In some embodiments, regioselective borylation methods can comprise tandem borylation/dehalogenation. For example, methods for the regioselective borylation of arenes can comprise contacting a suitable substrate with an iridium precursor complex, a ligand chosen from a monodentate ligand and a bidentate ligand, and a borylation reagent under conditions effective to form a first borylated arene and optionally a second borylated arene, wherein the molar ratio of the first borylated arene to the second borylated arene, as determined using GC-FID is at least 25:1.

The substrate can comprise, for example, a phenyl ring which is substituted with an electron-withdrawing group selected from the group consisting of —F and —$CF_3$, which is unsubstituted in a position ortho to the electron-withdrawing group, and which further includes a sacrificial moiety (e.g., a halogen such as Cl or Br) positioned so as to sterically hinder attack of the iridium catalyst at the otherwise sterically favored position meta to the electron-withdrawing group (e.g., a Cl or Br substituent para to the electron-withdrawing group). As a result, iridium-catalyzed C—H activation-borylation of the arene exclusively generates the ortho-borylated electronic product (i.e., the first borylated arene).

For example, in some embodiments, the substrate can comprise a compound defined by Formula I

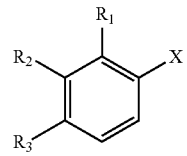

Formula I wherein

X is F or $CF_3$;

$R_1$ is hydrogen, a halogen, —$OR_4$, —$NR_5R_6$, —C(=O)$R_7$, a nitrile group, a $C_1$-$C_6$ alkyl group, or a $C_1$-$C_6$ haloalkyl group;

$R_2$ is hydrogen, a halogen, —$OR_4$, —$NR_5R_6$, —C(=O)$R_7$, a nitrile group, a $C_1$-$C_6$ alkyl group, or a $C_1$-$C_6$ haloalkyl group;

$R_3$ is Cl or Br;

$R_4$, $R_5$, and $R_6$ are each, individually for each occurrence, hydrogen or a $C_1$-$C_6$ alkyl group; and $R_7$ is, individually for each occurrence, hydrogen, —$OR_4$, —$NR_5R_6$, or a $C_1$-$C_6$ alkyl group.

In these embodiments, the first borylated arene can comprise a compound defined by Formula II

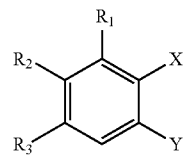

Formula II wherein X, $R_1$, $R_2$, and $R_3$ are as described above, and Y is a boronic acid or a boronic acid derivative.

Methods can further comprise reductively dehalogenating the first borylated arene to obtain a dehalogenated borylated arene. The dehalogenated borylated arene can comprise a compound defined by Formula IIb

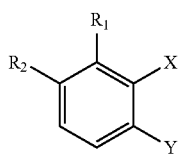

Formula IIb wherein X, $R_1$, $R_2$, and Y are as described above.

The first borylated arene can be reductively dehalogenated using any suitable synthetic method. For example, methods for reductively dehalogenating the first borylated arene can comprise contacting the first borylated arene with polymethylhydrosiloxane (PMHS), a base, and a metal catalyst under conditions effective to reductively dehalogenate the first borylated arene. Suitable bases include KF and tetraalkylammonium salts, such as TBAF. The metal catalyst can comprise a variety of metal catalysts which can accept a hydride from PMHS, and subsequently participate in the reductive dehalogenation of the first borylated arene. Suitable metal catalysts can be selected in view of a number of factors, including the identity of the first borylated arene (e.g., the identity of the halogen being hydrodehalogenated). For example, the metal catalyst can comprise Pd, Sn, Ti, Zn, or Cu. In certain embodiments, the metal catalyst can comprise a palladium(II) catalyst, such as palladium(II) acetate (Pd(OAc)$_2$), or a palladium(0) catalyst, such as tetrakis(triphenylphosphine)palladium(0) (Pd(Ph$_3$P)$_4$).

In certain embodiments, the methods for reductively dehalogenating the first borylated arene can comprise contacting the first borylated arene with a formate salt and a transition metal catalyst under conditions effective to reductively dehalogenate the first borylated arene. The formate salt can be any suitable formate salt. Examples of formate salts include, for example, sodium formate (NaHC(O)O), potassium formate (KHC(O)O), ammonium formate (NH$_4$HC(O)O), calcium formate (Ca(HC(O)O)$_2$), and combinations thereof. In certain cases, the formate salt can be ammonium formate. The transition metal catalyst can comprise a palladium(0) catalyst, such as palladium on carbon. In certain embodiments, the borylation and dehalogenation described above can be performed using a one-pot synthetic methodology (e.g., without purification or isolation of the intermediate borylate, such as sequentially in a single reaction vessel).

Borylated arenes prepared using the methods described herein can be utilized in additional chemical reactions, including cross-coupling reactions, such as Suzuki-type cross-coupling reactions. Suzuki-type cross-coupling reactions are known in the art, and can be used to cross-couple an organohalide and an organoborane in the presence of a base and a suitable catalyst. See, for example, Miyaura, N. and Suzuki, A. Chem. Rev. 1995, 95, 2457; Stanforth, S. P. Tetrahedron 1998, 54, 263; Lipshutz, et al., Synthesis 2005, 2989; and Lipshutz, et al., Org. Lett. 2008, 10, 4279. The organohalide can be an unsaturated halide or pseudohalide (e.g., a triflate (OTf)), such as an aryl halide or pseudohalide or vinyl halide or pseudohalide.

In some embodiments, the methods described herein can further comprise contacting the first borylated arene or the dehalogenated borylated arene with a reactant selected from the group consisting of an aryl halide, an aryl pseudohalide, a vinyl halide, and an vinyl pseudohalide, and a transition metal catalyst to cross-couple the reactant and the first borylated arene or the dehalogenated borylated arene. By way of example, a (4-chloro-2-fluoro-3-substituted)boronic acid ester can undergo a cross-coupling reaction with methyl 4-acetamido-3,6-dichloropicolinate to produce or form a 6-(4-chloro-2-fluoro-3-substituted-phenyl)-4-aminopicolinate. In another example, a (4-chloro-2-fluoro-3-substituted) boronic acid ester can undergo a cross-coupling reaction with methyl 6-acetamido-2-chloropyrimidine-4-carboxylate, or its unprotected analog the 6-amino-2-chloropyrimidine-4-carboxylic acid.

The Suzuki cross-coupling reaction can occur in the presence of a palladium catalyst, a ligand, and a base. In at least some embodiments, the palladium catalyst is palladium (II)acetate (Pd(OAc)$_2$), the base is aqueous potassium carbonate (K$_2$CO$_3$), and the ligand is triphenylphosphine (PPh$_3$). The cross-coupling reaction can be conducted in a solvent such as methyl isobutyl ketone (MIBK), acetonitrile (MeCN), ethyl acetate (EtOAc), water, or combinations thereof.

Also provided are catalytic iridium complexes that can catalyze the borylation of arenes that are substituted with an electron-withdrawing group, including 1-chloro-3-fluoro-2-substituted benzenes, at positions ortho to the fluoro substituent (i.e., they can effectively catalyze formation of the electronic product). Catalytic iridium complexes can be formed by combination of the iridium precursor complex, the bidentate ligand, and the borylation reagent. In some cases, catalytic iridium complexes are formed in situ in the presence of the substrate during practice of the methods described herein. Catalytic iridium complexes can also be formed by contacting the iridium precursor complex with the bidentate ligand and the borylation reagent. Once formed, the catalytic iridium complex can subsequently be combined with the substrate and/or the borylation reagent to afford the borylated substrate.

In some embodiments, the catalytic iridium complex can be defined by the structure below (L)Ir(B)$_3$(Z$_2$)

wherein

B is —B(OR)$_2$, wherein R is, independently for each occurrence, a $C_1$-$C_6$ alkyl group, or wherein the two R groups, taken together with the atoms to which they are attached, form a $C_2$-$C_6$ cyclic moiety, optionally substituted with one or more $C_1$-$C_6$ alkyl groups, and optionally fused with one or more carbocyclyl or heterocarbocyclyl groups;

$Z_2$ is 1,5-cyclooctadiene, cyclooctene, or mesitylene; and

L is a bidentate ligand selected from one of the ligands included below.

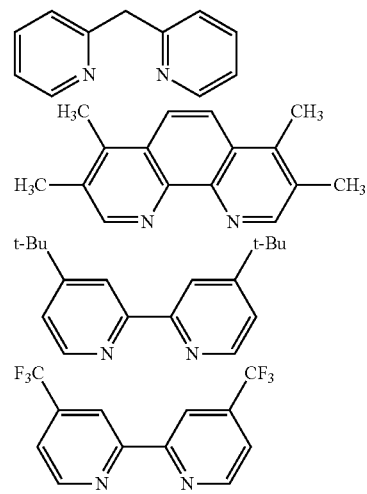

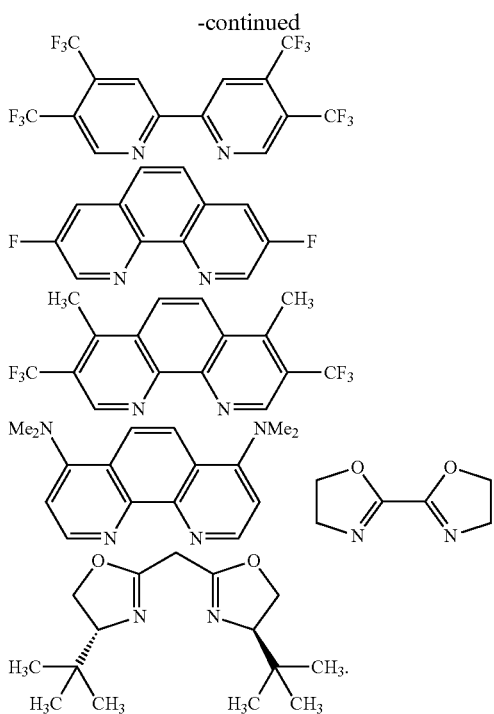

In some of these embodiments, the catalytic iridium complex can include a bidentate ligand selected from one of the ligands included below.

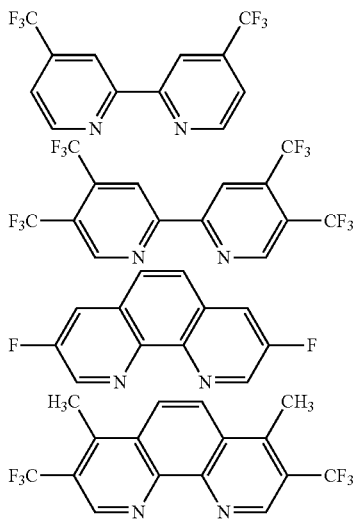

In some embodiments, each B is independently selected from one of the boron-containing moieties included below.

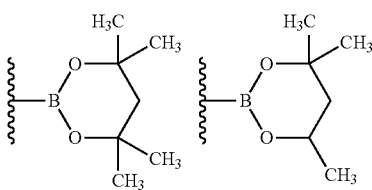

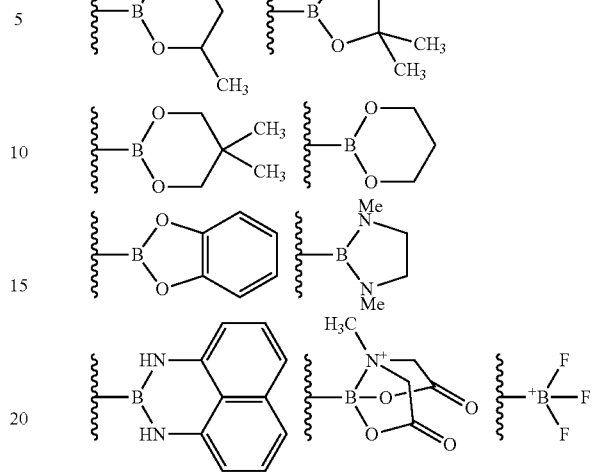

In certain embodiments, one or more of B represents pinacolborane. In some cases, each B represents pinacolborane.

In certain embodiments, the catalytic iridium complex can be defined by the structure below $$(L)Ir(B)_3(Z_2)$$

wherein

B is —B(OR)$_2$, wherein R is, independently for each occurrence, a $C_1$-$C_6$ alkyl group, or wherein the two R groups, taken together with the atoms to which they are attached, form a $C_2$-$C_6$ cyclic moiety, optionally substituted with one or more $C_1$-$C_6$ alkyl groups, and optionally fused with one or more carbocyclyl or heterocarbocyclyl groups;

$Z_2$ is 1,5-cyclooctadiene, cyclooctene, or mesitylene; and

L is a bidentate ligand defined by Formula IVa, Formula IVb, or Formula IVc

Formula IVa
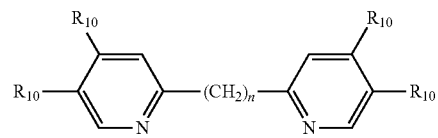

Formula IVb
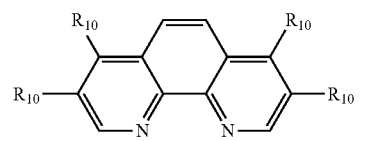

Formula IVc
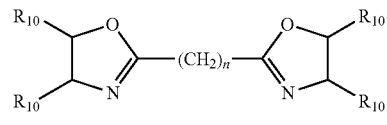

wherein n is 0, 1, 2, or 3 and $R_{10}$ is, independently for each occurrence, hydrogen, a halogen, a nitrile group, a nitro group, a $C_1$-$C_6$ alkyl group, or a $C_1$-$C_6$ perfluoroalkyl group, with the proviso that one or more of $R_{10}$ is not hydrogen when the bidentate ligand comprises a compound defined by Formula IVa or Formula IVb.

In some of these embodiments, the catalytic iridium complex can include a bidentate ligand selected from one of the ligands included below.

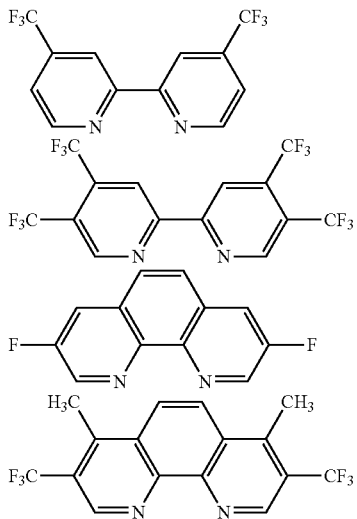

In some embodiments, each B is independently selected from one of the boron-containing moieties included below.

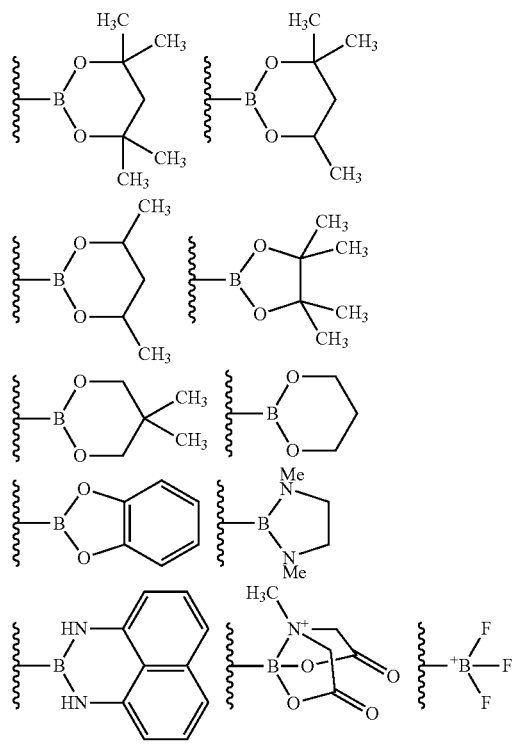

In certain embodiments, one or more of B represents pinacolborane. In some cases, each B represents pinacolborane.

Example Embodiments

Specific embodiments of the present disclosure are provided below.

1. A method of forming a borylated arene comprising:
   providing a substrate comprising a phenyl ring substituted with an electron-withdrawing group selected from the group consisting of —F and —CF$_3$, wherein the phenyl ring is unsubstituted in a position ortho to the electron-withdrawing group and unsubstituted in a position meta to the electron-withdrawing group; and
   contacting the substrate with an iridium precursor complex, a ligand chosen from a monodentate ligand and a bidentate ligand, and a borylation reagent under conditions effective to form a first borylated arene and optionally a second borylated arene;
   wherein the first borylated arene comprises a phenyl ring substituted with an electron-withdrawing group selected from the group consisting of —F and —CF$_3$, and a boronic acid or a boronic acid derivative in a position ortho to the electron-withdrawing group,
   wherein the second borylated arene, when formed, comprises a phenyl ring substituted with an electron-withdrawing group selected from the group consisting of —F and —CF$_3$, and a boronic acid or a boronic acid derivative in a position meta to the electron-withdrawing group, and
   wherein the molar ratio of the first borylated arene to the second borylated arene is at least 1:1, as determined by GC-FID.

2. The method of embodiment 1, wherein the substrate comprises a compound defined by Formula I

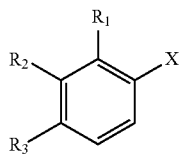

Formula I wherein
X is F or CF$_3$;
R$_1$ is hydrogen, a halogen, —OR$_4$, —NR$_5$R$_6$, —C(=O)R$_7$, a nitrile group, a C$_1$-C$_6$ alkyl group, or a C$_1$-C$_6$ haloalkyl group;
R$_2$ is hydrogen, a halogen, —OR$_4$, —NR$_5$R$_6$, —C(=O)R$_7$, a nitrile group, a C$_1$-C$_6$ alkyl group, or a C$_1$-C$_6$ haloalkyl group;
R$_3$ is hydrogen, a halogen, —OR$_4$, —NR$_5$R$_6$, —C(=O)R$_7$, a nitrile group, a C$_1$-C$_6$ alkyl group, or a C$_1$-C$_6$ haloalkyl group;
R$_4$, R$_5$, and R$_6$ are each, individually for each occurrence, hydrogen or a C$_1$-C$_6$ alkyl group; and
R$_7$ is, individually for each occurrence, hydrogen, —OR$_4$, —NR$_5$R$_6$, or a C$_1$-C$_6$ alkyl group;
the first borylated arene comprises a compound defined by Formula II

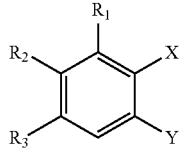

Formula II wherein
X, R$_1$, R$_2$, and R$_3$ are as described above, and Y is a boronic acid or a boronic acid derivative; and
the second borylated arene, when formed, comprises a compound defined by Formula III

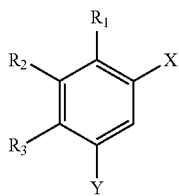

Formula III wherein
X, $R_1$, $R_2$, and $R_3$ are as described above, and Y is a boronic acid or a boronic acid derivative.
3. The method of embodiment 1 or 2, wherein first borylated arene comprises a boronic acid derivative in a position ortho to the electron-withdrawing group which is selected from one of the following:

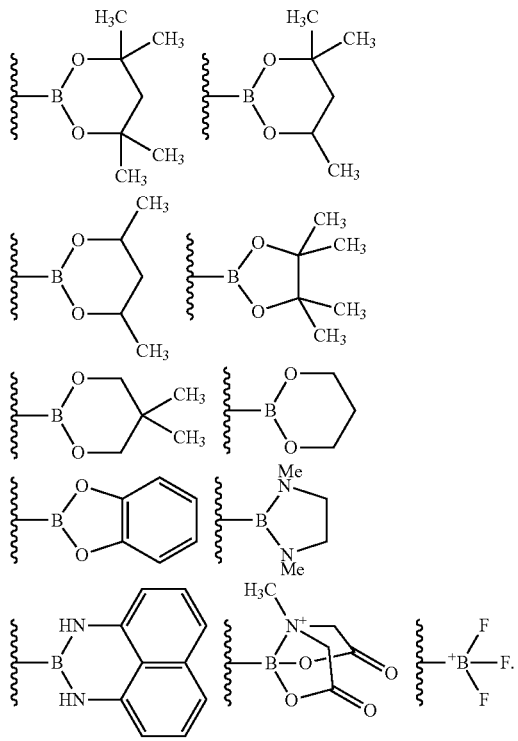

4. The method of any of embodiments 1-3, wherein the substrate comprises a 1-chloro-3-fluoro-2-substituted benzene.
5. The method of any of embodiments 1-4, wherein the substrate comprises 1-chloro-3-fluoro-2-methoxybenzene.
6. The method of any of embodiments 1-5, wherein the first borylated arene comprises (4-chloro-2-fluoro-3-methoxyphenyl)boronic acid or a (4-chloro-2-fluoro-3-methoxyphenyl)-boronic acid derivative.
7. The method of any of embodiments 1-6, wherein the molar ratio of the first borylated arene to the second borylated arene is at least 3:1.
8. The method of any of embodiments 1-7, wherein percent conversion to the first borylated arene and the second borylated arene is at least 30%.
9. The method of any of embodiments 1-8, wherein percent conversion to the first borylated arene and the second borylated arene is at least 50%.

10. The method of any of embodiments 1-9, wherein the iridium precursor complex comprises an Ir(I)-cyclooctadiene precursor complex.
11. The method of embodiment 10, wherein the Ir(I)-cyclooctadiene precursor complex is selected from the group consisting of [Ir(OMe)cod]$_2$, [Ir(Cl)cod]$_2$, [Ir(cod)$_2$]BF$_4$, [Ir(OH)cod]$_2$, [Ir(OPh)cod]$_2$, [Ir(OAc)cod]$_2$, (Ind)Ir(cod), Ir(acac)cod, (dtbpy)Ir(BPin)$_3$(cod), (tmp)Ir(BPin)$_3$(cod), and combinations thereof.
12. The method of any one of embodiments 1-9, wherein the iridium precursor complex comprises an Ir(I)-cyclooctene precursor complex.
13. The method of embodiment 12, wherein the Ir(I)-cyclooctene precursor complex is selected from the group consisting of [Ir(OMe)coe]$_2$, [Ir(Cl)coe]$_2$, [Ir(coe)$_2$]BF$_4$, [Ir(OH)coe]$_2$, [Ir(OPh)coe]$_2$, [Ir(OAc)coe]$_2$, (Ind)Ir(coe), Ir(acac)coe, (dtbpy)Ir(BPin)$_3$(coe), (tmp)Ir(BPin)$_3$(coe), [IrCl(coe)$_2$]$_2$, and combinations thereof.
14. The method of any one of embodiments 1-9, wherein the iridium precursor complex comprises an Ir(I)-mesitylene precursor complex.
15. The method of embodiment 14, wherein the Ir(I)-mesitylene precursor complex is selected from the group consisting of (MesH)Ir(BPin)(B(OR$_{11}$)$_2$), (MesH)Ir(BPin)$_3$, and combinations thereof, wherein BPin is pinacolborane, and $R_{11}$ is hydrogen, a linear or branched $C_1$-$C_8$ alkyl group, an aryl group, or a $C_3$-$C_8$ cycloalkyl group.
16. The method of any of embodiments 1-9, wherein the iridium precursor complex comprises an Ir(I)-phosphine precursor complex.
17. The method of embodiment 16, wherein the Ir(I)-phosphine precursor complex is selected from the group consisting of (dppbz)Ir(BPin)$_3$, (Ind)Ir(dppe), (PMe$_3$)$_2$IrH$_5$, ((R$_{11}$)$_3$P)$_2$IrH$_5$, ((R$_{11}$)$_3$P)$_3$Ir(B(OR$_{11}$)$_2$)$_3$, (R$_{11}$)$_2$P)$_2$Ir(BPin)$_3$, (((R$_{11}$)$_2$P)$_3$Ir(R$_{11}$O)$_2$B)$_3$)$_2$, ((R$_{11}$)$_3$P)$_4$Ir(BPin), ((R$_{11}$)$_3$P)$_2$IrH$_x$(B(OR$_{11}$)$_2$)$_{5-x}$, and combinations thereof, wherein x is an integer between 0-4, dppbz is 1,2-bis(diphenylphosphino)benzene, BPin is pinacolborane, and $R_{11}$ is hydrogen, a linear or branched $C_1$-$C_8$ alkyl group, an aryl group, or a $C_3$-$C_8$ cycloalkyl group.
18. The method of any of embodiments 1-9, wherein the iridium precursor complex comprises an Ir(I)-1,2,3,4,5-methylcyclopentadienyl precursor complex.
19. The method of embodiment 18, wherein the Ir(I)-1,2,3,4,5-methylcyclopentadienyl precursor complex is selected from the group consisting of (Cp*)Ir(H)$_2$(Me$_3$P), (Cp*)Ir(H)(BPin)(Me$_3$P), (Cp*)Ir(H)(C$_6$H$_5$)(Me$_3$P), and combinations thereof.
20. The method of any of embodiments 1-19, wherein the ligand comprises a bidentate ligand.
21. The method of embodiment 20, wherein the bidentate ligand comprises an electron-deficient bidentate ligand.
22. The method of embodiment 20 or 21, wherein the bidentate ligand comprises 2,2'-bipyridine substituted with one or more electron-withdrawing substituents.
23. The method of any of embodiments 20-22, wherein the bidentate ligand comprises 2,2'-bipyridine substituted with one or more trifluoromethyl groups.
24. The method of any of embodiments 20-23, wherein the bidentate ligand comprises a compound defined by Formula IVa, Formula IVb, or Formula IVc Formula IVa

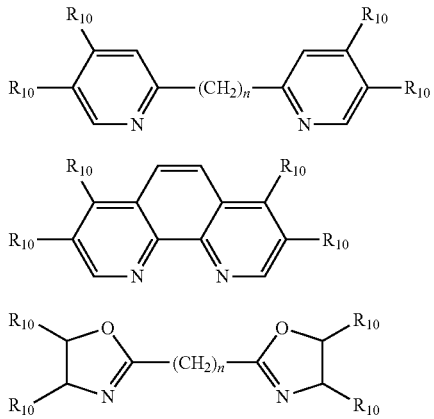

Formula IVb

Formula IVc wherein n is 0, 1, 2, or 3 and $R_{10}$ is, independently for each occurrence, hydrogen, a halogen, a nitrile group, a nitro group, a $C_1$-$C_6$ alkyl group, or a $C_1$-$C_6$ perfluoroalkyl group, with the proviso that one or more of $R_{10}$ is not hydrogen when the bidentate ligand comprises a compound defined by Formula IVa or Formula IVb.

25. The method of embodiment 24, wherein one or more of $R_{10}$ is selected from —F and —$CF_3$.

26. The method of any of embodiments 20-25, wherein the bidentate ligand is selected from one or more of the following:

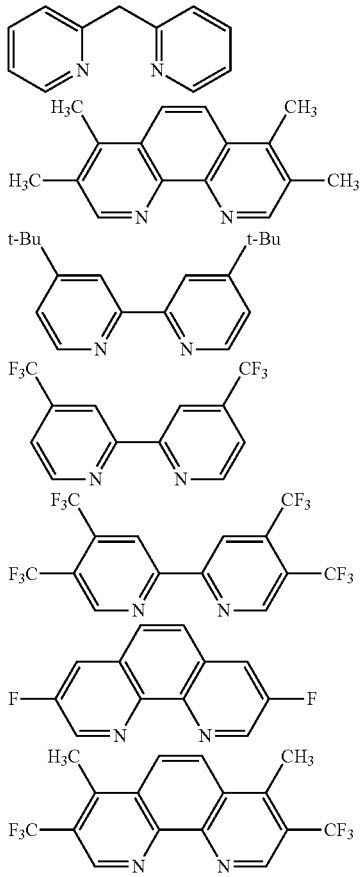

27. The method of any of embodiments 1-19, wherein the ligand comprises a monodentate ligand.

28. The method of embodiment 27, wherein the monodentate ligand comprises a pyridine ligand.

29. The method of embodiment 28, wherein the pyridine ligand comprises pyridine defined by the formula below wherein A is, independently for each occurrence, hydrogen, halogen, —$OR_{13}$, —$NR_{14}R_{15}$, —C(=O)$R_{16}$, —OC(=O)$R_{16}$, a nitrile group, a $C_1$-$C_6$ alkyl group, a $C_1$-$C_6$ haloalkyl group, and a $C_1$-$C_6$ aminoalkyl group, wherein $R_{13}$, $R_{14}$, and $R_{15}$ are each, individually for each occurrence, hydrogen, a $C_1$-$C_6$ alkyl group, or an aryl group, and $R_{16}$ is, individually for each occurrence, hydrogen, —$OR_{13}$, —$NR_{14}R_{15}$, a $C_1$-$C_6$ alkyl group, or an aryl group, with the proviso that one or more of A is not hydrogen.

30. The method of embodiment 28 or 29, wherein the pyridine ligand comprises pyridine defined by the formula below wherein A is, independently for each occurrence, hydrogen, halogen, —$OR_{13}$, —$NR_{14}R_{15}$, —C(=O)$R_{16}$, —OC(=O)$R_{16}$, a nitrile group, a $C_1$-$C_6$ alkyl group, a $C_1$-$C_6$ haloalkyl group, and a $C_1$-$C_6$ aminoalkyl group, wherein $R_{13}$, $R_{14}$, and $R_{15}$ are each, individually for each occurrence, hydrogen, a $C_1$-$C_6$ alkyl group, or an aryl group, and $R_{16}$ is, individually for each occurrence, hydrogen, —$OR_{13}$, —$NR_{14}R_{15}$, a $C_1$-$C_6$ alkyl group, or an aryl group, with the proviso that one or more of A is not hydrogen.

31. The method of any of embodiments 28-30, wherein the pyridine ligand comprises pyridine defined by the formula below

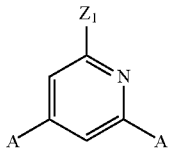

wherein A is, independently for each occurrence, hydrogen, halogen, —$OR_{13}$, —$NR_{14}R_{15}$, —C(=O)$R_{16}$, —OC(=O)$R_{16}$, a nitrile group, a $C_1$-$C_6$ alkyl group, a $C_1$-$C_6$ haloalkyl group, and a $C_1$-$C_6$ aminoalkyl group, wherein $R_{13}$, $R_{14}$, and $R_{15}$ are each, individually for each occurrence, hydrogen, a $C_1$-$C_6$ alkyl group, or an aryl group, and $R_{16}$ is, individually for each occurrence, hydrogen, —$OR_{13}$, —$NR_{14}R_{15}$, a $C_1$-$C_6$ alkyl group, or an aryl group, and $Z_1$ is halogen, —$OR_{13}$, —$NR_{14}R_{15}$, —C(=O)$R_{16}$, —OC(=O)$R_{16}$, a nitrile group, a $C_1$-$C_6$ alkyl group, a $C_1$-$C_6$ haloalkyl group, and a $C_1$-$C_6$ aminoalkyl group, wherein $R_{13}$, $R_{14}$, and $R_{15}$ are each, individually for each occurrence, hydrogen, a $C_1$-$C_6$ alkyl group, or an aryl group, and $R_{16}$ is, individually for each occurrence, hydrogen, —$OR_{13}$, —$NR_{14}R_{15}$, a $C_1$-$C_6$ alkyl group, or an aryl group.

32. The method of any of embodiments 28-31, wherein the pyridine ligand comprises pyridine defined by the formula below

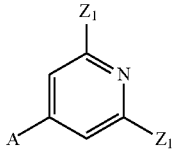

wherein A is hydrogen, halogen, —$OR_{13}$, —$NR_{14}R_{15}$, —C(=O)$R_{16}$, —OC(=O)$R_{16}$, a nitrile group, a $C_1$-$C_6$ alkyl group, a $C_1$-$C_6$ haloalkyl group, and a $C_1$-$C_6$ aminoalkyl group, wherein $R_{13}$, $R_{14}$, and $R_{15}$ are each, individually for each occurrence, hydrogen, a $C_1$-$C_6$ alkyl group, or an aryl group, and $R_{16}$ is, individually for each occurrence, hydrogen, —$OR_{13}$, —$NR_{14}R_{15}$, a $C_1$-$C_6$ alkyl group, or an aryl group, and $Z_1$ is, independently for each occurrence, halogen, —$OR_{13}$, —$NR_{14}R_{15}$, —C(=O)$R_{16}$, —OC(=O)$R_{16}$, a nitrile group, a $C_1$-$C_6$ alkyl group, a $C_1$-$C_6$ haloalkyl group, and a $C_1$-$C_6$ aminoalkyl group, wherein $R_{13}$, $R_{14}$, and $R_{15}$ are each, individually for each occurrence, hydrogen, a $C_1$-$C_6$ alkyl group, or an aryl group, and $R_{16}$ is, individually for each occurrence, hydrogen, —$OR_{13}$, —$NR_{14}R_{15}$, a $C_1$-$C_6$ alkyl group, or an aryl group.

33. The method of any of embodiments 28-30, wherein the pyridine ligand comprises pyridine defined by the formula below

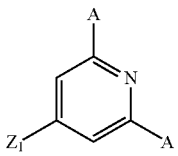

wherein A is, independently for each occurrence, hydrogen, halogen, —$OR_{13}$, —$NR_{14}R_{15}$, —C(=O)$R_{16}$, —OC(=O)$R_{16}$, a nitrile group, a $C_1$-$C_6$ alkyl group, a $C_1$-$C_6$ haloalkyl group, and a $C_1$-$C_6$ aminoalkyl group, wherein $R_{13}$, $R_{14}$, and $R_{15}$ are each, individually for each occurrence, hydrogen, a $C_1$-$C_6$ alkyl group, or an aryl group, and $R_{16}$ is, individually for each occurrence, hydrogen, —$OR_{13}$, —$NR_{14}R_{15}$, a $C_1$-$C_6$ alkyl group, or an aryl group, and $Z_1$ is halogen, —$OR_{13}$, —$NR_{14}R_{15}$, —C(=O)$R_{16}$, —OC(=O)$R_{16}$, a nitrile group, a $C_1$-$C_6$ alkyl group, a $C_1$-$C_6$ haloalkyl group, and a $C_1$-$C_6$ aminoalkyl group, wherein $R_{13}$, $R_{14}$, and $R_{15}$ are each, individually for each occurrence, hydrogen, a $C_1$-$C_6$ alkyl group, or an aryl group, and $R_{16}$ is, individually for each occurrence, hydrogen, —$OR_{13}$, —$NR_{14}R_{15}$, a $C_1$-$C_6$ alkyl group, or an aryl group.

34. The method of embodiment 28 or 29, wherein the pyridine ligand comprises pyridine defined by the formula below

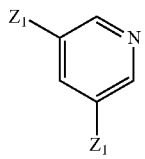

wherein $Z_1$ is, independently for each occurrence, halogen, —$OR_{13}$, —$NR_{14}R_{15}$, —C(=O)$R_{16}$, —OC(=O)$R_{16}$, a nitrile group, a $C_1$-$C_6$ alkyl group, a $C_1$-$C_6$ haloalkyl group, and a $C_1$-$C_6$ aminoalkyl group, wherein $R_{13}$, $R_{14}$, and $R_{15}$ are each, individually for each occurrence, hydrogen, a $C_1$-$C_6$ alkyl group, or an aryl group, and $R_{16}$ is, individually for each occurrence, hydrogen, —$OR_{13}$, —$NR_{14}R_{15}$, a $C_1$-$C_6$ alkyl group, or an aryl group.

35. The method of any of embodiments 29-34, wherein $Z_1$ is, independently for each occurrence, —F, —Cl, —$CF_3$, -Me, —OMe, —$CH_2NH_2$, —NHMe, —$NMe_2$, —$NPh_2$, phenyl, isopropyl, tert-butyl, or —$COCH_3$.

36. The method of any of embodiments 1-35, wherein the borylation reagent is selected from one or more of the following:

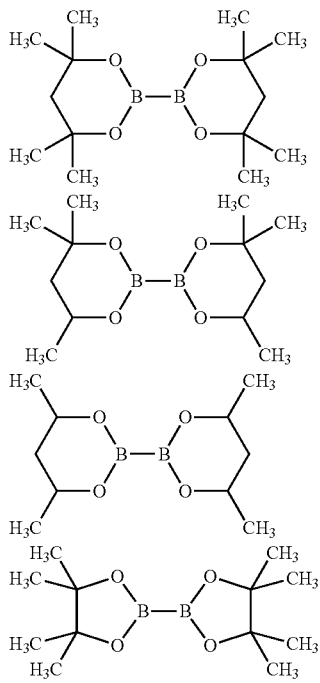

-continued

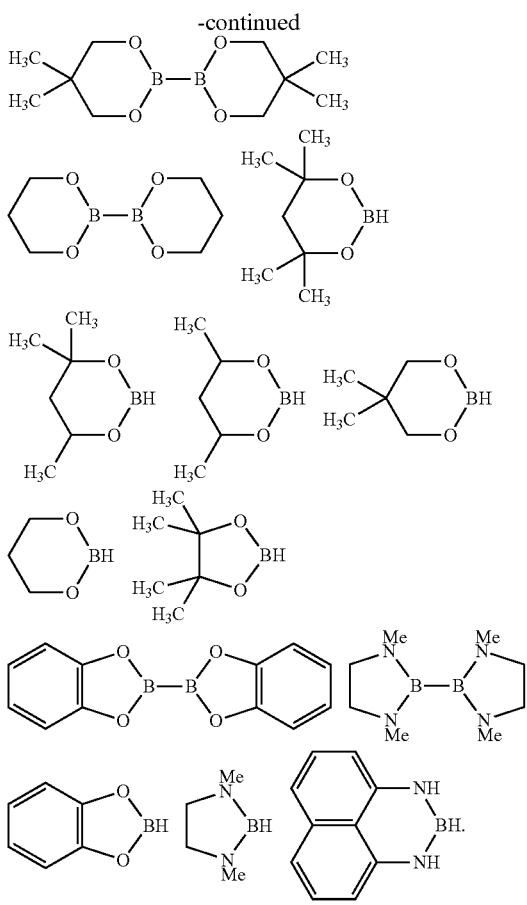

37. The method of any of embodiments 1-36, wherein the substrate, first borylated arene, and second borylated arene, when formed, further comprise a substituent selected from the group consisting of —Cl and —Br.
38. The method of embodiment 37, wherein the substrate comprises a compound defined by Formula I where $R_3$ is selected from the group consisting of —Cl and —Br, and the first borylated arene comprises a compound defined by Formula II where $R_3$ is selected from the group consisting of —Cl and —Br; and
 wherein the molar ratio of the first borylated arene to the second borylated arene is at least 25:1, as determined by GC-FID.
39. The method of embodiment 38, wherein the method further comprises reductively dehalogenating the first borylated arene to obtain a dehalogenated borylated arene.
40. The method of embodiment 39, wherein reductively dehalogenating the first borylated arene comprises contacting the first borylated arene with polymethylhydrosiloxane (PMHS) and a transition metal catalyst under conditions effective to reductively dehalogenate the first borylated arene.
41. The method of embodiment 40, wherein the transition metal catalyst comprises palladium(II) acetate.
42. The method of embodiment 39, wherein reductively dehalogenating the first borylated arene comprises contacting the first borylated arene with a formate salt and a transition metal catalyst under conditions effective to reductively dehalogenate the first borylated arene.
43. The method of embodiment 42, wherein the transition metal catalyst comprises palladium on carbon.
44. The method of embodiment 42 or 43, wherein the formate salt comprises ammonium formate.
45. The method of any of embodiments 39-44, wherein the first borylated arene is formed and reductively dehalogenated to form the dehalogenated borylated arene using a one-pot synthetic methodology.
46. The method of any of embodiments 1-45, further comprising contacting the first borylated arene or the dehalogenated borylated arene with a reactant selected from the group consisting of an aryl halide, an aryl pseudohalide, a vinyl halide, and a vinyl pseudohalide, and a transition metal catalyst to cross-couple the first borylated arene or the dehalogenated borylated arene and the reactant.
47. An iridium complex defined by the structure below $$(L)Ir(B)_3(Z_2)$$

wherein
 B is —B(OR)$_2$, wherein R is, independently for each occurrence, a $C_1$-$C_6$ alkyl group, or wherein the two R groups, taken together with the atoms to which they are attached, form a $C_2$-$C_6$ cyclic moiety, optionally substituted with one or more $C_1$-$C_6$ alkyl groups, and optionally fused with one or more carbocyclyl or heterocarbocyclyl groups;
 $Z_2$ is 1,5-cyclooctadiene, cyclooctene, or mesitylene; and
 L is a bidentate ligand selected from the following:

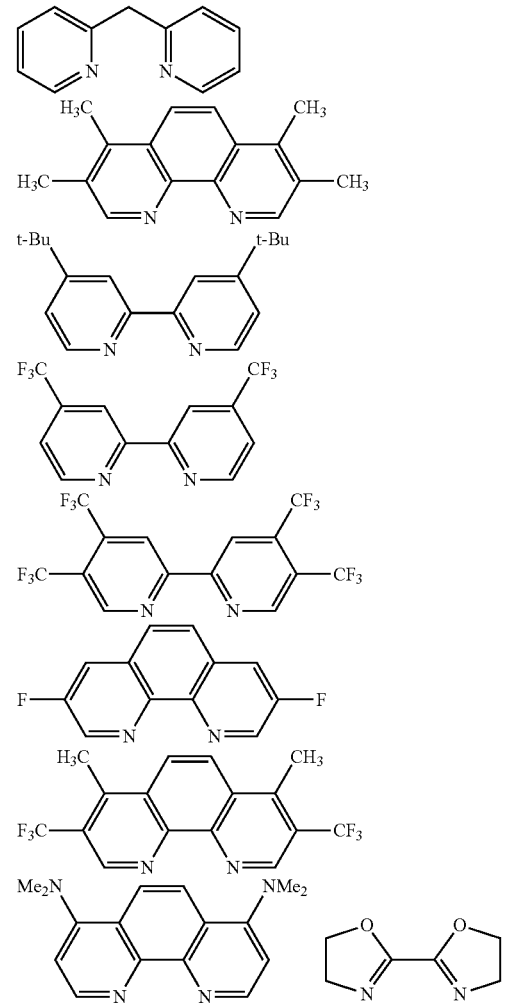

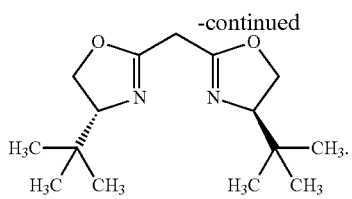

48. An iridium complex defined by the structure below (L)Ir(B)$_3$(Z$_2$)

wherein

B is —B(OR)$_2$, wherein R is, independently for each occurrence, a C$_1$-C$_6$ alkyl group, or wherein the two R groups, taken together with the atoms to which they are attached, form a C$_2$-C$_6$ cyclic moiety, optionally substituted with one or more C$_1$-C$_6$ alkyl groups, and optionally fused with one or more carbocyclyl or heterocarbocyclyl groups;

Z$_2$ is 1,5-cyclooctadiene, cyclooctene, or mesitylene; and

L is a bidentate ligand which comprises a compound defined by Formula IVa, Formula IVb, or Formula IVc

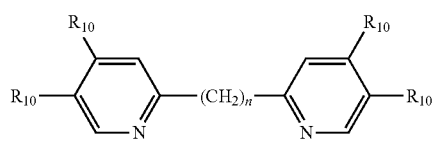
Formula IVa

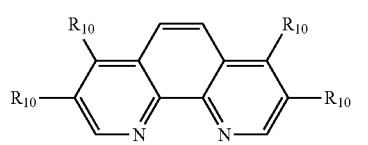
Formula IVb

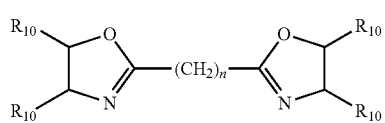
Formula IVc wherein n is 0, 1, 2, or 3 and R$_{10}$ is, independently for each occurrence, hydrogen, a halogen, a nitrile group, a nitro group, a C$_1$-C$_6$ alkyl group, or a C$_1$-C$_6$ perfluoroalkyl group, with the proviso that one or more of R$_{10}$ is not hydrogen when the bidentate ligand comprises a compound defined by Formula IVa or Formula IVb.

49. The complex of embodiment 48, wherein L is selected from one or more of the following:

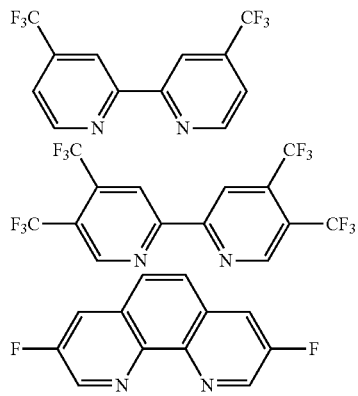

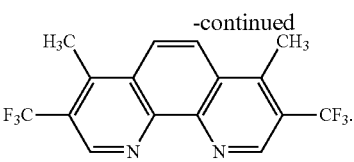

50. The complex of any of embodiments 47-49, wherein each B is independently selected from one of the following:

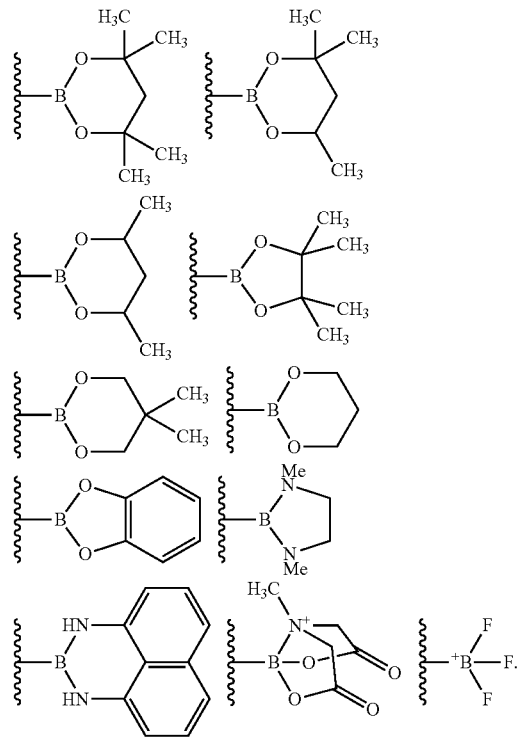

51. The method of any of embodiments 47-50, wherein B is pinacolborane.

52. A method of forming a borylated arene comprising:
providing an aromatic substrate comprising an aromatic ring substituted with a moiety chosen from an electron-withdrawing group and a directed metalating group, wherein the aromatic ring is unsubstituted in a position ortho to the moiety; and contacting the aromatic substrate with an iridium precursor complex, a monodentate ligand, and a borylation reagent under conditions effective to form a first borylated arene wherein the first borylated arene comprises an aromatic ring substituted with a moiety chosen from an electron-withdrawing group and a directed metalating group, and a boronic acid or a boronic acid derivative in a position ortho to the moiety.

53. The method of embodiment 52, wherein the aromatic ring is unsubstituted in a position ortho to the moiety and unsubstituted in a position meta to the moiety.

54. The method of embodiment 53, comprising contacting the aromatic substrate with an iridium precursor complex, a monodentate ligand, and a borylation reagent under conditions effective to form the first borylated arene and a second borylated arene;
wherein the second borylated arene comprises an aromatic ring substituted with a moiety chosen from an electron-withdrawing group and a directed metalating group, and a boronic acid or a boronic acid derivative in a position meta to the moiety; and wherein the molar ratio of the first borylated arene to the second borylated arene is at least 1:1, as determined by GC-FID.

55. The method of any of embodiments 52-54, wherein the moiety is an electron-withdrawing group selected from the group consisting of —F and —CF$_3$ 56. The method of any of embodiments 52-54, wherein the moiety is a directed metalating group selected from the group consisting of —OR$_{13}$, —NR$_{14}$R$_{15}$—C(=O)R$_{16}$, —OC(=O)R$_{16}$, a nitrile group, —SO$_2$R$_{16}$, —SOR$_{16}$, or a C$_1$-C$_6$ aminoalkyl group, wherein R$_{13}$, R$_{14}$, and R$_{15}$ are each, individually for each occurrence, hydrogen, a C$_1$-C$_6$ alkyl group, or an aryl group, and R$_{16}$ is, individually for each occurrence, hydrogen, —OR$_{13}$, —NR$_{14}$R$_{15}$, a C$_1$-C$_6$ alkyl group, or an aryl group, 57. The method of any of embodiments 52-56, wherein the aromatic substrate is selected from the group consisting of a substituted aryl compound, a substituted six-membered heteroaromatic compound, a substituted five-membered heteroaromatic compound, and combinations thereof.

58. The method of any of embodiments 54-57, wherein the aromatic substrate comprises a compound defined by the formula below

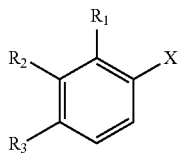

wherein

X is a moiety chosen from an electron-withdrawing group or a directed metalating group;

R$_1$ is hydrogen, a halogen, —OR$_4$, —NR$_5$R$_6$, —C(=O)R$_7$, a nitrile group, a C$_1$-C$_6$ alkyl group, or a C$_1$-C$_6$ haloalkyl group;

R$_2$ is hydrogen, a halogen, —OR$_4$, —NR$_5$R$_6$, —C(=O)R$_7$, a nitrile group, a C$_1$-C$_6$ alkyl group, or a C$_1$-C$_6$ haloalkyl group;

R$_3$ is hydrogen, a halogen, —OR$_4$, —NR$_5$R$_6$, —C(=O)R$_7$, a nitrile group, a C$_1$-C$_6$ alkyl group, or a C$_1$-C$_6$ haloalkyl group;

R$_4$, R$_5$, and R$_6$ are each, individually for each occurrence, hydrogen or a C$_1$-C$_6$ alkyl group; and R$_7$ is, individually for each occurrence, hydrogen, —OR$_4$, —NR$_5$R$_6$, or a C$_1$-C$_6$ alkyl group;

the first borylated arene comprises a compound defined by formula below

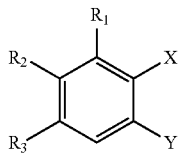

wherein

X, R$_1$, R$_2$, and R$_3$ are as described above, and Y is a boronic acid or a boronic acid derivative; and the second borylated arene, when formed, comprises a compound defined by the formula below

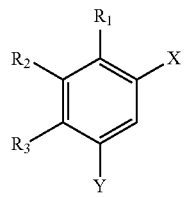

wherein

X, R$_1$, R$_2$, and R$_3$ are as described above, and Y is a boronic acid or a boronic acid derivative.

59. The method of any of embodiments 52-58, wherein first borylated arene comprises a boronic acid derivative in a position ortho to the moiety which is selected from one of the following:

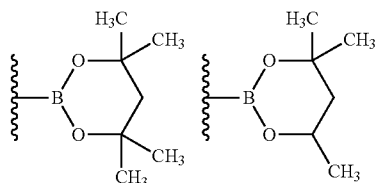

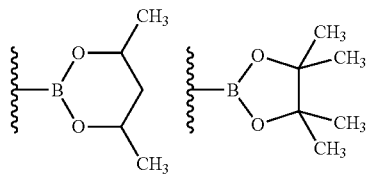

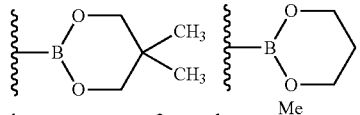

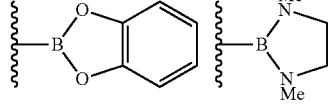

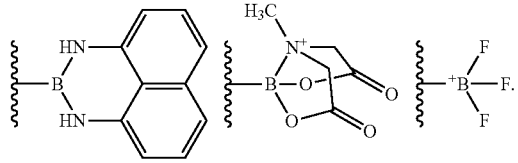

60. The method of any of embodiments 52-59, wherein the aromatic substrate comprises a 1-chloro-3-fluoro-2-substituted benzene.

61. The method of any of embodiments 52-60, wherein the aromatic substrate comprises 1-chloro-3-fluoro-2-methoxybenzene.

62. The method of any of embodiments 52-61, wherein the first borylated arene comprises (4-chloro-2-fluoro-3-methoxyphenyl)boronic acid or a (4-chloro-2-fluoro-3-methoxyphenyl)-boronic acid derivative.

63. The method of any of embodiments 54-62, wherein the molar ratio of the first borylated arene to the second borylated arene is at least 3:1.

64. The method of any of embodiments 54-63, wherein percent conversion to the first borylated arene and the second borylated arene is at least 30%.

65. The method of any of embodiments 54-64, wherein percent conversion to the first borylated arene and the second borylated arene is at least 50%.
66. The method of any of embodiments 52-65, wherein the iridium precursor complex comprises an Ir(I)-cyclooctadiene precursor complex.
67. The method of embodiment 66, wherein the Ir(I)-cyclooctadiene precursor complex is selected from the group consisting of [Ir(OMe)cod]$_2$, [Ir(Cl)cod]$_2$, [Ir(cod)$_2$]BF$_4$, [Ir(OH)cod]$_2$, [Ir(OPh)cod]$_2$, [Ir(OAc)cod]$_2$, (Ind)Ir(cod), Ir(acac)cod, (dtbpy)Ir(BPin)$_3$(cod), (tmp)Ir(BPin)$_3$(cod), and combinations thereof.
68. The method of any one of embodiments 52-65, wherein the iridium precursor complex comprises an Ir(I)-cyclooctene precursor complex.
69. The method of embodiment 68, wherein the Ir(I)-cyclooctene precursor complex is selected from the group consisting of [Ir(OMe)coe]$_2$, [Ir(Cl)coe]$_2$, [Ir(coe)$_2$]BF$_4$, [Ir(OH)coe]$_2$, [Ir(OPh)coe]$_2$, [Ir(OAc)coe]$_2$, (Ind)Ir(coe), Ir(acac)coe, (dtbpy)Ir(BPin)$_3$(coe), (tmp)Ir(BPin)$_3$(coe), [IrCl(coe)$_2$]$_2$, and combinations thereof.
70. The method of any one of embodiments 52-65, wherein the iridium precursor complex comprises an Ir(I)-mesitylene precursor complex.
71. The method of embodiment 70, wherein the Ir(I)-mesitylene precursor complex is selected from the group consisting of (MesH)Ir(BPin)(B(OR$_{11}$)$_2$), (MesH)Ir(BPin)$_3$, and combinations thereof, wherein BPin is pinacolborane, and R$_{11}$ is hydrogen, a linear or branched C$_1$-C$_8$ alkyl group, an aryl group, or a C$_3$-C$_8$ cycloalkyl group.
72. The method of any of embodiments 52-65, wherein the iridium precursor complex comprises an Ir(I)-phosphine precursor complex.
73. The method of embodiment 72, wherein the Ir(I)-phosphine precursor complex is selected from the group consisting of (dppbz)Ir(BPin)$_3$, (Ind)Ir(dppe), (PMe$_3$)$_2$IrH$_5$, ((R$_{11}$)$_3$P)$_2$IrH$_5$, ((R$_{11}$)$_3$P)$_3$Ir(B(OR$_{11}$)$_2$)$_3$, (R$_{11}$)$_2$P)$_2$Ir(BPin)$_3$, (((R$_{11}$)$_2$P)$_3$Ir((R$_{11}$O)$_2$B)$_3$)$_2$, ((R$_{11}$)$_3$P)$_4$Ir(BPin), ((R$_{11}$)$_3$P)$_2$IrH$_x$(B(OR$_{11}$)$_2$)$_{5-x}$, and combinations thereof, wherein x is an integer between 0-4, dppbz is 1,2-bis(diphenylphosphino)benzene, BPin is pinacolborane, and R$_{11}$ is hydrogen, a linear or branched C$_1$-C$_8$ alkyl group, an aryl group, or a C$_3$-C$_8$ cycloalkyl group.
74. The method of any of embodiments 52-65, wherein the iridium precursor complex comprises an Ir(I)-1,2,3,4,5-methylcyclopentadienyl precursor complex.
75. The method of embodiment 74, wherein the Ir(I)-1,2,3,4,5-methylcyclopentadienyl precursor complex is selected from the group consisting of (Cp*)Ir(H)$_2$(Me$_3$P), (Cp*)Ir(H)(BPin)(Me$_3$P), (Cp*)Ir(H)(C$_6$H$_5$)(Me$_3$P), and combinations thereof.
76. The method of any of embodiments 52-75, wherein the monodentate pyridine ligand comprises a compound defined by the formula below

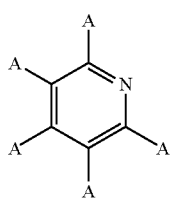

wherein A is, independently for each occurrence, hydrogen, halogen, —OR$_{13}$, —NR$_{14}$R$_{15}$, —C(=O)R$_{16}$, —OC(=O)R$_{16}$, a nitrile group, a C$_1$-C$_6$ alkyl group, a C$_1$-C$_6$ haloalkyl group, and a C$_1$-C$_6$ aminoalkyl group, wherein R$_{13}$, R$_{14}$, and R$_{15}$ are each, individually for each occurrence, hydrogen, a C$_1$-C$_6$ alkyl group, or an aryl group, and R$_{16}$ is, individually for each occurrence, hydrogen, —OR$_{13}$, —NR$_{14}$R$_{15}$, a C$_1$-C$_6$ alkyl group, or an aryl group, with the proviso that one or more of A is not hydrogen.

77. The method of embodiment 76, wherein the monodentate pyridine ligand comprises pyridine defined by the formula below

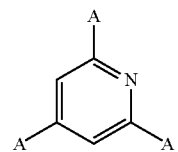

wherein A is, independently for each occurrence, hydrogen, halogen, —OR$_{13}$, —NR$_{14}$R$_{15}$, —C(=O)R$_{16}$, —OC(=O)R$_{16}$, a nitrile group, a C$_1$-C$_6$ alkyl group, a C$_1$-C$_6$ haloalkyl group, and a C$_1$-C$_6$ aminoalkyl group, wherein R$_{13}$, R$_{14}$, and R$_{15}$ are each, individually for each occurrence, hydrogen, a C$_1$-C$_6$ alkyl group, or an aryl group, and R$_{16}$ is, individually for each occurrence, hydrogen, —OR$_{13}$, —NR$_{14}$R$_{15}$, a C$_1$-C$_6$ alkyl group, or an aryl group, with the proviso that one or more of A is not hydrogen.

78. The method of any of embodiments 76-77, wherein the monodentate pyridine ligand comprises pyridine defined by the formula below

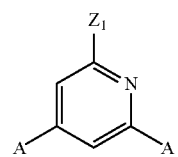

wherein A is, independently for each occurrence, hydrogen, halogen, —OR$_{13}$, —NR$_{14}$R$_{15}$, —C(=O)R$_{16}$, —OC(=O)R$_{16}$, a nitrile group, a C$_1$-C$_6$ alkyl group, a C$_1$-C$_6$ haloalkyl group, and a C$_1$-C$_6$ aminoalkyl group, wherein R$_{13}$, R$_{14}$, and R$_{15}$ are each, individually for each occurrence, hydrogen, a C$_1$-C$_6$ alkyl group, or an aryl group, and R$_{16}$ is, individually for each occurrence, hydrogen, —OR$_{13}$, —NR$_{14}$R$_{15}$, a C$_1$-C$_6$ alkyl group, or an aryl group, and Z$_1$ is halogen, —OR$_{13}$, —NR$_{14}$R$_{15}$, —C(=O)R$_{16}$, —OC(=O)R$_{16}$, a nitrile group, a C$_1$-C$_6$ alkyl group, a C$_1$-C$_6$ haloalkyl group, and a C$_1$-C$_6$ aminoalkyl group, wherein R$_{13}$, R$_{14}$, and R$_{15}$ are each, individually for each occurrence, hydrogen, a C$_1$-C$_6$ alkyl group, or an aryl group, and R$_{16}$ is, individually for each occurrence, hydrogen, —OR$_{13}$, —NR$_{14}$R$_{15}$, a C$_1$-C$_6$ alkyl group, or an aryl group.

79. The method of any of embodiments 76-78, wherein the monodentate pyridine ligand comprises pyridine defined by the formula below

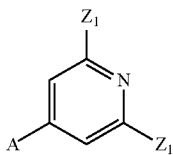

wherein A is hydrogen, halogen, —OR$_{13}$, —NR$_{14}$R$_{15}$, —C(=O)R$_{16}$, —OC(=O)R$_{16}$, a nitrile group, a C$_1$-C$_6$ alkyl group, a C$_1$-C$_6$ haloalkyl group, and a C$_1$-C$_6$ aminoalkyl group, wherein R$_{13}$, R$_{14}$, and R$_{15}$ are each, individually for each occurrence, hydrogen, a C$_1$-C$_6$ alkyl group, or an aryl group, and R$_{16}$ is, individually for each occurrence, hydrogen, —OR$_{13}$, —NR$_{14}$R$_{15}$, a C$_1$-C$_6$ alkyl group, or an aryl group, and Z$_1$ is, independently for each occurrence, halogen, —OR$_{13}$, —NR$_{14}$R$_{15}$, —C(=O)R$_{16}$, —OC(=O)R$_{16}$, a nitrile group, a C$_1$-C$_6$ alkyl group, a C$_1$-C$_6$ haloalkyl group, and a C$_1$-C$_6$ aminoalkyl group, wherein R$_{13}$, R$_{14}$, and R$_{15}$ are each, individually for each occurrence, hydrogen, a C$_1$-C$_6$ alkyl group, or an aryl group, and R$_{16}$ is, individually for each occurrence, hydrogen, —OR$_{13}$, —NR$_{14}$R$_{15}$, a C$_1$-C$_6$ alkyl group, or an aryl group.

80. The method of any of embodiments 76-77, wherein the monodentate pyridine ligand comprises pyridine defined by the formula below

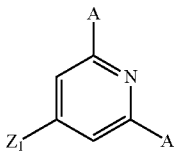

wherein A is, independently for each occurrence, hydrogen, halogen, —OR$_{13}$, —NR$_{14}$R$_{15}$, —C(=O)R$_{16}$, —OC(=O)R$_{16}$, a nitrite group, a C$_1$-C$_6$ alkyl group, a C$_1$-C$_6$ haloalkyl group, and a C$_1$-C$_6$ aminoalkyl group, wherein R$_{13}$, R$_{14}$, and R$_{15}$ are each, individually for each occurrence, hydrogen, a C$_1$-C$_6$ alkyl group, or an aryl group, and R$_{16}$ is, individually for each occurrence, hydrogen, —OR$_{13}$, —NR$_{14}$R$_{15}$, a C$_1$-C$_6$ alkyl group, or an aryl group, and Z$_1$ is halogen, —OR$_{13}$, —NR$_{14}$R$_{15}$, —C(=O)R$_{16}$, —OC(=O)R$_{16}$, a nitrile group, a C$_1$-C$_6$ alkyl group, a C$_1$-C$_6$ haloalkyl group, and a C$_1$-C$_6$ aminoalkyl group, wherein R$_{13}$, R$_{14}$, and R$_{15}$ are each, individually for each occurrence, hydrogen, a C$_1$-C$_6$ alkyl group, or an aryl group, and R$_{16}$ is, individually for each occurrence, hydrogen, —OR$_{13}$, —NR$_{14}$R$_{15}$, a C$_1$-C$_6$ alkyl group, or an aryl group.

81. The method of embodiment 76, wherein the monodentate pyridine ligand comprises pyridine defined by the formula below

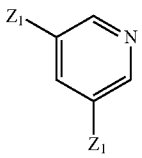

wherein Z$_1$ is, independently for each occurrence, halogen, —OR$_{13}$, —NR$_{14}$R$_{15}$, —C(=O)R$_{16}$, —OC(=O)R$_{16}$, a nitrile group, a C$_1$-C$_6$ alkyl group, a C$_1$-C$_6$ haloalkyl group, and a C$_1$-C$_6$ aminoalkyl group, wherein R$_{13}$, R$_{14}$, and R$_{15}$ are each, individually for each occurrence, hydrogen, a C$_1$-C$_6$ alkyl group, or an aryl group, and R$_{16}$ is, individually for each occurrence, hydrogen, —OR$_{13}$, —NR$_{14}$R$_{15}$, a C$_1$-C$_6$ alkyl group, or an aryl group.

82. The method of any of embodiments 78-81, wherein Z$_1$ is, independently for each occurrence, —F, —Cl, —CF$_3$, -Me, —OMe, —CH$_2$NH$_2$, —NHMe, —NMe$_2$, —NPh$_2$, phenyl, isopropyl, tert-butyl, or —COCH$_3$.

83. The method of any of embodiments 52-82, wherein the borylation reagent is selected from one or more of the following:

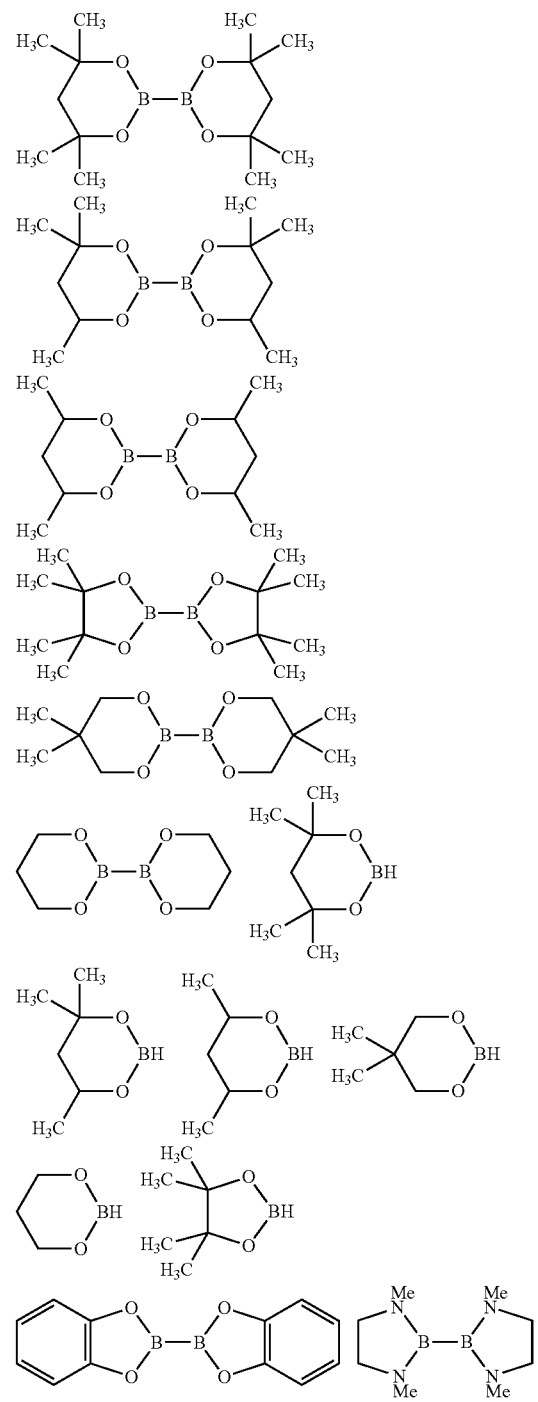

-continued

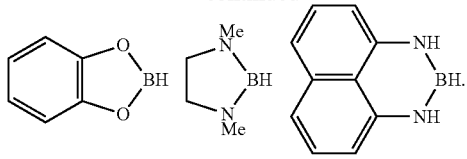

84. The method of any of embodiments 52-83, wherein the aromatic substrate, first borylated arene, and second borylated arene, when formed, further comprise a substituent selected from the group consisting of —Cl and —Br.

85. The method of any of embodiments 58-84, wherein the aromatic substrate comprises a compound defined by the formula below

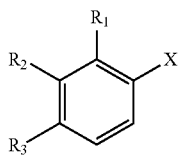

wherein
X is a moiety chosen from an electron-withdrawing group or a directed metalating group;
$R_1$ is hydrogen, a halogen, —$OR_4$, —$NR_5R_6$, —C(=O)$R_7$, a nitrile group, a $C_1$-$C_6$ alkyl group, or a $C_1$-$C_6$ haloalkyl group;
$R_2$ is hydrogen, a halogen, —$OR_4$, —$NR_5R_6$, —C(=O)$R_7$, a nitrile group, a $C_1$-$C_6$ alkyl group, or a $C_1$-$C_6$ haloalkyl group;
$R_3$ is —Cl and —Br;
$R_4$, $R_5$, and $R_6$ are each, individually for each occurrence, hydrogen or a $C_1$-$C_6$ alkyl group; and
$R_7$ is, individually for each occurrence, hydrogen, —$OR_4$, —$NR_5R_6$, or a $C_1$-$C_6$ alkyl group;
the first borylated arene comprises a compound defined by formula below

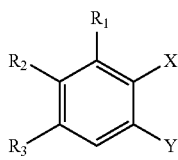

wherein
X, $R_1$, $R_2$, and $R_3$ are as described above, and Y is a boronic acid or a boronic acid derivative; and
the second borylated arene, when formed, comprises a compound defined by the formula below

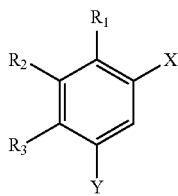

wherein
X, $R_1$, $R_2$, and $R_3$ are as described above, and Y is a boronic acid or a boronic acid derivative
wherein the molar ratio of the first borylated arene to the second borylated arene is at least 25:1, as determined by GC-FID.

86. The method of embodiment 85, wherein the method further comprises reductively dehalogenating the first borylated arene to obtain a dehalogenated borylated arene.

87. The method of embodiment 86, wherein reductively dehalogenating the first borylated arene comprises contacting the first borylated arene with polymethylhydrosiloxane (PMHS) and a transition metal catalyst under conditions effective to reductively dehalogenate the first borylated arene.

88. The method of embodiment 87, wherein the transition metal catalyst comprises palladium(II) acetate.

89. The method of embodiment 86, wherein reductively dehalogenating the first borylated arene comprises contacting the first borylated arene with a formate salt and a transition metal catalyst under conditions effective to reductively dehalogenate the first borylated arene.

90. The method of embodiment 89, wherein the transition metal catalyst comprises palladium on carbon.

91. The method of embodiment 89 or 90, wherein the formate salt comprises ammonium formate.

92. The method of any of embodiments 86-91, wherein the first borylated arene is formed and reductively dehalogenated to form the dehalogenated borylated arene using a one-pot synthetic methodology.

93. The method of any of embodiments 52-92, further comprising contacting the first borylated arene or the dehalogenated borylated arene with a reactant selected from the group consisting of an aryl halide, an aryl pseudohalide, a vinyl halide, and an vinyl pseudohalide, and a transition metal catalyst to cross-couple the first borylated arene or the dehalogenated borylated arene and the reactant.

94. A method of forming a borylated arene comprising:
providing a substrate comprising a substituted arene ring comprising from 1 to 3 substituents, wherein the arene ring is unsubstituted at a first position that is electronically favored for CH-activation and unsubstituted at a second position that is sterically favored for CH-activation; and
contacting the substrate with an iridium precursor complex, a ligand chosen from a monodentate ligand and a bidentate ligand, and a borylation reagent under conditions effective to form a first borylated arene and optionally a second borylated arene;
wherein the first borylated arene comprises a substituted arene ring comprising from 1 to 3 substituents and a boronic acid or a boronic acid derivative in the first position,
wherein the second borylated arene, when formed, comprises a substituted arene ring comprising from 1 to 3 substituents and a boronic acid or a boronic acid derivative in the second position, and
wherein the molar ratio of the first borylated arene to the second borylated arene is at least 1:1, as determined by GC-FID.

95. The method of embodiment 94, wherein the arene ring comprises a phenyl ring.

96. The method of embodiment 94, wherein the arene ring comprises a pyridine ring.

97. The method of embodiment 96, wherein the pyridine ring comprises a 2,4-disubstituted pyridine ring.

98. The method of embodiment 96, wherein the pyridine ring comprises a 2,6-disubstituted pyridine ring.

99. The method of embodiment 96, wherein the pyridine ring comprises a 2,4,6-trisubstituted pyridine ring.
100. The method of embodiment 96, wherein the pyridine ring comprises a 2-substituted pyridine ring.
101. The method of any of embodiments 94-100, wherein the 1 to 3 substituents are individually selected from halogen, —OR$_{13}$, —NR$_{14}$R$_{15}$, —C(=O)R$_{16}$, —OC(=O)R$_{16}$, a nitrile group, a C$_1$-C$_6$ alkyl group, a C$_1$-C$_6$ haloalkyl group, and a C$_1$-C$_6$ aminoalkyl group,
wherein R$_{13}$, R$_{14}$, and R$_{15}$ are each, individually for each occurrence, hydrogen, a C$_1$-C$_6$ alkyl group, or an aryl group, and R$_{16}$ is, individually for each occurrence, hydrogen, —OR$_{13}$, —NR$^1{}_{16}$R$_{15}$, a C$_1$-C$_6$ alkyl group, or an aryl group.
102. The method of any of embodiments 94-100, wherein the arene ring comprises an electron-withdrawing group selected from the group consisting of —F and —CF$_3$.
103. The method of any of embodiments 94-102, wherein the first borylated arene comprises a boronic acid derivative in a position ortho to the electron-withdrawing group which is selected from one of the following:

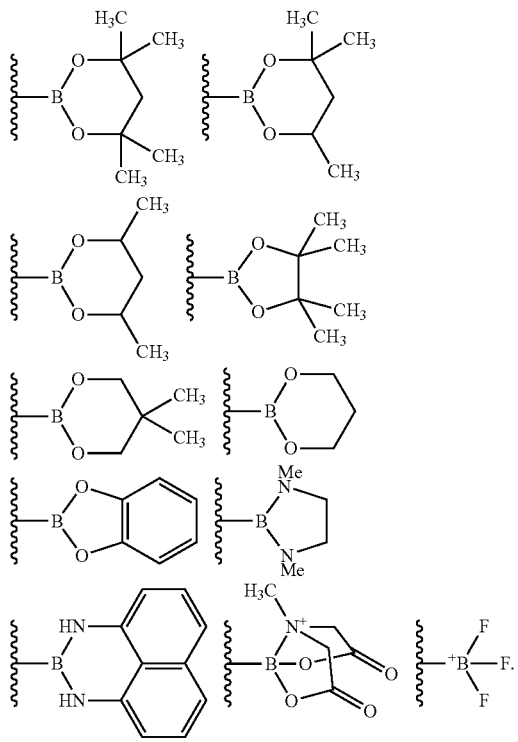

104. The method of any of embodiments 94-103, wherein the molar ratio of the first borylated arene to the second borylated arene is at least 3:1.
105. The method of any of embodiments 94-104, wherein percent conversion to the first borylated arene and the second borylated arene is at least 30%.
106. The method of any of embodiments 94-105, wherein percent conversion to the first borylated arene and the second borylated arene is at least 50%.
107. The method of any of embodiments 94-106, wherein the iridium precursor complex comprises an Ir(I)-cyclooctadiene precursor complex.
108. The method of embodiment 107, wherein the Ir(I)-cyclooctadiene precursor complex is selected from the group consisting of [Ir(OMe)cod]$_2$, [Ir(Cl)cod]$_2$, [Ir(cod)$_2$]BF$_4$, [Ir(OH)cod]$_2$, [Ir(OPh)cod]$_2$, [Ir(OAc)cod]$_2$, (Ind)Ir(cod), Ir(acac)cod, (dtbpy)Ir(BPin)$_3$(cod), (tmp)Ir(BPin)$_3$(cod), and combinations thereof.
109. The method of any one of embodiments 94-106, wherein the iridium precursor complex comprises an Ir(I)-cyclooctene precursor complex.
110. The method of embodiment 109, wherein the Ir(I)-cyclooctene precursor complex is selected from the group consisting of [Ir(OMe)coe]$_2$, [Ir(Cl)coe]$_2$, [Ir(coe)$_2$]BF$_4$, [Ir(OH)coe]$_2$, [Ir(OPh)coe]$_2$, [Ir(OAc)coe]$_2$, (Ind)Ir(coe), Ir(acac)coe, (dtbpy)Ir(BPin)$_3$(coe), (tmp)Ir(BPin)$_3$(coe), [IrCl(coe)$_2$]$_2$, and combinations thereof.
111. The method of any one of embodiments 94-106, wherein the iridium precursor complex comprises an Ir(I)-mesitylene precursor complex.
112. The method of embodiment 111, wherein the Ir(I)-mesitylene precursor complex is selected from the group consisting of (MesH)Ir(BPin)(B(OR$_{11}$)$_2$), (MesH)Ir(BPin)$_3$, and combinations thereof, wherein BPin is pinacolborane, and R$_{11}$ is hydrogen, a linear or branched C$_1$-C$_8$ alkyl group, an aryl group, or a C$_3$-C$_8$ cycloalkyl group.
113. The method of any of embodiments 94-106, wherein the iridium precursor complex comprises an Ir(I)-phosphine precursor complex.
114. The method of embodiment 113, wherein the Ir(I)-phosphine precursor complex is selected from the group consisting of (dppbz)Ir(BPin)$_3$, (Ind)Ir(dppe), (PMe$_3$)$_2$IrH$_5$, ((R$_{11}$)$_3$P)$_2$IrH$_5$, ((R$_{11}$)$_3$P)$_3$Ir(B(OR$_{11}$)$_2$)$_3$, (R$_{11}$)$_2$P)$_2$Ir(BPin)$_3$, (((R$_{11}$)$_2$P)$_3$IR(R$_{11}$O)$_2$B)$_3$)$_2$, ((R$_{11}$)$_3$P)$_4$Ir(BPin), ((R$_{11}$)$_3$P)$_2$IrH$_x$(B(OR$_{11}$)$_2$)$_{5-x}$, and combinations thereof, wherein x is an integer between 0-4, dppbz is 1,2-bis(diphenylphosphino)benzene, BPin is pinacolborane, and R$_{11}$ is hydrogen, a linear or branched C$_1$-C$_8$ alkyl group, an aryl group, or a C$_3$-C$_8$ cycloalkyl group.
115. The method of any of embodiments 94-106, wherein the iridium precursor complex comprises an Ir(I)-1,2,3,4,5-methylcyclopentadienyl precursor complex.
116. The method of embodiment 115, wherein the Ir(I)-1,2,3,4,5-methylcyclopentadienyl precursor complex is selected from the group consisting of (Cp*)Ir(H)$_2$(Me$_3$P), (Cp*)Ir(H)(BPin)(Me$_3$P), (Cp*)Ir(H)(C$_6$H$_5$)(Me$_3$P), and combinations thereof
117. The method of any of embodiments 94-106, wherein the ligand comprises a bidentate ligand.
118. The method of embodiment 117, wherein the bidentate ligand comprises an electron-deficient bidentate ligand.
119. The method of embodiment 117 or 118, wherein the bidentate ligand comprises 2,2'-bipyridine substituted with one or more electron-withdrawing substituents.
120. The method of any of embodiments 117-119, wherein the bidentate ligand comprises 2,2'-bipyridine substituted with one or more trifluoromethyl groups.
121. The method of any of embodiments 117-120, wherein the bidentate ligand comprises a compound defined by Formula IVa, Formula IVb, or Formula IVc Formula IVa

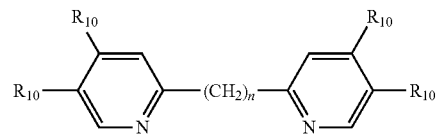

-continued

Formula IVb

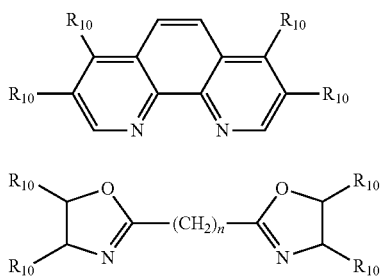

Formula IVc wherein n is 0, 1, 2, or 3 and $R_{10}$ is, independently for each occurrence, hydrogen, a halogen, a nitrile group, a nitro group, a $C_1$-$C_6$ alkyl group, or a $C_1$-$C_6$ perfluoroalkyl group, with the proviso that one or more of $R_{10}$ is not hydrogen when the bidentate ligand comprises a compound defined by Formula IVa or Formula IVb.

122. The method of embodiment 121, wherein one or more of $R_{10}$ is selected from —F and —$CF_3$.

123. The method of any of embodiments 117-122, wherein the bidentate ligand is selected from one or more of the following:

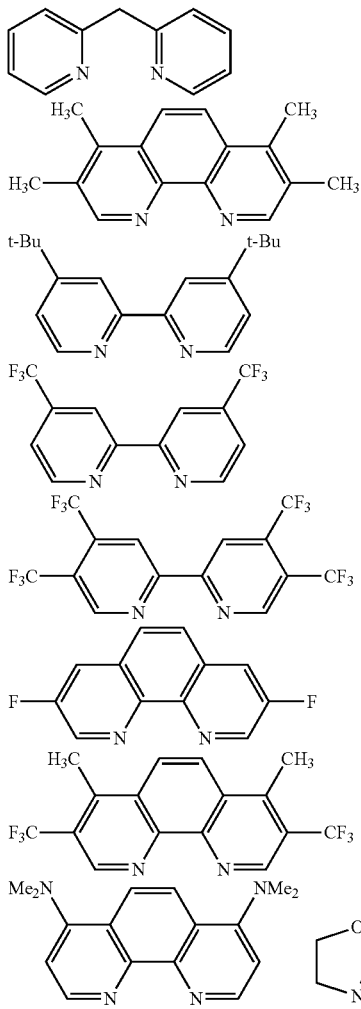

-continued

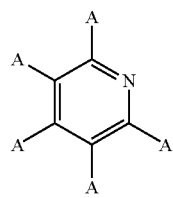

124. The method of any of embodiments 94-106, wherein the ligand comprises a monodentate ligand.

125. The method of embodiment 124, wherein the monodentate ligand comprises a pyridine ligand.

126. The method of embodiment 125, wherein the pyridine ligand comprises pyridine defined by the formula below

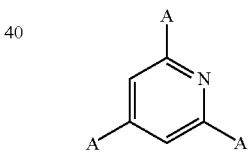

wherein A is, independently for each occurrence, hydrogen, halogen, —$OR_{13}$, —$NR_{14}R_{15}$, —$C(\!\!=\!\!O)R_{16}$, —$OC(\!\!=\!\!O)R_{16}$, a nitrile group, a $C_1$-$C_6$ alkyl group, a $C_1$-$C_6$ haloalkyl group, and a $C_1$-$C_6$ aminoalkyl group, wherein $R_{13}$, $R_{14}$, and $R_{15}$ are each, individually for each occurrence, hydrogen, a $C_1$-$C_6$ alkyl group, or an aryl group, and $R_{16}$ is, individually for each occurrence, hydrogen, —$OR_{13}$, —$NR_{14}R_{15}$, a $C_1$-$C_6$ alkyl group, or an aryl group, with the proviso that one or more of A is not hydrogen.

127. The method of embodiment 125 or 126, wherein pyridine ligand comprises pyridine defined by the formula below

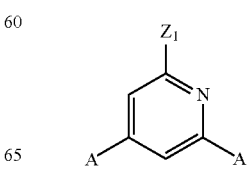

wherein A is, independently for each occurrence, hydrogen, halogen, —$OR_{13}$, —$NR_{14}R_{15}$, —$C(\!\!=\!\!O)R_{16}$, —$OC(\!\!=\!\!O)R_{16}$, a nitrile group, a $C_1$-$C_6$ alkyl group, a $C_1$-$C_6$ haloalkyl group, and a $C_1$-$C_6$ aminoalkyl group, wherein $R_{13}$, $R_{14}$, and $R_{15}$ are each, individually for each occurrence, hydrogen, a $C_1$-$C_6$ alkyl group, or an aryl group, and $R_{16}$ is, individually for each occurrence, hydrogen, —$OR_{13}$, —$NR_{14}R_{15}$, a $C_1$-$C_6$ alkyl group, or an aryl group, with the proviso that one or more of A is not hydrogen.

128. The method of any of embodiments 125-127, wherein the pyridine ligand comprises pyridine defined by the formula below wherein A is, independently for each occurrence, hydrogen, halogen, —$OR_{13}$, —$NR_{14}R_{15}$, —C(=O)$R_{16}$, —OC(=O)$R_{16}$, —OC(=O)$R_{16}$, a nitrile group, a $C_1$-$C_6$ alkyl group, a $C_1$-$C_6$ haloalkyl group, and a $C_1$-$C_6$ aminoalkyl group, wherein $R_{13}$, $R_{14}$, and $R_{15}$ are each, individually for each occurrence, hydrogen, a $C_1$-$C_6$ alkyl group, or an aryl group, and $R_{16}$ is, individually for each occurrence, hydrogen, —$OR_{13}$, —$NR_{14}R_{15}$, a $C_1$-$C_6$ alkyl group, or an aryl group, and $Z_1$ is halogen, —$OR_{13}$, —$NR_{14}R_{15}$, —C(=O)$R_{16}$, —OC(=O)$R_{16}$, a nitrile group, a $C_1$-$C_6$ alkyl group, a $C_1$-$C_6$ haloalkyl group, and a $C_1$-$C_6$ aminoalkyl group, wherein $R_{13}$, $R_{14}$, and $R_{15}$ are each, individually for each occurrence, hydrogen, a $C_1$-$C_6$ alkyl group, or an aryl group, and $R_{16}$ is, individually for each occurrence, hydrogen, —$OR_{13}$, —$NR_{14}R_{15}$, a $C_1$-$C_6$ alkyl group, or an aryl group.

129. The method of any of embodiments 125-128, wherein the pyridine ligand comprises pyridine defined by the formula below

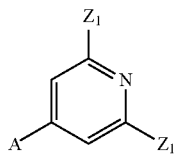

wherein A is hydrogen, halogen, —$OR_{13}$, —$NR_{14}R_{15}$, —C(=O)$R_{16}$, —OC(=O)$R_{16}$, a nitrile group, a $C_1$-$C_6$ alkyl group, a $C_1$-$C_6$ haloalkyl group, and a $C_1$-$C_6$ aminoalkyl group, wherein $R_{13}$, $R_{14}$, and $R_{15}$ are each, individually for each occurrence, hydrogen, a $C_1$-$C_6$ alkyl group, or an aryl group, and $R_{16}$ is, individually for each occurrence, hydrogen, —$OR_{13}$, —$NR_{14}R_{15}$, a $C_1$-$C_6$ alkyl group, or an aryl group, and $Z_1$ is, independently for each occurrence, halogen, —$OR_{13}$, —$NR_{14}R_{15}$, —C(=O)$R_{16}$, —OC(=O)$R_{16}$, a nitrite group, a $C_1$-$C_6$ alkyl group, a $C_1$-$C_6$ haloalkyl group, and a $C_1$-$C_6$ aminoalkyl group, wherein $R_{13}$, $R_{14}$, and $R_{15}$ are each, individually for each occurrence, hydrogen, a $C_1$-$C_6$ alkyl group, or an aryl group, and $R_{16}$ is, individually for each occurrence, hydrogen, —$OR_{13}$, —$NR_{14}R_{15}$, a $C_1$-$C_6$ alkyl group, or an aryl group.

130. The method of any of embodiments 125-127, wherein the pyridine ligand comprises pyridine defined by the formula below

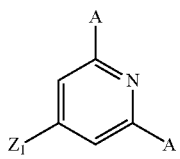

wherein A is, independently for each occurrence, hydrogen, halogen, —$OR_{13}$, —$NR_{14}R_{15}$, —C(=O)$R_{16}$, —OC(=O)$R_{16}$, a nitrile group, a $C_1$-$C_6$ alkyl group, a $C_1$-$C_6$ haloalkyl group, and a $C_1$-$C_6$ aminoalkyl group, wherein $R_{13}$, $R_{14}$, and $R_{15}$ are each, individually for each occurrence, hydrogen, a $C_1$-$C_6$ alkyl group, or an aryl group, and $R_{16}$ is, individually for each occurrence, hydrogen, —$OR_{13}$, —$NR_{14}R_{15}$, a $C_1$-$C_6$ alkyl group, or an aryl group, and $Z_1$ is halogen, —$OR_{13}$, —$NR_{14}R_{15}$, —C(=O)$R_{16}$, —OC(=O)$R_{16}$, a nitrile group, a $C_1$-$C_6$ alkyl group, a $C_1$-$C_6$ haloalkyl group, and a $C_1$-$C_6$ aminoalkyl group, wherein $R_{13}$, $R_{14}$, and $R_{15}$ are each, individually for each occurrence, hydrogen, a $C_1$-$C_6$ alkyl group, or an aryl group, and $R_{16}$ is, individually for each occurrence, hydrogen, —$OR_{13}$, —$NR_{14}R_{15}$, a $C_1$-$C_6$ alkyl group, or an aryl group.

131. The method of embodiment 125 or 126, wherein the pyridine ligand comprises pyridine defined by the formula below

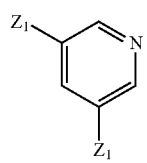

wherein $Z_1$ is, independently for each occurrence, halogen, —$OR_{13}$, —$NR_{14}R_{15}$, —C(=O)$R_{16}$, —OC(=O)$R_{16}$, a nitrile group, a $C_1$-$C_6$ alkyl group, a $C_1$-$C_6$ haloalkyl group, and a $C_1$-$C_6$ aminoalkyl group, wherein $R_{13}$, $R_{14}$, and $R_{15}$ are each, individually for each occurrence, hydrogen, a $C_1$-$C_6$ alkyl group, or an aryl group, and $R_{16}$ is, individually for each occurrence, hydrogen, —$OR_{13}$, —$NR_{14}R_{15}$, a $C_1$-$C_6$ alkyl group, or an aryl group.

132. The method of any of embodiments 128-131, wherein $Z_1$ is, independently for each occurrence, —F, —Cl, —$CF_3$, -Me, —OMe, —$CH_2NH_2$, —NHMe, —$NMe_2$, —$NPh_2$, phenyl, isopropyl, tert-butyl, or —$COCH_3$.

133. The method of any of embodiments 94-132, wherein the borylation reagent is selected from one or more of the following:

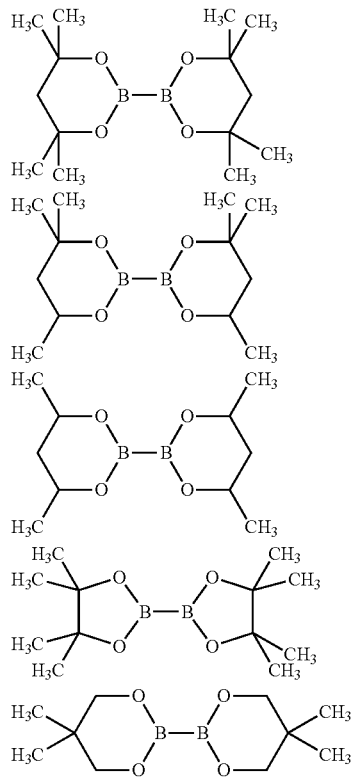

-continued

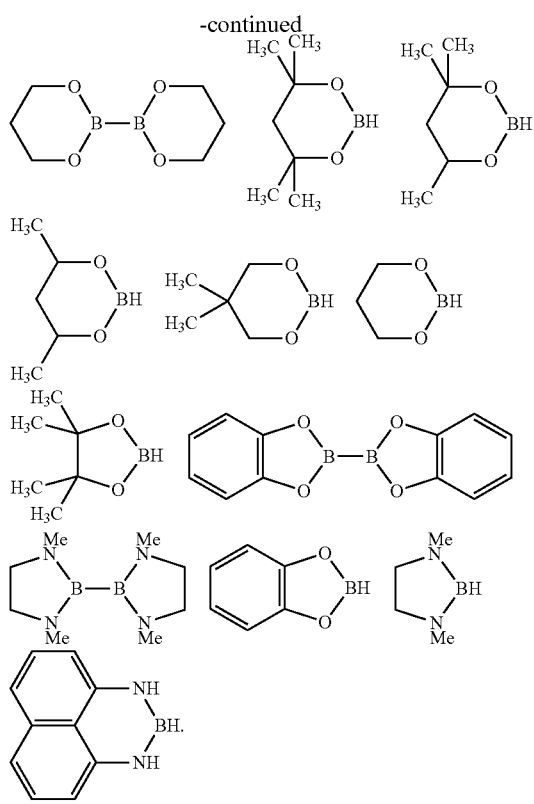

134. The method of any of embodiments 94-133, wherein the substituted arene ring, first borylated arene, and second borylated arene, when formed, comprise a substituent selected from the group consisting of —Cl and —Br.
135. The method of embodiment 134, wherein the method further comprises reductively dehalogenating the first borylated arene to obtain a dehalogenated borylated arene.
136. The method of embodiment 135, wherein reductively dehalogenating the first borylated arene comprises contacting the first borylated arene with polymethylhydrosiloxane (PMHS) and a transition metal catalyst under conditions effective to reductively dehalogenate the first borylated arene.
137. The method of embodiment 136, wherein the transition metal catalyst comprises palladium(II) acetate.
138. The method of embodiment 135, wherein reductively dehalogenating the first borylated arene comprises contacting the first borylated arene with a formate salt and a transition metal catalyst under conditions effective to reductively dehalogenate the first borylated arene.
139. The method of embodiment 138, wherein the transition metal catalyst comprises palladium on carbon.
140. The method of embodiment 138 or 139, wherein the formate salt comprises ammonium formate.
141. The method of any of embodiments 135-140, wherein the first borylated arene is formed and reductively dehalogenated to form the dehalogenated borylated arene using a one-pot synthetic methodology.
142. The method of any of embodiments 94-141, further comprising contacting the first borylated arene or the dehalogenated borylated arene with a reactant selected from the group consisting of an aryl halide, an aryl pseudohalide, a vinyl halide, and a vinyl pseudohalide, and a transition metal catalyst to cross-couple the first borylated arene or the dehalogenated borylated arene and the reactant.

By way of non-limiting illustration, examples of certain embodiments of the present disclosure are given below.

EXAMPLES

Material and Methods

Unless otherwise specified, reactions were performed in oven-dried glassware under an atmosphere of nitrogen, with magnetic stirring, and monitored by $^1$H NMR spectroscopy. Tetrahydrofuran (THF) was freshly distilled from sodium/benzophenone under nitrogen. Palladium(II) acetate (Pd(OAc)$_2$) was purchased from Strem Chemicals, Inc. (Newburyport, Mass.), anhydrous A. C. S.-grade potassium fluoride (KF) and polymethylhydrosiloxane (PMHS) were purchased from Sigma Aldrich (St. Louis, Mo.). Flash or column chromatography was performed with silica gel (230-400 mesh) purchased from Silicycle (Quebec City, Canada). $^1$H NMR, $^{13}$C NMR, $^{19}$F, and $^{11}$B NMR spectra were recorded using an Agilent DirectDrive2 500 MHz NMR spectrometer (500 MHz for $^1$H NMR, 125 MHz for $^{13}$C NMR, 470 MHz for $^{19}$F NMR and 160 MHz for $^{11}$B NMR) equipped with 7600AS 96 sample autosamplers running VnmrJ 3.2A. Melting points were measured on a Thomas-Hoover capillary melting point apparatus. Accurate mass analysis was recorded using a Waters GCT Premier gas chromatograph/time-of-flight mass spectrometer at the Michigan State University Mass Spectrometry Service Center; the products were ionized using an electron ionization source operated in the positive mode.

Example 1

Borylation of 1-Chloro-3-fluoro-2-Substituted Benzenes

1-Chloro-3-fluoro-2-substituted benzenes are important synthetic building blocks for a variety of important compounds, including herbicides. The ability of iridium-catalysts to preferably catalyze borylation of 1-chloro-3-fluoro-2-substituted benzenes at positions ortho to the fluoro substituent (the electronically-favored reaction product, termed the "electronic product") as opposed to at positions meta to the fluoro substituent (the sterically favored reaction product, termed the "steric product") was investigated.

General Procedure for the Borylation of 1-Chloro-3-fluoro-2-substituted Benzenes The scheme below illustrates the reaction conditions used for the borylation of representative 1-chloro-3-fluoro-2-substituted benzenes.

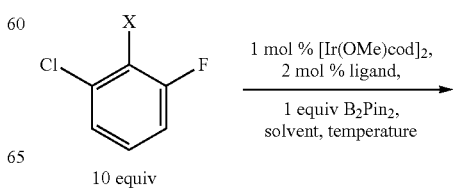

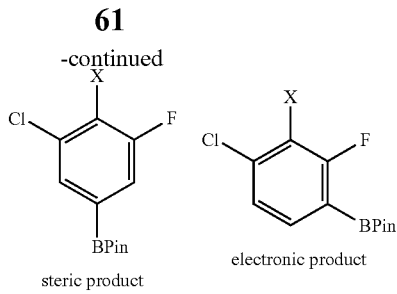

steric product     electronic product

In a nitrogen atmosphere glovebox, bis(pinacolato)diboron (B$_2$Pin$_2$; 254 milligrams (mg), 1.0 millimole (mmol)) was weighed into a 20 milliliter (mL) vial and dissolved in THF (2 mL). The resulting solution was transferred to a 10 mL volumetric flask. The vial was washed with THF (3×1 mL), and the resulting solutions were transferred to the volumetric flask. The solution in the volumetric flask was diluted to the 10 mL mark with THF, giving a 0.10 molar (M) stock solution of B$_2$Pin$_2$. Bis(1,5-cyclooctadiene)di-µ-methoxydi-iridium(I) ([Ir(OMe)cod]$_2$; 33.1 mg, 0.050 mmol) was weighed into a 20 mL vial and dissolved in THF (2 mL). The resulting solution was transferred to a 10 mL volumetric flask. The vial was washed with THF (3×1 mL), and the resulting solutions were transferred to the volumetric flask. The solution in the volumetric flask was diluted to the 10 mL mark with THF, giving a 0.0050 M stock solution of [Ir(OMe)cod]$_2$. A ligand (0.10 mmol) was weighed into a 20 mL vial and dissolved in THF (2 mL). The resulting solution was transferred to a 10 mL volumetric flask. The vial was washed with THF (3×1 mL), and the resulting solutions were transferred to the volumetric flask. The solution in the volumetric flask was diluted to the 10 mL mark with THF, giving a 0.010 M stock solution of ligand.

A J-Young NMR tube was charged with the 0.0050 M stock solution of [Ir(OMe)cod]$_2$ (200 microliters (µL), 0.001 mmol), the 0.10 M stock solution of B$_2$Pin$_2$ (1.0 mL, 0.1 mmol), and the 0.010 M stock solution of ligand (200 µL, 0.002 mmol). The substrate (1.0 mmol) was added to the tube. The J-Young NMR tube was capped and shaken well to mix the liquids, removed from the glovebox and heated in an oil bath at 80° C. The reaction progress was monitored by removing the tube from the oil bath occasionally and acquiring $^{19}$F and $^{11}$B NMR spectra. After the reaction was judged complete, the volatiles were removed by rotary evaporation. The residue was then purified by Kugelrohr distillation to give the regiochemical mixture of borylated products. The ratio of steric to electronic products was determined by $^{19}$F NMR spectroscopy and GC-FID.

Borylation of 2-chloro-6-fluorotoluene

2-Chloro-6-fluorotoluene was borylated using the general procedure described above, using di(pyridin-2-yl) methane as the ligand. The reaction was carried out for 96 h, affording a 76:24 ratio of 2-(3-chloro-5-fluoro-4-methylphenyl)-4,4,5,5-tetramethyl-1,3,2-dioxaborolane (steric product) and 2-(4-chloro-2-fluoro-3-methylphenyl)-4,4,5,5-tetramethyl-1,3,2-dioxaborolane (electronic product) as a white solid (49.3 mg, 91% based on boron).

For 2-(3-chloro-5-fluoro-4-methylphenyl)-4,4,5,5-tetramethyl-1,3,2-dioxaborolane (major): $^1$H NMR (500 MHz, acetone-d$_6$) δ 7.51 (s, 1H), 7.30 (d, J=9.3 Hz, 1H), 2.31 (d, J=2.5 Hz, 3H), 1.34 (s, 12H); $^{19}$F NMR (470 MHz, acetone-d$_6$) δ −115.0 (dt, J=9.3, 2.5 Hz); $^{13}$C NMR (125 MHz, acetone-d$_6$) δ 162.3 (d, J=247.0 Hz), 136.5 (d, J=4.8 Hz), 132.0 (d, J=2.9 Hz), 128.4 (d, J=20.0 Hz), 120.2, (d, J=21.9 Hz), 85.3, 25.2, 12.2 (d, J=4.3 Hz).

For 2-(4-chloro-2-fluoro-3-methylphenyl)-4,4,5,5-tetramethyl-1,3,2-dioxaborolane (minor): $^1$H NMR (500 MHz, acetone-d$_6$) δ 7.51 (m, 1H), 7.23 (d, J=8.3 Hz, 1H), 2.23 (d, J=2.5 Hz, 3H), 1.34 (s, 12H); $^{19}$F NMR (470 MHz, acetone-d$_6$) δ −102.4 (m); $^{13}$C NMR (125 MHz, acetone-d$_6$) δ 166.9 (d, J=252.7 Hz), 136.9 (d, J=6.7 Hz), 135.8 (d, J=9.5 Hz), 126.0 (d, J=3.8 Hz), 125.0 (d, J=21.0 Hz), 84.8, 25.2, 11.8 (d, J=4.8 Hz).

Borylation of 2-chloro-6-fluoro-N,N-dimethylaniline

2-Chloro-6-fluoro-N,N-dimethylaniline was borylated using the general procedure described above, using 4,4'-di-tert-butyl-2,2'-bipyridine as the ligand. The reaction was carried out for 6 h, affording a 69:31 ratio of 2-chloro-6-fluoro-N,N-dimethyl-4-(4,4,5,5-tetramethyl-1,3,2-dioxaborolan-2-yl)aniline (steric product) and 6-chloro-2-fluoro-N,N-dimethyl-3-(4,4,5,5-tetramethyl-1,3,2-dioxaborolan-2-yl)aniline (electronic product) as a colorless oil (53.8 mg, 90% based on boron).

For 2-chloro-6-fluoro-N,N-dimethyl-4-(4,4,5,5-tetramethyl-1,3,2-dioxaborolan-2-yl)aniline (major): $^1$H NMR (500 MHz, CDCl$_3$) δ 7.51 (s, 1H), 7.28 (d, J=12.2 Hz, 1H), 2.83 (d, J=2.5 Hz, 6H), 1.26 (s, 12H); $^{19}$F NMR (470 MHz, CDCl$_3$) δ −120.2 (d, J=11.6 Hz).

For 6-chloro-2-fluoro-N,N-dimethyl-3-(4,4,5,5-tetramethyl-1,3,2-dioxaborolan-2-yl)aniline (minor): $^1$H NMR (500 MHz, CDCl$_3$) δ 7.31 (dd, J=7.8, 5.9 Hz, 1H), 7.08 (d, J=7.8 Hz, 1H), 2.79 (d, J=2.5 Hz, 6H), 1.30 (s, 12H); $^{19}$F NMR (470 MHz, CDCl$_3$) δ −108.4 (br).

For the mixture: $^{13}$C NMR (125 MHz, CDCl$_3$) δ 165.4 (d, J=255.6 Hz), 159.7 (d, J=250.8 Hz), 140.4 (d, J=12.4 Hz), 137.7 (d, J=16.2 Hz), 137.0 (d, J=7.6 Hz), 132.0 (d, J=2.9 Hz), 131.9, 131.8 (d, J=10.5 Hz), 125.3 (d, J=3.8 Hz), 121.0 (d, J=20.0 Hz), 84.1, 83.9, 43.4 (d, J=4.5 Hz), 43.2 (d, J=4.8 Hz), 24.7.

Borylation of 1-chloro-2-ethoxy-3-fluorobenzene

1-Chloro-2-ethoxy-3-fluorobenzene was borylated using the general procedure described above, using 4,4'-di-tert-butyl-2,2'-bipyridine as the ligand. The reaction was carried out for 12 h, affording a 64:36 ratio of 2-(3-chloro-4-ethoxy-5-fluorophenyl)-4,4,5,5-tetramethyl-1,3,2-dioxaborolane (steric product) and 2-(4-chloro-3-ethoxy-2-fluorophenyl)-4,4,5,5-tetramethyl-1,3,2-dioxaborolane (electronic product) as a colorless oil (53.5 mg, 89% based on boron).

For 2-(3-chloro-4-ethoxy-5-fluorophenyl)-4,4,5,5-tetramethyl-1,3,2-dioxaborolane (major): $^1$H NMR (500 MHz, acetone-d$_6$) δ 7.52 (s, 1H), 7.37 (m, 1H), 4.22 (q, J=6.9 Hz, 2H), 1.38 (t, J=6.9 Hz, 3H, overlapping with the other isomer), 1.33 (s, 12H); $^{19}$F NMR (470 MHz, acetone-d$_6$) δ −129.3 (d, J=10.0 Hz).

For 2-(4-chloro-3-ethoxy-2-fluorophenyl)-4,4,5,5-tetramethyl-1,3,2-dioxaborolane (minor): $^1$H NMR (500 MHz, acetone-d$_6$) δ 7.37 (m, 1H), 7.24 (dd, J=8.3, 1.4 Hz, 1H), 4.14 (q, J=6.9 Hz, 2H), 1.38 (t, J=6.9 Hz, 3H), 1.34 (s, 12H); $^{19}$F NMR (470 MHz, acetone-d$_6$) δ −117.9 (d, J=5.0 Hz).

For the mixture: $^{13}$C NMR (125 MHz, acetone-d$_6$) δ 161.5 (d, J=254.2 Hz), 156.8 (d, J=248.9 Hz), 146.7 (d, J=13.9 Hz), 144.3 (d, J=15.7 Hz), 132.8 (d, J=3.8 Hz), 132.4 (d, J=3.1 Hz), 131.6 (d, J=9.1 Hz), 126.1 (d, J=3.6 Hz), 121.7 (d, J=18.1 Hz), 85.3, 84.9, 70.9 (d, J=5.1 Hz), 70.8 (d, J=4.3 Hz), 25.2, 25.0, 15.9, 15.9.

Borylation of 1,2-dichloro-3-fluorobenzene 1,2-Dichloro-3-fluorobenzene was borylated using the general procedure described above, using 4,4'-di-tert-butyl-2,2'-bipyridine as the ligand. The reaction was carried out for 6 h, affording a 60:40 ratio of 2-(3,4-dichloro-5-fluorophenyl)-4,4,5,5-tetramethyl-1,3,2-dioxaborolane (steric product) and 2-(3,4-dichloro-2-fluorophenyl)-4,4,5,5-tetramethyl-1,3,2-dioxaborolane (electronic product) as a white solid (54.5 mg, 94% based on boron).

For 2-(3,4-dichloro-5-fluorophenyl)-4,4,5,5-tetramethyl-1,3,2-dioxaborolane (major): $^1$H NMR (500 MHz, CD$_3$CN) δ 7.53 (s, 1H), 7.34 (dd, J=8.8, 1.5 Hz, 1H), 1.28 (s, 12H); $^{19}$F NMR (470 MHz, CD$_3$CN) δ −120.0 (d, J=8.3 Hz); $^{13}$C NMR (125 MHz, CD$_3$CN) δ 159.4 (d, J=250.8 Hz), 134.3, 132.2 (d J=2.9 Hz), 123.8 (d, J=20.0 Hz), 120.8 (d, J=20.0 Hz), 85.7, 25.2.

For 2-(3,4-dichloro-2-fluorophenyl)-4,4,5,5-tetramethyl-1,3,2-dioxaborolane (minor): $^1$H NMR (500 MHz, CD$_3$CN) δ 7.48 (dd, J=7.8, 5.9 Hz, 1H), 7.25 (dd, J=7.8, 1.0 Hz, 1H), 1.30 (s, 12H); $^{19}$F NMR (470 MHz, CD$_3$CN) δ −100.7 (d, J=5.0 Hz); $^{13}$C NMR (125.72 MHz, CD$_3$CN) δ 163.4 (d, J=254.6 Hz), 137.5, 135.5 (d, J=9.5 Hz), 126.6 (d, J=3.8 Hz), 121.1 (d, J=21.9 Hz), 85.4, 25.2.

Borylation of 1-chloro-2,3-difluorobenzene

1-Chloro-2,3-difluorobenzene was borylated using the general procedure described above, using 4,4'-di-tert-butyl-2,2'-bipyridine as the ligand. The reaction was carried out for 12 h, affording a 55:45 ratio of 2-(3-chloro-4,5-difluorophenyl)-4,4,5,5-tetramethyl-1,3,2-dioxaborolane (steric product) and 2-(4-chloro-2,3-difluorophenyl)-4,4,5,5-tetramethyl-1,3,2-dioxaborolane (electronic product) as a white solid (50.5 mg, 92% based on boron).

For 2-(3-chloro-4,5-difluorophenyl)-4,4,5,5-tetramethyl-1,3,2-dioxaborolane (major): $^1$H NMR (500 MHz, CDCl$_3$) δ 7.58 (dt, J=6.9, 1.5 Hz, 1H), 7.46 (m, 1H), 1.31 (s, 12H); $^{19}$F NMR (470 MHz, CD$_3$CN) δ −134.5 (m, 1F), −135.9 (dd, J=21.6, 10.0 Hz, 1F).

For 2-(4-chloro-2,3-difluorophenyl)-4,4,5,5-tetramethyl-1,3,2-dioxaborolane (minor): $^1$H NMR (500 MHz, CDCl$_3$) δ 7.38 (m, 1H), 7.13 (m, 1H), 1.33 (s, 12H); $^{19}$F NMR (470 MHz, CD$_3$CN) δ −125.5 (dd, J=21.6, 5.0 Hz, 1F), −139.9 (dd, J=20.7, 5.8 Hz, 1F).

For the mixture: $^{13}$C NMR (125 MHz, CDCl$_3$) δ 155.0 (dd, J=255.7, 11.6 Hz), 150.7 (dd, J=251.9, 12.0 Hz), 149.0 (dd, J=254.5, 14.7 Hz), 147.1 (dd, J=251.3, 16.5 Hz), 131.8 (d, J=3.3 Hz), 130.6 (dd, J=8.1, 5.2 Hz), 125.6 (dd, J=14.4, 1.8 Hz), 125.1, (dd, J=3.7, 1.5 Hz), 122.3 (d, J=14.3 Hz), 121.5 (d, J=15.7 Hz), 84.6, 84.4, 24.8, 24.8.

Borylation of 1-chloro-2-ethoxy-3-fluorobenzene

The scheme below illustrates the reaction methodology employed for the borylation of 1-chloro-2-ethoxy-3-fluorobenzene.

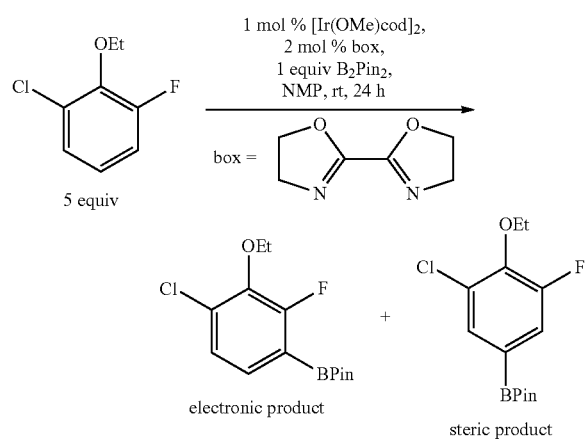

In a nitrogen atmosphere glovebox, [Ir(OMe)cod]$_2$ (33.1 mg, 0.05 mmol) was placed in a 20 mL vial. The solid was partially dissolved in N-methylpyrrolidin-2-one (NMP; 1 mL) and transferred to a 10 mL volumetric flask. The remaining residue in the vial was treated with NMP (4×1 mL), and the resulting solutions were transferred to the volumetric flask. The mixture was then diluted with NMP up to the 10 mL mark resulting in a 0.005 M [Ir(OMe)cod]$_2$ stock solution. 4,4',5,5'-Tetrahydro-2,2'-bioxazole (box; 14.0 mg, 0.1 mmol) was placed in a 20 mL vial. The solid was partially dissolved in NMP (1 mL) and transferred to a 10 mL volumetric flask. The remaining residue in the vial was treated with NMP (4×1 mL), and the resulting solutions were transferred to the volumetric flask. The mixture was diluted with NMP up to the 10 mL mark resulting in a 0.01 M box stock solution.

To a 20 mL glass vial fitted with a micro stir bar and containing B$_2$Pin$_2$ (254 mg, 1.0 mmol) were added the [Ir(OMe)cod]$_2$ stock solution (2.0 mL, 0.01 mmol [Ir(OMe)cod]$_2$) and the box stock solution (2.0 mL, 0.02 mmol box). The mixture was stirred for 30 minutes (min). 1-Chloro-2-ethoxy-3-fluorobenzene (750 µL, 5 mmol) was added. The reaction was stirred for 24 hours (h) at room temperature (rt). Gas chromatograph-mass spectrometry (GC-MS) analysis showed full consumption of B$_2$Pin$_2$. GC-FID showed a 65:35 ratio of the electronic:steric product. The crude reaction mixture was stirred with water (20 mL) and extracted with diethyl ether (Et$_2$O; 3×5 mL). The ethereal phase was dried over magnesium sulfate (MgSO$_4$), filtered, and the solvent was removed under reduced pressure. The residue was purified by Kugelrohr distillation (2 mmHg). The first fraction (rt) was starting 1-chloro-2-ethoxy-3-fluorobenzene, isolated as a colorless oil (afforded 411 mg, 47% based on substrate). The second fraction (~100° C.) contained a mixture of 2-(4-chloro-3-ethoxy-2-fluorophenyl)-4,4,5,5-tetramethyl-1,3,2-dioxaborolane and 2-(3-chloro-4-ethoxy-5-fluorophenyl)-4,4,5,5-tetramethyl-1,3,2-dioxaborolane ($^{19}$F NMR ratio 66:34 electronic:steric product, GC-FID ratio 66:34 electronic:steric product), as a colorless oil (152 mg, 25.3% based on boron).

For 2-(3-chloro-4-ethoxy-5-fluorophenyl)-4,4,5,5-tetramethyl-1,3,2-dioxaborolane (minor): $^1$H NMR (500 MHz, acetone-d$_6$) δ 7.52 (s, 1H), 7.37 (m, 1H, overlapping with the other isomer), 4.22 (q, J=6.9 Hz, 2H), 1.38 (t, J=6.9 Hz, 3H, overlapping with the other isomer), 1.33 (s, 12H, overlapping with the other isomer); $^{19}$F NMR (470 MHz, acetone-d$_6$) δ −129.3 (d, J=10.0 Hz).

For 2-(4-chloro-3-ethoxy-2-fluorophenyl)-4,4,5,5-tetramethyl-1,3,2-dioxaborolane (major): $^1$H NMR (500 MHz, acetone-d$_6$) δ 7.37 (m, 1H, overlapping with the other isomer), 7.24 (dd, J=8.3, 1.4 Hz, 1H), 4.14 (q, J=6.9 Hz, 2H), 1.38 (t, J=6.9 Hz, 3H, overlapping with the other isomer), 1.34 (s, 12H, overlapping with the other isomer); $^{19}$F NMR (470 MHz, acetone-d$_6$) δ −117.9 (d, J=5.0 Hz).

For the mixture: $^{13}$C NMR (125 MHz, acetone-d$_6$) δ 161.5 (d, J=254.2 Hz), 156.8 (d, J=248.9 Hz), 146.7 (d, J=13.9 Hz), 144.3 (d, J=15.7 Hz), 132.8 (d, J=3.8 Hz), 132.4 (d, J=3.1 Hz), 131.6 (d, J=9.1 Hz), 126.1 (d, J=3.6 Hz), 121.7 (d, J=18.1 Hz), 85.3, 84.9, 70.9 (d, J=5.1 Hz), 70.8 (d, J=4.3 Hz), 25.2, 25.0, 15.9, 15.9.

Borylation of 1,2-dichloro-3-fluorobenzene and 2-chloro-6-fluorotoluene Under Varied Conditions To further evaluate the borylation methods described above, 1,2-dichloro-3-fluorobenzene and 2-chloro-6-fluorotoluene were borylated using the general methods described above using various ligands. The scheme below illustrates the reaction methodology employed for the borylation of 1,2-dichloro-3-fluorobenzene and 2-chloro-6-fluorotoluene.

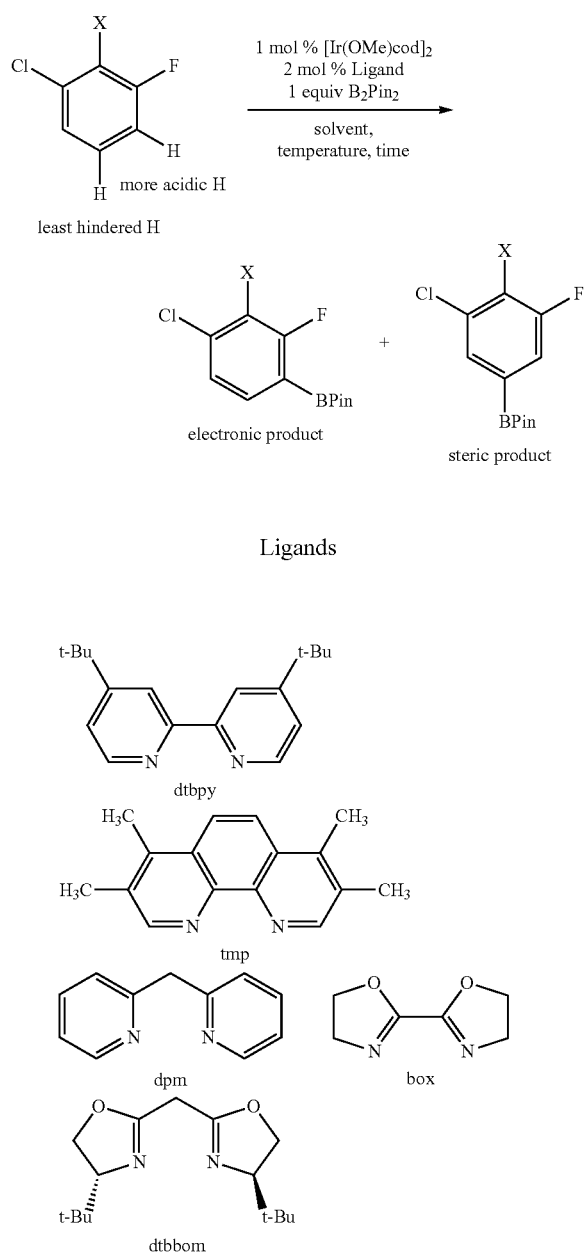

Ligands

The results of these trials are summarized in Table 1. As shown in Table 1, the electronic product could be favored by employing an electron-deficient ligand, such as 4,4',5,5'-tetrahydro-2,2'-bioxazole (box), in the borylation reaction. Analysis of the borylation reactions also suggested that the electronic product could be favored by employing a ligand with less steric bulk in the borylation reaction.

TABLE 1

Results of borylation reactions performed on 1,2-dichloro-3-fluorobenzene and 2-chloro-6-fluorotoluene using various ligands.

| Entry | X | Ligand | Solvent | T (° C.) | t (h) | Conversion[a] | st/ele |
|---|---|---|---|---|---|---|---|
| 1 | Cl | tmp | THF | 80 | 6 | 100% | 64:36 |
| 2 | Cl | dpm | THF | 80 | 6 | 100% | 65:35 |
| 3 | Cl | box | THF | 80 | 12 | 38% | 47:53 |
| 4 | Me | dpm | THF | 80 | 96 | 100% | 76:24 |
| 5 | Me | box | THF | 80 | 12 | 40% | 50:50 |
| 6 | Me | dtbbom | THF | 80 | 96 | 50% | 76:24 |
| 7 | Me | dtbpy | THF | 80 | 12 | 100% | 73:27 |
| 8 | Cl | box | NMP | 80 | 12 | 26% | 36:64 |

[a]Conversion based on boron atoms.

Borylation of 2-Chloro-6-fluorobenzonitrile

The scheme below illustrates the reaction methodology employed for the borylation of 2-chloro-6-fluorobenzonitrile.

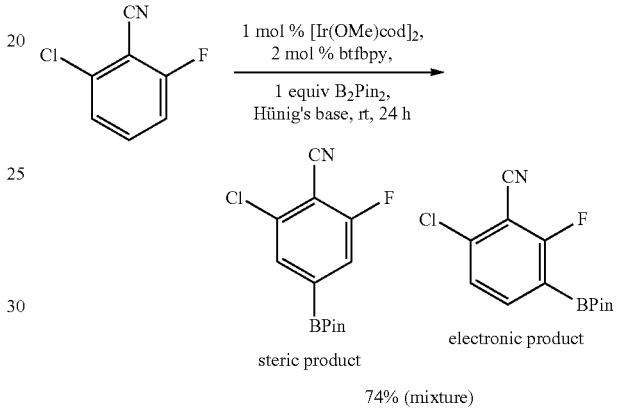

74% (mixture)

In a nitrogen atmosphere glovebox, B₂Pin₂ (127 mg, 0.5 mmol) and [Ir(OMe)cod]₂ (3.3 mg, 0.005 mmol) were dissolved in Hünig's base (2 mL) in a 20 mL vial containing a stir bar. 4,4'-Bis(trifluoromethyl)-2,2'-bipyridine (btfbpy; 2.9 mg, 0.01 mmol) was added. The resulting solution was stirred at rt for 1 h. 2-Chloro-6-fluorobenzonitrile (77.5 mg, 0.5 mmol) was added. The reaction was stirred at rt for 24 h. GC-MS showed no substrate left and formation of two monoborylated products. The volatiles were removed by rotary evaporation. The residue was stirred with water (10 mL) and Et₂O (2 mL). The ether phase was separated, and the water phase was extracted with Et₂O (approximately 2×2 mL). The combined ether solution was dried over MgSO₄, and the solvent was removed by rotary evaporation.

The residue was purified by Kugelrohr distillation to give a regiochemical mixture of borylated products in a 41:59 ratio of 2-chloro-6-fluoro-4-(4,4,5,5-tetramethyl-1,3,2-dioxaborolan-2-yl)benzonitrile (steric product) and 6-chloro-2-fluoro-3-(4,4,5,5-tetramethyl-1,3,2-dioxaborolan-2-yl) benzonitrile (electronic product) as a white solid (105.1 mg, 74% based on arene).

For 2-chloro-6-fluoro-4-(4,4,5,5-tetramethyl-1,3,2-dioxaborolan-2-yl)benzonitrile (minor): $^1$H NMR (500 MHz, CDCl₃) δ 7.67 (s, 1H), 7.47 (d, J=8.3 Hz, 1H), 1.32 (s, 12H); $^{19}$F NMR (470 MHz, CD₃CN) δ −104.2 (d, J=7.8 Hz).

For 6-chloro-2-fluoro-3-(4,4,5,5-tetramethyl-1,3,2-dioxaborolan-2-yl)benzonitrile (major): $^1$H NMR (500 MHz, CDCl₃) δ 7.86 (dd, J=8.3, 6.4 Hz, 1H), 7.31 (d, J=8.3 Hz, 1H), 1.31 (s, 12H); $^{19}$F NMR (470 MHz, CD₃CN) δ −92.2 (d, J=4.2 Hz).

For the mixture: $^{13}$C NMR (125 MHz, CDCl₃) δ 167.8 (d, J=266.8 Hz), 163.1 (d, J=263.0 Hz), 141.4 (d, J=10.3 Hz), 140.6 (d, J=2.1 Hz), 137.2, 131.1 (d, J=3.3 Hz), 125.2 (d, J=3.6 Hz), 119.7 (d, J=18.1 Hz), 111.3 (d, J=2.1 Hz), 104.9 (d, J=18.1 Hz), 103.1 (d, J=20.3 Hz), 85.1, 84.7, 24.8, 24.7.

High-Throughput Substrate/Ligand Screening

Analysis of the borylation reactions above suggested that the electronic product could be favored by employing an electron-deficient ligand, such as 4,4'-bis(trifluoromethyl)-2,2'-bipyridine (btfbpy), 4,4',5,5'-tetrakis(trifluoromethyl)-2,2'-bipyridine (ttfbpy), or 4,4',5,5'-tetrahydro-2,2'-bioxazole (box), in the borylation reaction. Analysis of the borylation reactions above also suggested that the electronic product could be favored by employing a ligand with less steric bulk in the borylation reaction.

Two electron-deficient bipyridine ligands (i.e., two bipyridines containing electron-withdrawing substituents) were further evaluated using a high-throughput screening assay. The scheme below illustrates the borylation reaction conditions used to evaluate substrate/ligand pairs in the high-throughput screening assay.

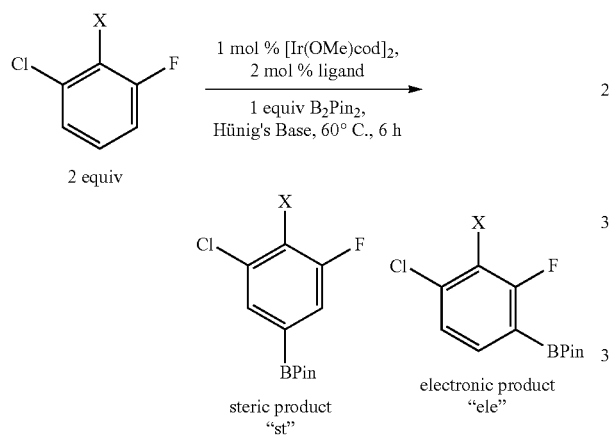

Ligand:

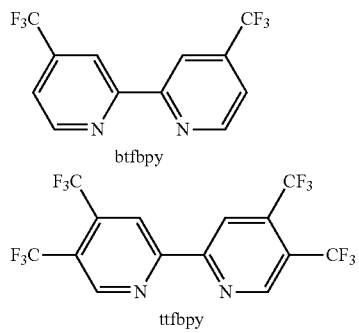

In a nitrogen atmosphere glovebox, $B_2Pin_2$ (423.3 mg, 1.67 mmol), [Ir(OMe)cod]$_2$ (11.1 mg, 0.0167 mmol), and ligand (btfbpy (9.7 mg, 0.0332 mmol) or ttfbpy (14.3 mg, 0.0332 mmol)) were placed in a 20 mL vial. The solids were partially dissolved in Hünig's base (1 mL) and transferred to a 10 mL volumetric flask. The remaining residues in the vial were treated with of Hünig's base (4×1 mL), and the resulting solutions were transferred to the volumetric flask. The mixture was diluted with Hünig's base up to the 10 mL mark. A micro stir bar was added to the flask, and the mixture was stirred at rt for 1 h to afford a stock solution of $B_2Pin_2$/Ir/ligand. To a 700 μL glass vial fitted with a micro stir bar and containing the substrate (1-chloro-3-fluoro-2-substituted benzene, substituted at the 2-position with —CH$_3$, —NMe$_2$, —OEt, —Cl, —F, or —CN; 0.1 mmol) was added the $B_2Pin_2$/Ir/ligand stock solution (300 μL, 50.0 μmol $B_2Pin_2$, 0.50 mmol [Ir(OMe)cod]$_2$, 1.0 μmol ligand). Each vial prepared in this way was placed in a 24-well high-throughput screening block. The block was sealed, removed from the glovebox and heated on a heating plate with magnetic stirring at 60° C. for 12 h. At the time, sample aliquots were taken from each vial, and the conversions and steric/electronic products ratios were determined by $^{19}$F NMR spectroscopy and GC-FID.

The results of the high-throughput screening are shown in Table 2. In most cases, borylation of 1-chloro-3-fluoro-2-substituted benzenes ortho to the fluoro substituent (the electronically favored reaction product) was favored.

TABLE 2

Results of high-throughput substrate/ligand screening.

| | GC-FID st/ele ratio | | $^{19}$F NMR conversion[a] | | $^{19}$F NMR st/ele ratio | |
|---|---|---|---|---|---|---|
| X | btfbpy | ttfbpy | btfbpy | ttfbpy | btfbpy | ttfbpy |
| CH$_3$ | 41:59 | 53:47 | 28% | 12% | 42:58 | 52:48 |
| NMe$_2$ | 48:52 | 45:55 | 45% | 12% | 48:52 | 43:57 |
| OEt | 37:63 | 32:68 | 49% | 32% | 35:65 | 32:68 |
| Cl | 34:66 | 31:69 | 57% | 77% | 35:65 | 32:68 |
| F | 22:78 | 18:82 | 57% | 64% | 21:79 | 18:82 |
| CN | 39:61 | 33:67 | 63% | 74% | 37:63 | 33:67 |

[a]Based on boron atoms

Example 2

Tandem Borylation/Suzuki Coupling of 1-Chloro-3-fluoro-2-substituted Benzenes

Borylated arenes can be valuable synthetic intermediates. For example, borylated arenes can participate in a variety of cross-coupling reactions, such as Suzuki-type cross-coupling reactions, providing access to a wide range of highly functionalized organic compounds. Accordingly, the compatibility of the borylation methodologies described herein with subsequent Suzuki cross-coupling was investigated.

Tandem C—H activation/borylation and Suzuki coupling of 1,2-dichloro-3-fluorobenzene

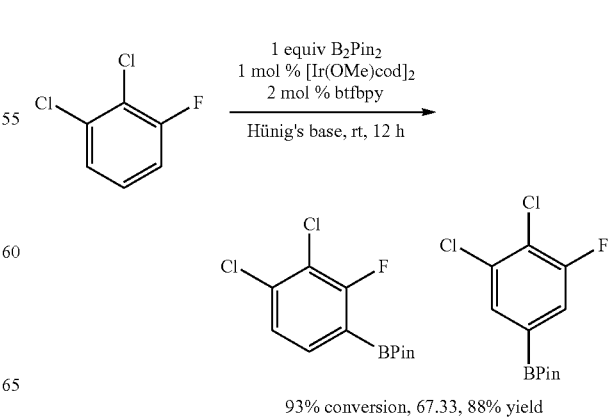

93% conversion, 67:33, 88% yield

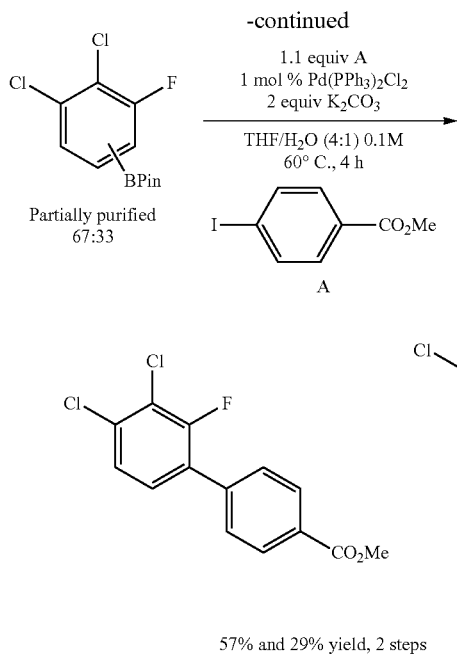

57% and 29% yield, 2 steps

In a nitrogen glovebox, B₂Pin₂ (254 mg, 1.0 mmol), [Ir(OMe)cod]₂ (6.6 mg, 0.010 mmol, 0.02 mmol Ir), btfbpy (6.3 mg, 0.020 mmol) and 1,2-dichloro-3-fluorobenzene (117 µL, 1.0 mmol) were dissolved in THF (2 mL) in a 20 mL vial and stirred at 60° C. for 12 h. ¹⁹F NMR analysis of the crude reaction mixture showed 93% conversion to a 67:33 ratio of the products. The solvent was removed by rotary evaporation. Kugelrohr distillation (0.2 mmHg, 150° C.) provided a mixture of 2-(3,4-dichloro-2-fluorophenyl)-4,4,5,5-tetramethyl-1,3,2-dioxaborolane and 2-(3,4-dichloro-5-fluorophenyl)-4,4,5,5-tetramethyl-1,3,2-dioxaborolane solid, (256 mg, 88%, 67:33 ratio).

Methyl 4-iodobenzoate (228 mg, 0.87 mmol), K₂CO₃ (218 mg, 1.58 mmol) and bis(triphenylphosphine)palladium (II) dichloride (Pd(PPh₃)₂Cl₂; 5.5 mg, 0.008 mmol) were weighed into a screw-capped tube with a stir bar. Water (1.6 mL) was added to dissolve the K₂CO₃, and a solution of the mixture of 2-(3,4-dichloro-2-fluorophenyl)-4,4,5,5-tetramethyl-1,3,2-dioxaborolane and 2-(3,4-dichloro-5-fluorophenyl)-4,4,5,5-tetramethyl-1,3,2-dioxaborolane (232 mg, 0.80 mmol combined, 67:33) in THF (6.4 mL) was added to the screw-capped tube. The biphasic mixture was sparged with argon for 30 min, and the tube was capped and heated in an oil bath at 60° C. After 4 h, GC-MS analysis showed a small amount of iodide, no starting boronate esters, and a overlapped peak of Suzuki coupling products. ¹⁹F NMR analysis of the crude reaction mixture showed a 68:32 ratio of the two Suzuki products with 1% unidentified peaks.

The crude reaction mixture was filtered through a short plug of basic alumina, and the plug was washed with EtOAc. The solvents were removed by rotary evaporation. The residue was purified on a silica gel column with a mixture of hexane and Et₂O (50:1) to provide three fractions, methyl 3',4'-dichloro-5'-fluoro-[1,1'-biphenyl]-4-carboxylate (83.7 mg, 33%), methyl 3',4'-dichloro-2'-fluoro-[1,1'-biphenyl]-4-carboxylate (43.6 mg, 17%) and a mixed fraction (56.3 mg, 15%, 7%, 67:33).

Methyl 3',4'-dichloro-2'-fluoro-[1,1'-biphenyl]-4-carboxylate was isolated as a white solid (52.2 mg, 17.4% from starting arene): mp 150-152° C.; ¹H NMR (500 MHz, CDCl₃) δ 8.10 (AABB, observed J=8.5 Hz, 2H), 7.56 (doublet of AABB, observed J=8.5, 1.7 Hz, 2H), 7.34 (m, resolved into dd, coupling constants J=8.5, 1.5 Hz, 1H), 7.28 (t, resolved into dd, coupling constants J=8.6, 7.3 Hz, 1 H), 3.93 (s, 3H); ¹⁹F NMR (470 MHz, CDCl₃) δ −112.9 (dd, resolved into dq, J=7.5, 1.6 Hz); ¹³C NMR (126 MHz, CDCl₃) δ 166.6, 155.8 (d, J=253.2 Hz), 138.6 (d, J=1.9 Hz), 133.7, 129.9, 129.9, 128.8 (d, J=3.1 Hz), 128.4 (d, J=4.1 Hz), 127.8 (d, J=14.1 Hz), 125.6 (d, J=4.3 Hz), 121.7 (d, J=20.7 Hz), 52.3.

Methyl 3',4'-dichloro-5'-fluoro-[1,1'-biphenyl]-4-carboxylate was isolated as a white solid (87.6 mg, 29.3% from starting arene): mp 134-136° C.; ¹H NMR (500 MHz, CDCl₃) δ 8.09 (AABB, observed J=8.5 Hz, 2H), 7.57 (doublet of AABB, observed J=8.5 Hz, 2H), 7.50 (t, J=1.9 Hz, 1H), 7.30 (dd, J=9.4, 2.0 Hz, 1H), 3.93 (s, 3H); ¹⁹F NMR (470 MHz, CDCl₃) δ −109.2 (dd, J=9.5, 1.6 Hz); ¹³C NMR (126 MHz, CDCl₃) δ 166.5, 159.0 (d, J=251.1 Hz), 142.0 (d, J=2.4 Hz), 140.2 (d, J=8.3 Hz), 134.6 (d, J=1.4 Hz), 130.4, 130.2, 126.8, 124.3 (d, J=3.1 Hz), 120.4 (d, J=19.8 Hz), 113.5 (d, J=22.7 Hz), 52.3.

Tandem C—H activation/borylation and Suzuki coupling of 1-chloro-2,3-difluorobenzene

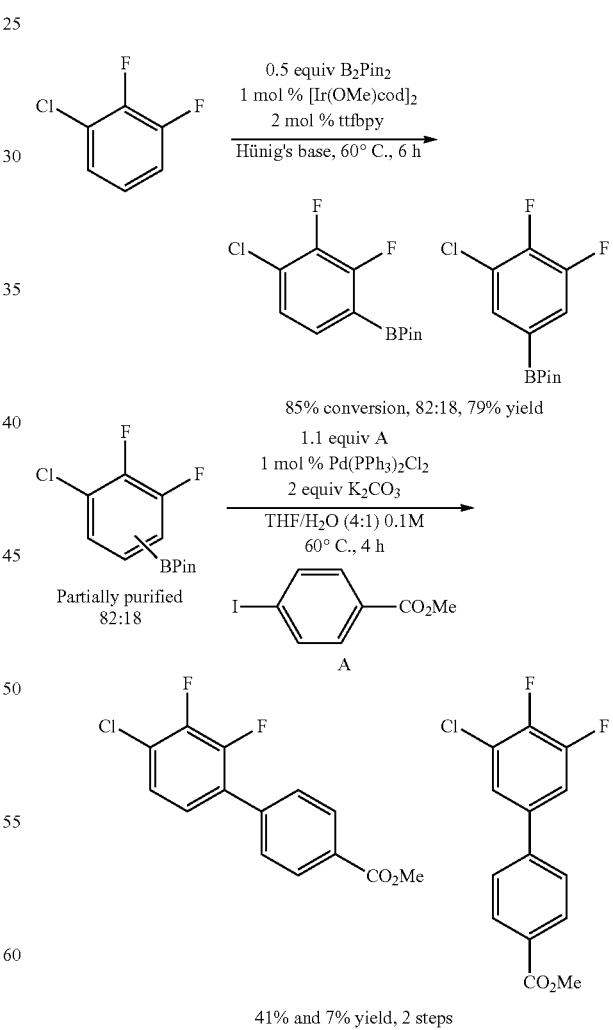

41% and 7% yield, 2 steps

In a nitrogen glovebox, B₂Pin₂ (127 mg, 0.5 mmol), [Ir(OMe)cod]₂ (6.6 mg, 0.01 mmol), and ttfbpy (8.5 mg, 0.02 mmol) were dissolved in Hünig's base (2.0 mL) in a Schlenk flask with a stir bar, and the mixture was stirred for 1 h at rt. 1-Chloro-2,3-difluorobenzene (93 µL, 1.0 mmol) was added. The Schlenk flask was removed from the glovebox, placed under an Argon atmosphere and heated in a 60° C. oil bath for 6 h. $^{19}$F NMR analysis of the crude reaction mixture showed 85% conversion of the starting material and two products in a 82:18 ratio. The solvent was removed by rotary evaporation. Kugelrohr distillation (0.2 mmHg, 150° C.) provided a mixture of 2-(4-chloro-2,3-difluorophenyl)-4,4,5,5-tetramethyl-1,3,2-dioxaborolane and 2-(3-chloro-4,5-difluorophenyl)-4,4,5,5-tetramethyl-1,3,2-dioxaborolane as colorless oil which solidified upon cooling (217 mg, 79%, 82:18 ratio).

Methyl 4-iodobenzoate (228 mg, 0.87 mmol), $K_2CO_3$ (218 mg, 1.58 mmol) and $Pd(PPh_3)_2Cl_2$ (5.5 mg, 0.008 mmol) were weighed into a screw-capped tube with a stir bar. Water (1.6 mL) was added to dissolve the $K_2CO_3$, and a solution of the mixture of 2-(4-chloro-2,3-difluorophenyl)-4,4,5,5-tetramethyl-1,3,2-dioxaborolane and 2-(3-chloro-4,5-difluorophenyl)-4,4,5,5-tetramethyl-1,3,2-dioxaborolane in THF (6.4 mL) was added to the screw-capped tube. The biphasic mixture was sparged with argon for 30 min, and the tube was capped and heated in a 60° C. oil bath. After 4 h, GC-MS analysis showed a small amount of iodide, no starting boronate esters, and a overlapped peak of Suzuki coupling products. $^{19}$F NMR analysis of the crude reaction mixture showed 72% of the Suzuki product of the major boronate ester, 13% of the Suzuki product of the minor boronate ester (ratio of 85:15), and 15% for unidentified peaks.

The crude reaction mixture was filtered through a short plug of basic alumina which was washed with EtOAc. The solvents were removed by rotary evaporation. The residue was purified on a silica gel column with a mixture of hexane and $Et_2O$ (20:1), affording a mixture of methyl 3'-chloro-4',5'-difluoro-[1,1'-biphenyl]-4-carboxylate and methyl 4'-chloro-2',3'-difluoro-[1,1'-biphenyl]-4-carboxylate.

Methyl 3'-chloro-4',5'-difluoro-[1,1'-biphenyl]-4-carboxylate was isolated as a white solid (21 mg, 7% based on 1-chloro-2,3-difluorobenzene): mp 104° C.; $^1$H NMR (500 MHz, CDCl$_3$) δ 8.09 (AA'BB', J=8.6, 2H), 7.55 (AA'BB', J=8.6 Hz, 2H), 7.41 (dt, J=5.9, 2.0 Hz, 1H), 7.31 (ddd, J=10.5, 6.6, 2.2 Hz, 1H), 3.93 (s, 3H); $^{19}$F NMR (470 MHz, CDCl$_3$) δ −137.5 (ddd, J=20.7, 10.7, 2.1 Hz, 1F), −139.2 (dt, J=20.8, 6.2 Hz, 1F); $^{13}$C NMR (126 MHz, CDCl$_3$) δ 166.6, 151.1 (dd, J=251.8, 13.4 Hz), 146.0 (dd, J=251.8, 15.3 Hz), 142.2, 136.8 (dd, J=7.6, 4.8 Hz), 130.3, 129.9, 126.9, 124.2 (d, J=2.9 Hz), 123.2 (dd, J=14.3, 1.9 Hz), 114.6 (d, J=18.1 Hz), 52.3.

Methyl 4'-chloro-2',3'-difluoro-[1,1'-biphenyl]-4-carboxylate was isolated as a white solid (117 mg, 41% based on 1-chloro-2,3-difluorobenzene): mp 101° C.; $^1$H NMR (500 MHz, DMSO-d$_6$) δ 8.08 (AA'BB', J=8.8, 2H), 7.74 (doublet of an AA'BB', J=8.8, 1.6 Hz, 2H), 7.57 (ddd, J=8.7, 6.9, 2.0 Hz, 1H), 7.47 (ddd, J=8.7, 7.3, 2.0 Hz, 1H), 3.89 (s, 3H); $^{19}$F NMR (470 MHz, CDCl$_3$) δ −137.5 (ddd, J=20.5, 6.4, 2.1 Hz, 1F), −139.0 (ddq, J=20.4, 7.0, 1.7 Hz, 1F); $^{13}$C NMR (126 MHz, CDCl$_3$) δ 166.6, 148.5 (dd, J=253.7, 13.4 Hz) 147.7 (dd, J=251.8, 15.3 Hz) 138.3, 130.0, 129.9, 128.8 (d, J=3.8 Hz), 128.7 (d, J=10.5 Hz), 125.2 (d, J=4.8 Hz), 124.6 (t, J=2.9 Hz), 122.2 (d, J=15.3 Hz), 52.3.

Tandem C—H Activation/Borylation and Suzuki Coupling of 2-chloro-6-fluorobenzonitrile

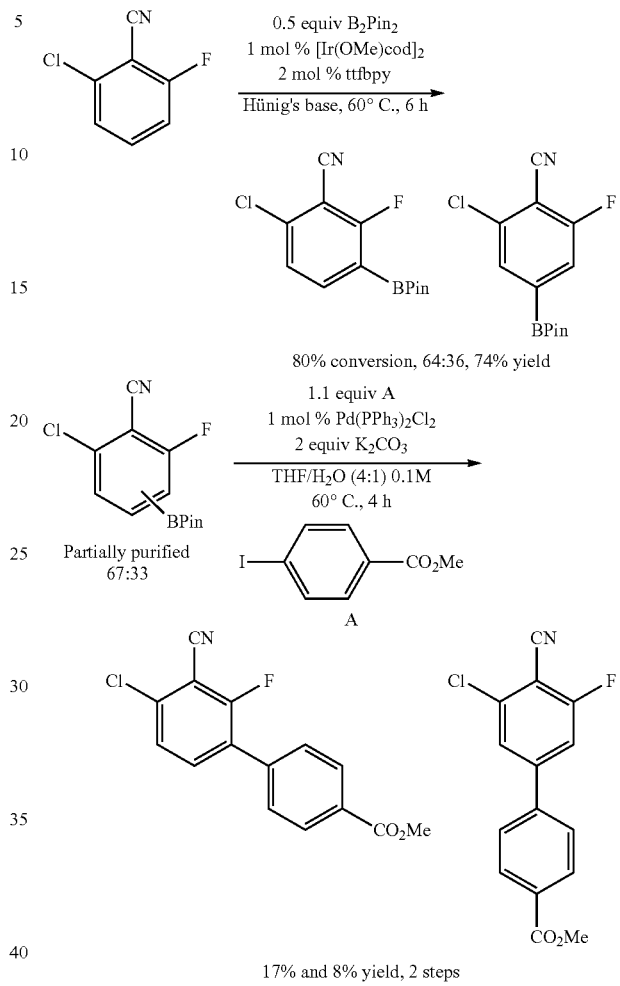

17% and 8% yield, 2 steps

In a nitrogen glovebox, B$_2$Pin$_2$ (127 mg, 0.5 mmol), [Ir(OMe)cod]$_2$ (6.6 mg, 0.01 mmol), and ttfbpy (8.5 mg, 0.02 mmol) were dissolved in Hünig's base (2.0 mL) in a Schlenk flask with a stir bar, and the mixture was stirred for 1 h at rt. 2-Chloro-6-fluorobenzonitrile (156 mg, 1.0 mmol) was added. The Schlenk flask was removed from the glovebox, placed under an Argon atmosphere and heated in a 60° C. oil bath for 6 h. $^{19}$F NMR analysis of the crude reaction showed 80% conversion of the starting material and two products in a 64:36 ratio. The solvent was removed by rotary evaporation. Kugelrohr distillation (0.2 mmHg, 150° C.) provided a mixture of 6-chloro-2-fluoro-3-(4,4,5,5-tetramethyl-1,3,2-dioxaborolan-2-yl)benzonitrile, 2-chloro-6-fluoro-4-(4,4,5,5-tetramethyl-1,3,2-dioxaborolan-2-yl)benzonitrile and starting 2-chloro-6-fluorobenzonitrile as a white solid (213 mg, 64:32:4, 74% borylated products).

Methyl 4-iodobenzoate (213 mg, 0.81 mmol), $K_2CO_3$ (204 mg, 1.48 mmol) and Pd(PPh$_3$)$_2$Cl$_2$ (5.2 mg, 0.0074 mmol) were weighed into a screw-capped tube with a stir bar. Water (1.5 mL) was added to dissolve the $K_2CO_3$, and a solution of the above mixture in THF (6.0 mL) was added to the screw-capped tube. The biphasic mixture was sparged with argon for 30 min, and the tube was capped and heated in a 60° C. oil bath.

After 4 h, GC-MS analysis showed no boronate esters and overlapped peaks for Suzuki coupling products. $^{19}$F NMR analysis of the crude reaction mixture showed 46% of the Suzuki product of the major boronate ester, 22% of the Suzuki product of the minor boronate ester (ratio of 68:32), 13% unborylated arene, and 19% for unidentified peaks.

The crude reaction mixture was filtered through a short plug of basic alumina which was washed with EtOAc. The solvents were removed by rotary evaporation. The residue was purified on a silica gel column with a mixture of hexane and EtOAc (5:1), affording methyl 4'-chloro-3'-cyano-2'-fluoro-[1,1'-biphenyl]-4-carboxylate, methyl 3'-chloro-4'-cyano-5'-fluoro-[1,1'-biphenyl]-4-carboxylate, and a fraction determined to be a mixture of the two products (46 mg, 12% of the first product, 4% of the second product).

Methyl 4'-chloro-3'-cyano-2'-fluoro-[1,1'-biphenyl]-4-carboxylate was isolated as a white solid (49 mg, 17% based on 2-chloro-6-fluorobenzonitrile): mp 209-211° C.; $^1$H NMR (500 MHz, CDCl$_3$) δ 8.14 (AA'BB', J=8.3, 2H), 7.62 (AA'BB', J=8.3 Hz, 2H), 7.56 (t, J=1.5 Hz, 1H), 7.36 (dd, J=9.3, 1.5 Hz, 1H), 3.94 (s, 3H); $^{19}$F NMR (470 MHz, CDCl$_3$) δ −102.2 (dd, J=9.5, 0.8 Hz); $^{13}$C NMR (126 MHz, CDCl$_3$) δ 166.2, 163.9 (d, J=262.3 Hz), 147.2 (d, J=8.6 Hz), 141.1, 138.3 (d, J=2.9 Hz), 131.3, 130.6, 127.2, 124.4 (d, J=2.9 Hz), 113.3 (d, J=20.0 Hz), 111.2, 102.4 (d, J=18.1 Hz), 52.4.

Methyl 3'-chloro-4'-cyano-5'-fluoro-[1,1'-biphenyl]-4-carboxylate was isolated as a white solid (23 mg, 8% based on 2-chloro-6-fluorobenzonitrile): mp 148-150° C.; $^1$H NMR (500 MHz, DMSO-d$_6$) δ 8.18 (AA'BB', J=8.3, 2H), 7.63 (t, J=8.3 Hz, 1H), 7.56 (d of AA'BB', J=8.3, 2.0 Hz, 2H), 7.41 (dd, J=8.3, 1.0 Hz, 1H), 3.94 (s, 3H); $^{19}$F NMR (470 MHz, CDCl$_3$) δ −106.6 (dt, J=8.3, 1.7 Hz); $^{13}$C NMR (126 MHz, CDCl$_3$) δ 166.4, 160.6 (d, J=264.2 Hz), 137.3 (br s), 137.0 (d, J=1.9 Hz), 135.2 (d, J=5.7 Hz), 130.6, 130.1, 128.8 (d, J=2.9 Hz), 127.7 (d, J=13.4 Hz), 126.0 (d, J=3.8 Hz), 111.2, 104.2 (d, J=19.1 Hz), 52.4.

Tandem C—H Activation/Borylation and Suzuki Coupling of 2-chloro-6-fluorotoluene

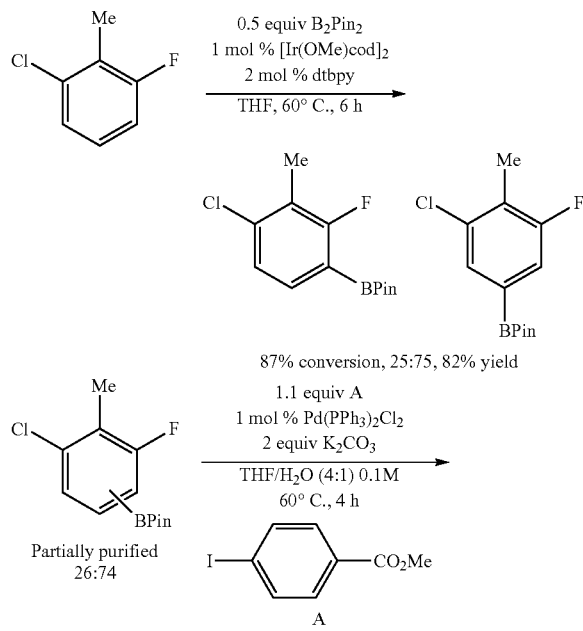

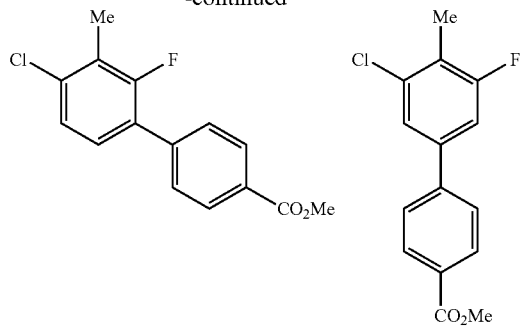

59% combined yield, 14:86

In a nitrogen glovebox, B$_2$Pin$_2$ (127 mg, 0.5 mmol), [Ir(OMe)cod]$_2$ (6.6 mg, 0.01 mmol), and ttfbpy (8.5 mg, 0.02 mmol) were dissolved in THF (2.0 mL) in a Schlenk flask with a stir bar and stirred for 1 h at rt. 2-Chloro-6-fluorotoluene (131 μL, 1.0 mmol) was added. The Schlenk flask was removed from the glovebox and placed under an Argon atmosphere The mixture was heated in a 60° C. oil bath for 6 h. $^{19}$F NMR analysis of the crude reaction mixture showed 87% conversion of the starting material and two products in a 25:75 ratio. The solvent was removed by rotary evaporation. Kugelrohr distillation (0.2 mmHg, 150° C.) provided a mixture of 6-chloro-2-fluoro-3-(4,4,5,5-tetramethyl-1,3,2-dioxaborolan-2-yl)toluene and 2-chloro-6-fluoro-4-(4,4,5,5-tetramethyl-1,3,2-dioxaborolan-2-yl)toluene as a white solid (222 mg, 82%, 26:74).

Methyl 4-iodobenzoate (236 mg, 0.90 mmol), K$_2$CO$_3$ (407 mg, 1.62 mmol) and Pd(PPh$_3$)$_2$Cl$_2$ (5.8 mg, 0.0082 mmol) were weighed into a screw-capped tube with a stir bar. Water (2.0 mL) was added to dissolve the K$_2$CO$_3$, and a solution of the above mixture in THF (8.0 mL) was added to the screw-capped tube. The biphasic mixture was sparged with argon for 30 min, and the tube was capped and heated in a 60° C. oil bath. After 4 h, GC-MS analysis showed no boronate esters and overlapped peaks of Suzuki coupling products. $^{19}$F NMR analysis of the crude reaction mixture showed 16% of the Suzuki product of the electronically-favored boronate ester, 71% of the Suzuki product of the sterically-favored boronate ester (in a ratio of 18:82), and 13% unidentified peaks.

The crude reaction mixture was filtered through a short plug of basic alumina which was washed with EtOAc. The solvents were removed by rotary evaporation. The residue was purified on a silica gel column with a mixture of hexane and EtOAc (5:1). However, the two products came out as one fraction. A mixture of methyl 3'-chloro-5'-fluoro-4'-methyl-[1,1'-biphenyl]-4-carboxylate and methyl 4'-chloro-2'-fluoro-3'-methyl-[1,1'-biphenyl]-4-carboxylate was isolated as a white solid (164 mg, 59% based on substrate, 14:86).

Mixture of methyl 3'-chloro-5'-fluoro-4'-methyl-[1,1'-biphenyl]-4-carboxylate and methyl 4'-chloro-2'-fluoro-3'-methyl-[1,1'-biphenyl]-4-carboxylate: $^1$H NMR (500 MHz, CDCl$_3$) δ 8.08 (d, J=8.3 Hz, 2H overlapping of two products), 7.58 (d, J=8.3 Hz, 2H, the steric product), 7.56 (d, J=8.3 Hz, 2H, the electronic product), 7.42 (s, 1H, the steric product), 7.22-7.18 (m, overlapping), 3.92 (s, 3H, overlapping of two products), 2.36 (d, J=2.0 Hz, 3H, the electronic product), 2.33 (d, J=2.0 Hz, 3H, the steric product); $^{13}$C NMR (126 MHz, CDCl$_3$) δ 166.7, 166.6, 161.5 (d, J=247.0 Hz), 158.0 (d, J=249.9 Hz), 142.9 (d, J=2.9 Hz), 139.8, 139.4 (d, J=9. Hz), 136.0 (d, J=7.6 Hz), 135.2 (d, J=5.7 Hz), 130.2, 129.6, 129.6, 129.3, 128.8 (d, J=2.9 Hz), 127.8 (d, J=3.8 Hz), 126.7, 126.3 (d, J=14.3 Hz), 124.8 (d, J=3.8 Hz), 124.6 (d, J=20.0 Hz), 123.7 (d, J=19.1 Hz), 123.2 (d, J=3.8 Hz), 112.2 (d, J=24.8 Hz), 52.1, 12.5 (d, J=5.7 Hz), 11.7 (d, J=3.8 Hz); $^{19}$F NMR (470 MHz, CDCl$_3$) δ −112.3 (d, J=10.0 Hz, the steric product), −116.4 (m, the electronic product).

Tandem C—H Activation/Borylation and Suzuki Coupling of 2-chloro-6-fluorophenyl 3,5-bis(trifluoromethyl) benzoate

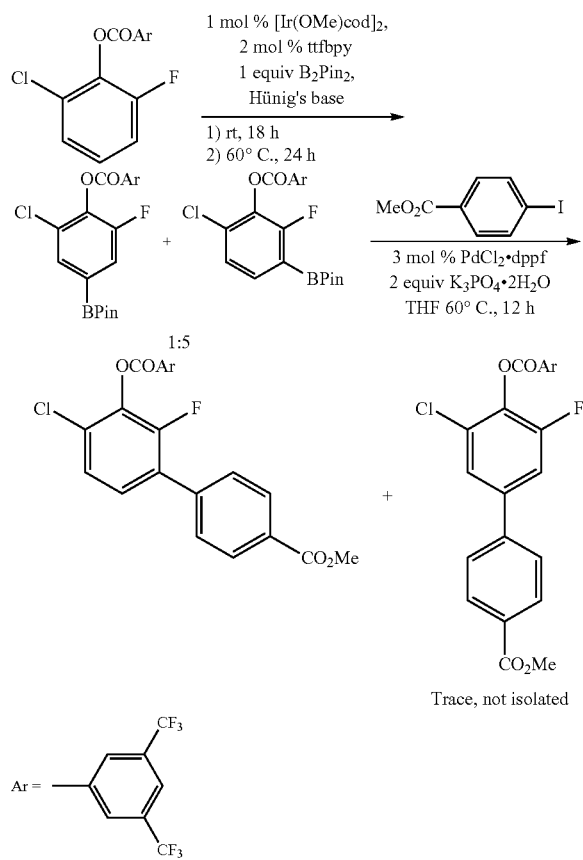

In a nitrogen glovebox, [Ir(OMe)cod]$_2$ (6.6 mg, 0.01 mmol) and B$_2$Pin$_2$ (254 mg, 1.0 mmol) were added to a Schlenk flask. Hünig's base (1.0 mL) was added to the flask. A solution of ttfbpy (8.5 mg, 0.02 mmol) in Hünig's base (1.0 mL) was added. The resulting mixture was stirred at rt for 1 h. The substrate (386 mg, 1.0 mmol) in Hünig's base (1.0 mL) was added to the Schlenk flask, which was removed from the glovebox, fitted with a condenser, and placed under an Argon atmosphere. The reaction mixture was stirred at rt for 18 h. Analysis of an NMR sample taken at 15 h showed no evidence of borylation or formation of the Ar—F byproducts. The reaction mixture was heated in a 60° C. oil bath for 24 h. At this time, NMR spectroscopic analysis indicated that the reaction had proceeded in 59% conversion affording a 17:83 molar ratio of the steric borylation product to the electronic borylation product. The volatiles were then removed by rotary evaporation. The reaction residue was dissolved in Et$_2$O and washed with water. The organic layer was dried over MgSO$_4$, filtered and evaporated.

For 6-chloro-2-fluoro-3-(4,4,5,5-tetramethyl-1,3,2-dioxaborolan-2-yl)phenyl 3,5-bis(trifluoromethyl)benzoate (major): $^1$H NMR (500 MHz, CDCl$_3$) δ 8.64 (s, 2H), 8.15 (s, 1H), 7.62 (dd, J=8.3, 5.9 Hz, 1H), 7.28 (dd, J=8.1, 1.2 Hz, 1H), 1.34 (s, 12H); $^{19}$F NMR (500 MHz, CDCl$_3$) δ −63.1, −115.6.

For 2-chloro-6-fluoro-4-(4,4,5,5-tetramethyl-1,3,2-dioxaborolan-2-yl)phenyl 3,5-bis(trifluoromethyl)benzoate (minor): $^1$H NMR (500 MHz, CDCl$_3$) δ 8.66 (s, 2H), 8.15 (overlapped peak, 1H), 7.72 (t, J=1.2 Hz, 1H), 7.56 (dd, J=9.3, 1.0 Hz, 1H), 1.34 (s, 12H); $^{19}$F NMR (500 MHz, CDCl$_3$) δ −63.1, −126.1.

The crude borylation products were then dissolved in THF (2 mL) and placed in a screw-capped tube containing methyl p-iodobenzoate (185 mg, 0.71 mmol). Potassium phosphate tribasic dihydrate (K$_3$PO$_4$.2H$_2$O; 298 mg, 1.2 mmol) was added and the tube was purged with Argon for 5 min, before [1,1'-bis(diphenylphosphino)ferrocene]dichloropalladium(II) (PdCl$_2$.dppf; 13 mg, 0.018 mmol) was added. The tube was capped and heated in an oil bath at 60° C. for 12 h. GC-MS analysis of the crude reaction mixture showed that the borylated arenes were consumed. The crude reaction mixture was then passed through a short plug of basic alumina washing with Et$_2$O. The filtrate was dried over MgSO$_4$, filtered and evaporated. The residue was purified by silica gel column chromatography eluting with dichloromethane to afford 6-chloro-2-fluoro-3-(4,4,5,5-tetramethyl-1,3,2-dioxaborolan-2-yl)phenyl 3,5-bis(trifluoromethyl)benzoate-coupled product as a white solid (79 mg, 15% (two steps)).

For methyl 3'-((3,5-bis(trifluoromethyl)benzoyl)oxy)-4'-chloro-2'-fluoro-[1,1'-biphenyl]-4-carboxylate: mp 152-154° C.; $^1$H NMR (500 MHz, CDCl$_3$) δ 8.68 (br s, 2H), 8.18 (br s 1H), 8.11 (AABB, J=8.3 Hz, 2H), 7.60 (dd, J=8.3, 1.5 Hz, 2H), 7.41-7.36 (overlapping multiplets, 2H), 3.93 (s, 3H); $^{19}$F NMR (470 MHz, CDCl$_3$) δ −63.0 (s, 6F), −129.1 (dt, J=5.1, 1.7 Hz, 1F); $^{13}$C NMR (125 MHz, CDCl$_3$) δ 166.6, 160.8, 152.2 (d, J=254.6 Hz), 138.3 (d, J=1.7 Hz), 135.8, 135.7, 132.7 (q, J=34.3 Hz), 130.5 (q, J=3.8 Hz), 130.1 (d, J=24.8 Hz), 129.9, 128.9 (d, J=3.1 Hz), 128.4 (d, J=12.4 Hz), 128.2 (d, J=3.6 Hz), 128.1 (d, J=1.4 Hz), 127.6 (m), 125.6 (d, J=4.1 Hz), 122.7 (q, J=273.7 Hz, CF$_3$), 52.3.

Example 3

Tandem Borylation/Dehalogenation of 1-Chloro-4-fluoro-3-substituted- and 1-Bromo-4-fluoro-3-substituted Benzenes Tandem borylation/dehalogenation was also investigated as a strategy for the ortho-borylation of arenes that are substituted with an electron-withdrawing group. The scheme below illustrates the tandem borylation/dehalogenation methodology which was investigated. As discussed above, in the case of arenes that are substituted with an electron-withdrawing group, iridium-catalyzed C—H activation-borylation of the arene is typically governed by steric effects. In tandem borylation/dehalogenation, the substrate can include an electron-withdrawing group and a sacrificial atom (e.g., a halogen such as Cl or Br) positioned para to the electron-withdrawing group, so as to sterically hinder attack of the iridium catalyst at the otherwise sterically favored position meta to the electron-withdrawing group. As a result, iridium-catalyzed C—H activation-borylation of the arene exclusively generates the ortho-borylated (electronic) product. Subsequent dehalogenation can afford exclusively the desired electronic product.

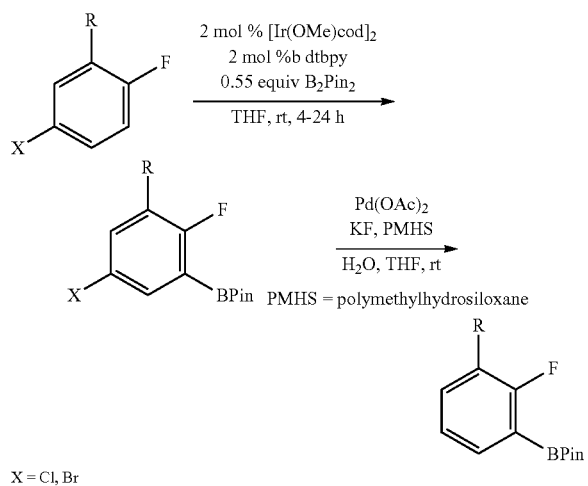

X = Cl, Br

General Procedure for Borylation

In a nitrogen atmosphere glovebox B$_2$Pin$_2$ (140 mg, 0.55 mmol) was weighed into a 20 mL vial containing a magnetic stir bar. [Ir(OMe)cod]$_2$ (6.6 mg, 0.02 mmol) and 4,4'-di-tert-butyl-2,2'-dipyridyl ligand (5.4 mg, 0.02 mmol) were weighed into two separate test tubes, each being diluted with THF (2 mL). The [Ir(OMe)cod]$_2$ solution was transferred into the 20 mL vial containing B$_2$Pin$_2$. This mixture was stirred until a golden yellow clear solution was obtained. The solution containing ligand was transferred into the vial, and the mixture was stirred until it became a dark brown color solution. The substrate (1 mmol) was added to the vial, which was then sealed. The reaction mixture stirred for 24 h at rt, after which the vial was removed from the glovebox. The reaction mixture was passed through a short plug of silica eluting with a 10:1 hexane/EtOAc solution (2×10 mL). The volatiles were removed by rotary evaporation affording the product, which was characterized using standard methodologies.

General Procedure for Hydrodehalogenation

An oven-dried round bottom flask was charged with the borylated arene prepared using the method described above (0.368 g, 1 mmol), Pd(OAc)$_2$ (0.011 g, 0.05 mmol), and freshly distilled THF (5 mL). The round bottom flask was sealed with a septum and flushed with nitrogen. While being flushed, a solution of KF (0.116 g, 2 mmol) in degassed water (2 mL) was introduced by syringe. The nitrogen inlet was removed and a balloon filled with nitrogen was attached to the flask. Polymethylhydrosiloxane (PMHS; 0.24 mL, 4 mmol) was slowly injected drop wise. The final reaction mixture was stirred until $^1$H and $^{19}$F NMR spectral analyses indicated the disappearance of starting material (4 h). The reaction mixture was diluted with Et$_2$O and the layers were separated. The ether layer was filtered through a plug of Celite in a 60 mL syringe. The Celite was flushed with EtOAc. The volatiles were then removed by rotary evaporation affording the product, which was characterized using standard methodologies.

Tandem Borylation/Dehalogenation of 4-bromo-1-fluoro-2-(trifluoromethyl)benzene

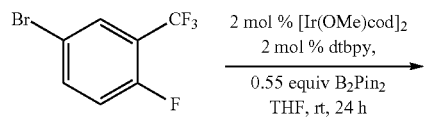

4-Bromo-1-fluoro-2-(trifluoromethyl)benzene was borylated using the general procedure described above. The borylation reaction afforded product as colorless oil (0.229 g, 62%): $^1$H NMR (500 MHz, CDCl$_3$) δ 8.02 (dd, J=2.5, 3.5 Hz, 1H), 7.78 (dd, J=2.5, 6.5 Hz, 1H), 1.36 (s, 12H); $^{13}$C NMR (125 MHz, CDCl$_3$) δ 162.9 (dd, J=1.9, 259.7 Hz), 143.1 (d, J=8.5 Hz), 132.8 (qd, J=1.9, 4.7 Hz), 121.7 (q, J=270.3 Hz), 120.0 (qd, J=33.1, 16.1, Hz), 116.3 (d, J=3.5 Hz), 84.7, 24.8; $^{19}$F NMR (470 MHz, CDCl$_3$) δ 61.9, 106.4; $^{11}$B NMR (160 MHz, CDCl$_3$) δ 29.3 (br s).

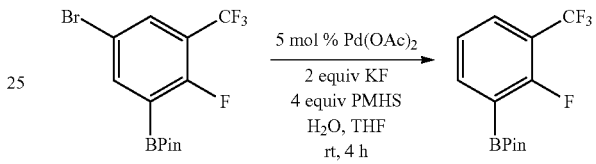

The resulting borylated arene was hydrodehalogenated using the general procedure described above. The hydrodehalogenation reaction afforded the dehalogenated product as a white solid (0.228 g, 79%): mp 76-77° C.; $^1$H NMR (500 MHz, CDCl$_3$) δ 7.93 (ddd, J=1.5, 5.5, 7.0 Hz, 1H), 7.70 (ddd, J=1.5, 6.0, 7.5 Hz, 1H), 7.23 (dd, J=6.5, 8.5 Hz, 1H), 1.37 (s, 12H); $^{13}$C NMR (125 MHz, CDCl$_3$) δ 164.0 (dd, J=1.9, 260.3 Hz), 140.7 (d, J=9.5 Hz), 130.8 (qd, J=2.5, 4.7 Hz), 123.5 (d, J=4.1 Hz), 122.7 (q, J=271.0 Hz), 118.3 (m), 84.3, 24.8; $^{19}$F NMR (470 MHz, CDCl$_3$) δ 61.6, 104.2; $^{11}$B NMR (160 MHz, CDCl$_3$) δ 29.8 (br s).

Tandem Borylation/Dehalogenation of 1-bromo-4-fluoro-2-(trifluoromethyl)benzene

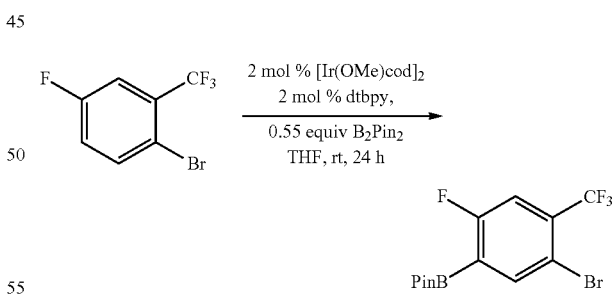

1-Bromo-4-fluoro-2-(trifluoromethyl)benzene was borylated on a 10 mmol scale using the general procedure described above. The borylation reaction afforded the product as a white solid (2.610 g, 71%): mp 66-67° C.; $^1$H NMR (500 MHz, CDCl$_3$) δ 8.03 (d, J=5.5 Hz, 1H), 7.37 (d, J=8.5 Hz, 1H), 1.37 (s, 12H); $^{13}$C NMR (125 MHz, CDCl$_3$) δ 165.4 (d, J=253.1 Hz), 142.8 (d, J=8.5 Hz), 134.0 (qd, J=8.5, 32.2 Hz), 121.9 (q, J=272.2 Hz), 115.6 (m), 113.8, 84.8, 24.8; $^{19}$F NMR (470 MHz, CDCl$_3$) δ 63.5, 102.9; $^{11}$B NMR (160 MHz, CDCl$_3$) δ 29.5 (br s).

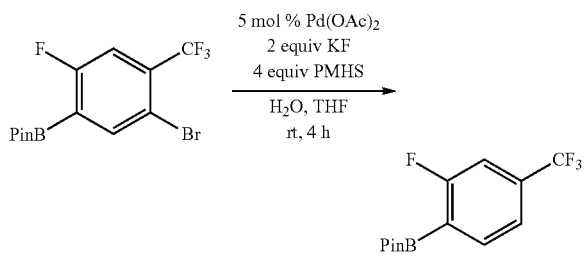

The resulting borylated arene was hydrodehalogenated using the general procedure described above. The hydrodehalogenation reaction afforded the dehalogenated product as a colorless oil (0.232 g, 80%): $^1$H NMR (500 MHz, CDCl$_3$) δ 7.87 (dd, J=6.5, 6.5 Hz, 1H), 7.40 (d, J=8.0 Hz, 1H), 7.30 (d, J=9.0 Hz, 1H), 1.38 (s, 12H); $^{13}$C NMR (125 MHz, CDCl$_3$) δ 166.7 (d, J=251.4 Hz), 137.6 (d, J=8.5 Hz), 135.1 (m), 123.2 (q, J=271.2 Hz), 120.3 (m), 112.3 (m), 84.8, 24.8; $^{19}$F NMR (470 MHz, CDCl$_3$) δ 63.2, 100.6; $^{11}$B NMR (160 MHz, CDCl$_3$) δ 30.1 (br s).

Tandem Borylation/Dehalogenation of 4-bromo-1-fluoro-2-methoxybenzene

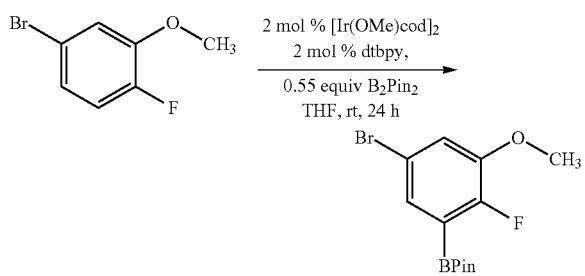

4-Bromo-1-fluoro-2-methoxybenzene was borylated using the general procedure described above. The borylation reaction afforded the product as a white solid (0.283 g, 86%): mp 79-80° C.; $^1$H NMR (500 MHz, CDCl$_3$) δ 7.37 (dd, J=2.5, 4.0 Hz, 1H), 7.14 (dd, J=2.5, 7.5 Hz, 1H), 3.85 (s, 3H), 1.34 (s, 12H); $^{13}$C NMR (125 MHz, CDCl$_3$) δ 155.8 (d, J=251.2 Hz), 148.3 (d, J=13.2 Hz), 129.4 (d, J=7.6 Hz), 119.6 (d, J=2.9 Hz), 116.0 (d, J=3.7 Hz), 84.3, 56.6, 24.8; $^{19}$F NMR (470 MHz, CDCl$_3$) δ 126.6; $^{11}$B NMR (160 MHz, CDCl$_3$) δ 29.7 (br s).

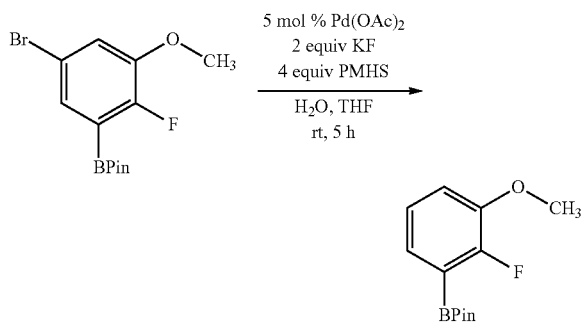

The resulting borylated arene was hydrodehalogenated using the general procedure described above (reaction time of 5 h). The hydrodehalogenation reaction afforded the dehalogenated product as a colorless oil (0.228 g, 91%): $^1$H NMR (500 MHz, acetone-d$_6$) δ 7.23 (m, 2H), 7.12 (dd, J=8.0, 7.5 Hz, 1H), 3.87 (s, 3H), 1.34 (s, 12H); $^{13}$C NMR (125 MHz, acetone-d$_6$) δ 156.5 (d, J=250.4 Hz), 147.7 (d, J=12.4 Hz), 127.0 (d, J=6.6 Hz), 123.9 (d, J=3.9 Hz), 116.7 (d, J=2.9 Hz), 83.7, 55.6, 24.3; $^{19}$F NMR (470 MHz, acetone-d$_6$) δ 125.6; $^{11}$B NMR (160 MHz, (acetone-d$_6$) δ 30.2 (br s).

Tandem Borylation/Dehalogenation of 1-bromo-4-fluoro-2-methoxybenzene

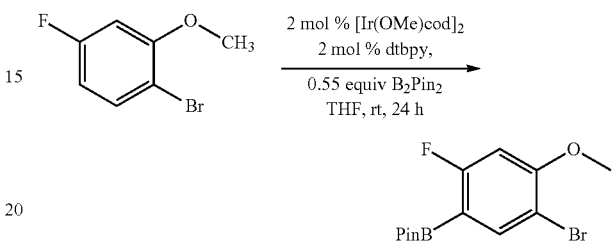

1-Bromo-4-fluoro-2-methoxybenzene was borylated using the general procedure described above. After workup, a white solid was obtained (0.313 g, 95%): mp 104-105° C.; $^1$H NMR (500 MHz, CDCl$_3$) δ 7.89 (d, J=6.5 Hz, 1H), 6.61 (d, J=11.0 Hz, 1H), 3.72 (s, 3H), 1.35 (s, 12H); $^{13}$C NMR (125 MHz, CDCl$_3$) δ 167.6 (d, J=251.2 Hz), 159.5 (d, J=11.4 Hz), 140.2 (d, J=10.4 Hz), 108.3 (d, J=22.7 Hz), 105.9 (d, J=2.9 Hz), 83.9, 56.4, 24.8; $^{19}$F NMR (470 MHz, CDCl$_3$) δ 100.4; $^{11}$13 NMR (160 MHz, CDCl$_3$) δ 29.5 (br s).

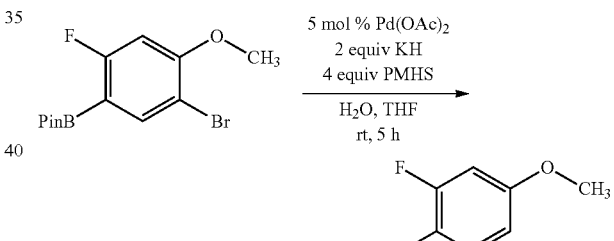

The resulting borylated arene was hydrodehalogenated using the general procedure described above (reaction time of 5 h). The hydrodehalogenation reaction afforded the dehalogenated product as colorless oil (0.152 g, 61%): $^1$H NMR (500 MHz, CDCl$_3$) δ 7.66 (dd, J=7.5, 7.5 Hz, 1H), 6.70 (dd, J=2.5, 8.0 Hz, 1H), 6.58 (dd, J=2.5, 12.0 Hz, 1H), 3.83 (s, 3H), 1.36 (s, 12H); $^{13}$C NMR (125 MHz, CDCl$_3$) δ 168.6 (d, J=249.4 Hz), 163.9 (d, J=11.2 Hz), 137.7 (d, J=10.5 Hz), 109.9 (d, J=2.9 Hz), 101.1 (d, J=27.5 Hz), 83.6, 55.4, 24.8; $^{19}$F NMR (470 MHz, CDCl$_3$) δ 100.5; $^{11}$B NMR (160 MHz, CDCl$_3$) δ 29.9 (br s).

Tandem Borylation/Dehalogenation of 4-chloro-1-fluoro-2-methylbenzene

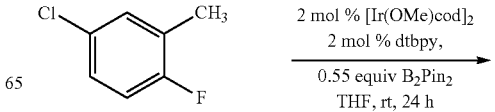

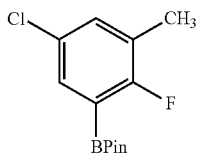

4-Chloro-1-fluoro-2-methylbenzene was borylated using the general procedure described above. After the workup, a white solid ( ) was obtained (0.173 g, 64%): mp 64-65° C.; $^1$H NMR (500 MHz, CDCl$_3$) δ 7.49 (dd, J=3.0, 6.5 Hz, 1H), 7.22 (dd, J=2.0, 6.5 Hz, 1H), 2.23 (d, J=2.0 Hz, 3H), 1.34 (s, 12H); $^{13}$C NMR (125 MHz, CDCl$_3$) δ 163.9 (d, J=247.5 Hz), 134.2 (d, J=5.7 Hz), 133.4 (d, J=8.5 Hz), 128.4 (d, J=2.9 Hz), 126.6 (d, J=21.9 Hz), 84.1, 24.7, 14.5 (d, J=3.9 Hz); $^{19}$F NMR (470 MHz, CDCl$_3$) δ 109.9; $^{11}$B NMR (160 MHz, CDCl$_3$) δ 29.8 (br s).

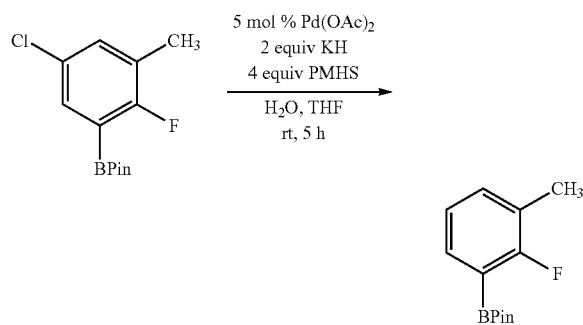

The resulting borylated arene was hydrodehalogenated using the general procedure described above (reaction time of 5 h). The hydrodehalogenation reaction afforded a colorless oil (0.211 g, 89%): $^1$H NMR (500 MHz, CDCl$_3$) δ 7.56 (ddd, J=1.5, 5.0, 7.5 Hz, 1H), 7.29 (ddd, J=1.0, 6.0, 7.0 Hz, 1H), 7.04 (dd, J=7.5, 7.5 Hz, 1H), 2.28 (d, J=2.5 Hz, 3H), 1.37 (s, 12H); $^{13}$C NMR (125 MHz, CDCl$_3$) δ 165.6 (d, J=248.4 Hz), 134.7 (d, J=5.6

Hz), 134.1 (d, J=8.6 Hz), 124.6 (d, J=19.8 Hz), 123.4 (d, J=2.9 Hz), 83.8, 24.8, 14.6; $^{19}$F NMR (470 MHz, CDCl$_3$) δ 106.9; $^{11}$B NMR (160 MHz, CDCl$_3$) δ 30.4 (br s).

Tandem Borylation/Dehalogenation of 1-chloro-4-fluoro-2-methylbenzene

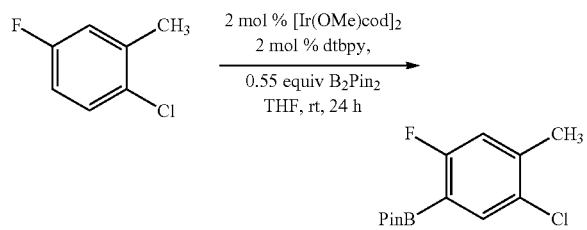

1-Chloro-4-fluoro-2-methylbenzene was borylated using the general procedure described above. After workup, a white solid was obtained (2.38 g, 88%): mp 48-49° C.; $^1$H NMR (500 MHz, CDCl$_3$) δ 7.66 (d, J=5.5 Hz, 1H), 6.91 (d, J=9.5 Hz, 1H), 2.35 (s, 3H), 1.34 (s, 12H); $^{13}$C NMR (125 MHz, CDCl$_3$) δ 165.4 (d, J=249.4 Hz), 141.7 (d, J=9.5 Hz), 136.5 (d, J=8.5 Hz), 129.1 (d, J=2.9 Hz), 117.7 (d, J=25.6 Hz), 84.1, 24.7, 20.4 (d, J=1.9 Hz); $^{19}$F NMR (470 MHz, CDCl$_3$) δ 106.5; $^{11}$B NMR (160 MHz, CDCl$_3$) δ 29.8 (br s).

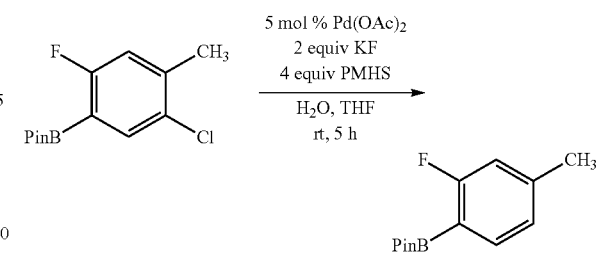

The resulting borylated arene was hydrodehalogenated using the general procedure described above (reaction time of 5 h). The hydrodehalogenation reaction afforded a white solid (0.189 g, 80%): mp 58-60° C.; $^1$H NMR (500 MHz, CDCl$_3$) δ 7.63 (dd, J=7.0, 7.5 Hz, 1H), 6.96 (d, J=7.5 Hz, 1H), 6.86 (d, J=10.5 Hz, 1H), 2.37 (s. 3H), 1.37 (s, 12H); $^{13}$C NMR (125 MHz, CDCl$_3$) δ 167.3 (d, J=249.4 Hz), 144.4 (d, J=8.5 Hz), 136.6 (d, J=8.6

Hz), 124.5 (d, J=2.9 Hz), 115.8 (d, J=23.7 Hz), 83.7, 24.8, 21.5; $^{19}$F NMR (470 MHz, CDCl$_3$) δ 103.8; $^{11}$B NMR (160 MHz, CDCl$_3$) δ 30.3 (br s).

Tandem Borylation/Dehalogenation of 4-bronco-1,2-difluorobenzene

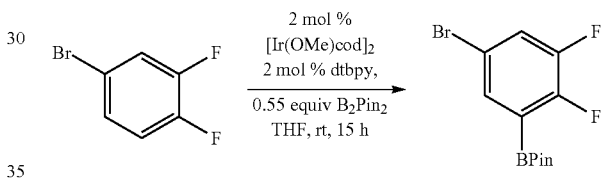

4-Bromo-1,2-difluorobenzene was borylated using the general procedure described above. After workup, a white solid was obtained (0.274 g, 86%): mp 41-42° C.; $^1$H NMR (500 MHz, CDCl$_3$) δ 7.57 (ddd, J=2.0, 4.0, 5.0 Hz, 1H), 7.37 (ddd, J=2.5, 7.0, 9.0 Hz, 1H), 1.34 (s, 12H); $^{13}$C NMR (125 MHz, CDCl$_3$) δ 153.7 (dd, J=11.4, 252.2 Hz), 150.3 (dd, J=16.1, 253.2 Hz), 133.7 (dd, J=4.0, 7.0 Hz), 123.4 (d, J=20.0 Hz), 115.6 (dd, J=4.0, 7.0 Hz), 84.6, 24.7; $^{19}$F NMR (470 MHz, CDCl$_3$) δ 130.0, 134.9; $^{11}$B NMR (160 MHz, CDCl$_3$) δ 29.3 (br s).

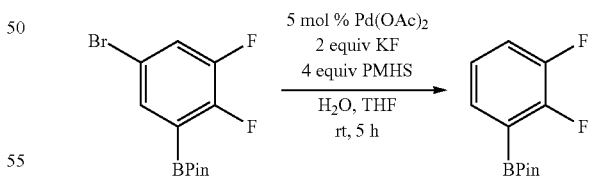

The resulting borylated arene was hydrodehalogenated using the general procedure described above (reaction time of 5 h). The hydrodehalogenation reaction afforded a colorless oil (0.151 g, 63%): $^1$H NMR (500 MHz, CDCl$_3$) δ 7.45 (m, 1H), 7.23 (m, 1H), 7.06 (m, 1H), 1.36 (s, 12H); $^{13}$C NMR (125 MHz, CDCl$_3$) δ 154.6 (dd, J=11.5, 251.5 Hz), 150.5 (dd, J=14.3, 247.6 Hz), 131.1 (dd, J=3.7, 6.6 Hz), 124.1 (dd, J=3.9, 5.7 Hz), 120.2 (d, J=17.1 Hz), 84.2, 24.8; $^{19}$F NMR (470 MHz, CDCl$_3$) δ 129.1, 139.1; $^{11}$B NMR (160 MHz, CDCl$_3$) δ 29.8 (br s).

One Pot Borylation/Dehalogenation of 1-bromo-4-fluoro-2-methoxybenzene

A one pot borylation/dehalogenation methodology was also investigated. The scheme below illustrates the one borylation/dehalogenation methodology which was investigated.

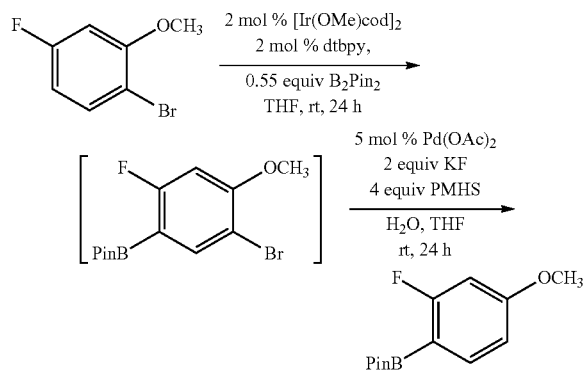

1-Bromo-4-fluoro-2-methoxybenzene was borylated using the general procedure described above. The borylation reaction was complete after 24 h, as judged by NMR spectroscopy. The reaction vessel was transferred into a nitrogen atmosphere glovebox, and the reaction solution transferred to an oven-dried round bottom flask. The flask was sealed using a rubber septum and removed from the glovebox.

The crude reaction mixture was subjected to the general hydrodehalogenation procedure described above (reaction time 24 h). The reaction mixture was diluted with Et$_2$O and the layers were separated. The ether layer was filtered through a plug of silica gel. The silica gel was flushed with hexane (2×10 mL) and with a hexane/EtOAc mixture (10 mL). The eluted solution was concentrated by rotary evaporation. The resulting solution was filtered through another plug of silica gel. The plug was flushed with hexane (4×10 mL) to remove the final traces of boron and Pd byproducts. The volatiles were removed by rotary evaporation to afford a light orange color oil (0.1597 g, 63%): $^1$H NMR (500 MHz, CDCl$_3$) δ 7.66 (dd, J=7.5, 7.5 Hz, 1H), 6.70 (dd, J=2.5, 8.0 Hz, 1H), 6.58 (dd, J=2.5, 11.5 Hz, 1H), 3.82 (s, 3H), 1.36 (s, 12H); $^{13}$C NMR (125 MHz, CDCl$_3$) δ 168.6 (d, J=249.4 Hz), 163.9 (d, J=11.4 Hz), 137.7 (d, J=10.4 Hz), 109.9 (d, J=2.9 Hz), 101.1 (d, J=27.5 Hz), 83.6, 55.4, 24.8; $^{19}$F NMR (470 MHz, CDCl$_3$) δ 100.4; $^{11}$B NMR (160 MHz, CDCl$_3$) δ 29.9 (br s).

Example 4

Borylation of Pyridines

General Procedure for the Borylation of Pyridines

The iridium-catalyzed borylation of substituted pyridines was investigated. An oven-dried 3 mL screw-cap Wheaton® vial was charged inside a nitrogen-filled glovebox with [Ir(OMe)cod]$_2$ (3.3 mg, 0.005 mmol) and dtbpy (2.7 mg, 0.01 mmol). THF (1.0-1.5 mL) was added, followed by B$_2$pin$_2$ (127 mg, 0.5 mmol) and the pyridine substrate (0.5 or 1.0 mmol). The vial was capped and heated outside the glovebox at 80° C. for 18-22 hours. An aliquot was then taken for GC and/or NMR analysis. Isolation of products was performed by flash column chromatography.

Borylation of 2,6-Dichloropyridine

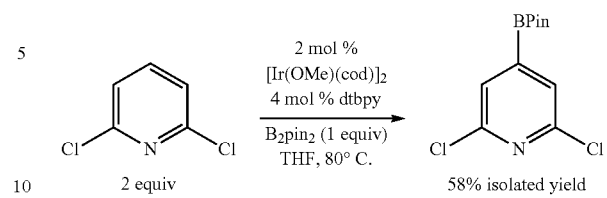

An oven-dried 3 mL screw-cap Wheaton® vial was charged inside a nitrogen-filled glovebox with [Ir(OMe)cod]$_2$ (3.3 mg, 0.005 mmol) and dtbpy (2.7 mg, 0.01 mmol). THF (1.5 mL) was added, followed by B$_2$pin$_2$ (127 mg, 0.5 mmol) and 2,6-dichloropyridine (147 mg, 1.0 mmol). The vial was capped and heated outside of the glovebox at 80° C. for 19 h. The reaction solvent was removed on a rotary evaporator, and the residue was purified by flash column chromatography using hexanes-EtOAc mixtures as eluent providing 2,6-dichloro-4-(4,4,5,5-tetramethyl-1,3,2-dioxaborolan-2-yl)pyridine as a white solid (160 mg, 58%): $^1$H NMR (300 MHz, CDCl$_3$) δ 7.57 (s, 1H), 1.33 (s, 12H).

Borylation of 2-Methoxypyridine

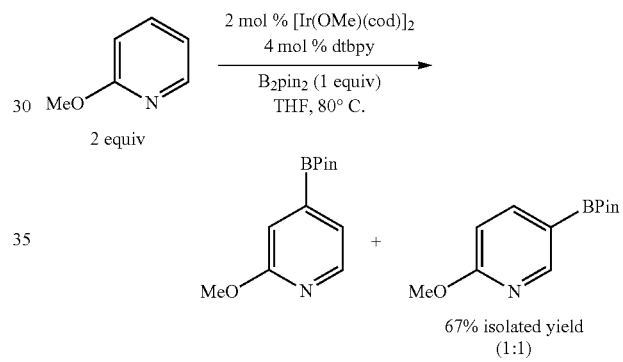

An oven-dried 3 mL screw-cap Wheaton® vial was charged inside a nitrogen-filled glovebox with [Ir(OMe)cod]$_2$ (3.3 mg, 0.005 mmol) and dtbpy (2.7 mg, 0.01 mmol). THF (1.5 mL) was added, followed B$_2$pin$_2$ (127 mg, 0.5 mmol) and 2-methoxypyridine (105 μL, 1.0 mmol). The vial was capped and heated outside of the glovebox at 80° C. for 19 h. The reaction solvent was removed on a rotary evaporator, and the residue was purified by flash column chromatography using hexanes-EtOAc mixtures as eluent providing a 1:1.4 mixture of 4- and 5-Bpin isomers, 2-methoxy-4-(4,4,5,5-tetramethyl-1,3,2-dioxaborolan-2-yl)pyridine and 2-methoxy-5-(4,4,5,5-tetramethyl-1,3,2-dioxaborolan-2-yl) pyridine, as a colorless oil (153 mg, 67%): $^1$H NMR (300 MHz, CDCl$_3$) δ 8.55 (s, 1H, H$_d$), 8.18 (d, J=5.1 Hz, 1H, H$_a$), 7.95 (dd, J=8.4, 1.8 Hz, 1H, H$_e$), 7.25-7.12 (m, 2H, H$_b$ and H$_c$), 6.73 (d, 8.4 Hz, 1H, H$_f$), 3.99 (s, 3H, 5-Bpin isomer), 3.96 (s, 3H, 4-Bpin isomer), 1.32 (s, 12H, 4-Bpin isomer), 1.31 (s, 12H, 5-Bpin isomer).

Borylation of 2-Fluoro-6-Methylpyridine

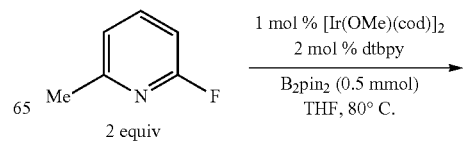

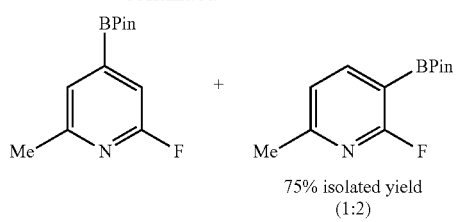

75% isolated yield
(1:2)

An oven-dried 3 mL screw-cap Wheaton® vial was charged inside a nitrogen-filled glovebox with [Ir(OMe)cod]$_2$ (3.3 mg, 0.005 mmol) and dtbpy (2.7 mg, 0.01 mmol). THF (1.5 mL) was added, followed by B$_2$pin$_2$ (127 mg, 0.5 mmol) and 2-fluoro-6-methylpyridine (103 μL, 1.0 mmol). The vial was capped and heated outside of the glovebox at 80° C. for 18 h. $^{19}$F NMR analysis of the crude reaction mixture showed 78% conversion of starting material and formation of a 1:1.8 ratio of 3-Bpin:4-Bpin compounds. The reaction solvent was removed on a rotary evaporator, and the residue was purified by flash column chromatography using pentane-EtOAc mixtures as eluent providing a 1:3 mixture of 3- and 4-Bpin isomers, 2-fluoro-6-methyl-3-(4,4,5,5-tetramethyl-1,3,2-dioxaborolan-2-yl)pyridine and 2-fluoro-6-methyl-4-(4,4,5,5-tetramethyl-1,3,2-dioxaborolan-2-yl)pyridine, as a colorless oil (177 mg 75%): $^{1}$H NMR (500 MHz, CDCl$_3$) δ 8.04 (dd, J=8.1, 7.8 Hz, 1H, H$_a$), 7.36 (d, J=2.3 Hz, 1H, H$_e$), 7.07-7.06 (s, 1H, H$_d$), 7.02 (dd, J=7.8, 2.2 Hz, 1H, H$_b$), 2.50 (s, 3H, 3-Bpin isomer), 2.49 (s, 3H, 4-Bpin isomer), 1.34 (s, 12H, both isomers); $^{19}$F NMR (470 MHz, CDCl$_3$) δ −58.43 (d, J=8.1 Hz, 3-Bpin isomer), −69.80 (4-Bpin isomer).

Borylation of 4-Amino-2-methylpyridine

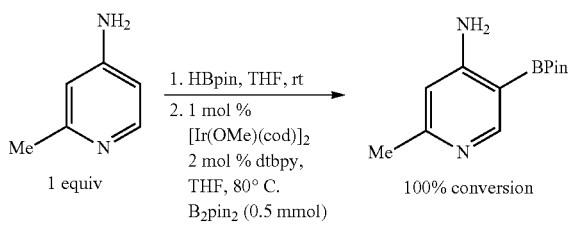

An oven-dried 3 mL screw-cap Wheaton® vial was charged inside a nitrogen-filled glovebox with 4-amino-2-methylpyridine (54 mg, 0.5 mmol), followed by THF (1.0 mL) and HBpin (73 μL, 0.5 mmol). Slow gas evolution and formation of white precipitates were observed. The reaction mixture was stirred for 30 min. [Ir(OMe)cod]$_2$ (3.3 mg, 0.005 mmol), dtbpy (2.7 mg, 0.01 mmol), and B$_2$pin$_2$ (127 mg, 0.5 mmol) were added. The test tube was rinsed with THF (0.5 mL), and the solution was added to the mixture. The vial was capped and heated outside of the glovebox at 80° C. for 22 h. Methyl alcohol (MeOH; 3 mL) was added slowly dropwise to the reaction mixture, and resulting solution was stirred for 3 h at rt. The solvent was removed by rotary evaporation, and analysis by GC and $^1$H NMR spectroscopy showed full conversion of starting material to 4-amino-2-methyl-5-(4,4,5,5-tetramethyl-1,3,2-dioxaborolan-2-yl)pyridine.

Borylation of 2-chloro-4-trifluoromethylpyridine

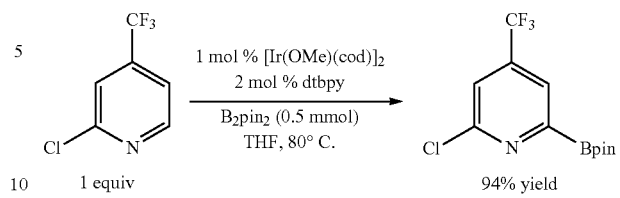

An oven-dried 3 mL screw-cap Wheaton® vial was charged inside a nitrogen-filled glovebox with [Ir(OMe)cod]$_2$ (3.3 mg, 0.005 mmol) and dtbpy (2.7 mg, 0.01 mmol). THE (1.0 mL) was added followed by B$_2$pin$_2$ (127 mg, 0.5 mmol) and 2-chloro-4-trifluoromethylpyridine (64 μL, 0.5 mmol). The vial was capped and heated outside of the glovebox at 80° C. for 18 h. The reaction solvent was removed by rotary evaporation. The residue was purified by flash column chromatography using pentane-EtOAc mixtures as eluent to provide 2-chloro-6-(4,4,5,5-tetramethyl-1,3,2-dioxaborolan-2-yl)-4-trifluoromethylpyridine as a colorless oil that solidified over time (145 mg, 94%): $^1$H NMR (500 MHz, CDCl$_3$) δ 7.96 (s, 1H), 7.59 (s, 1H), 1.40 (s, 12H); $^{19}$F NMR (470 MHz, CDCl$_3$) δ −64.75. The structure was confirmed by subjecting the compound to deuterodeborylation using [Ir(OMe)cod]$_2$ (2 mol %) in methanol-d$_4$ at 80° C.

Borylation of 2-chloro-4-fluoropyridine

An oven-dried 3 mL screw-cap Wheaton® vial was charged inside a nitrogen-filled glovebox with [Ir(OMe)cod]$_2$ (3.3 mg, 0.005 mmol) and dtbpy (2.7 mg, 0.01 mmol). THF (1.5 mL) was added, followed by B$_2$pin$_2$ (127 mg, 0.5 mmol) and 2-chloro-4-fluoropyridine (90 μL, 1.0 mmol). The vial was capped and heated outside of the glovebox at 80° C. for 20 h. The reaction solvent was removed by rotary evaporation. The residue was purified by flash column chromatography using pentane-EtOAc mixtures as eluent to provide 2-chloro-4-fluoro-5-(4,4,5,5-tetramethyl-1,3,2-dioxaborolan-2-yl)pyridine as a colorless oil (165 mg, 64%): $^1$H NMR (500 MHz, CDCl$_3$) δ 8.67 (d, J=8.9 Hz, 1H), 7.06 (d, J=8.4 Hz, 1H), 1.36 (s, 12H); $^{19}$F NMR (470 MHz, CDCl$_3$) δ −89.75--89.85 (m). The structure was confirmed by subjecting the compound to deuterodeborylation using [Ir(OMe)cod]$_2$ (2 mol %) in methanol-d$_4$ at 80° C.

Borylation of 2-chloro-3-fluoropyridine

An oven-dried 3 mL screw-cap Wheaton® vial was charged inside a nitrogen-filled glovebox with [Ir(OMe)cod]$_2$ (3.3 mg, 0.005 mmol) and dtbpy (2.7 mg, 0.01 mmol). THF (1.0 mL) was added, followed by B$_2$pin$_2$ (127 mg, 0.5 mmol) and 2-chloro-3-fluoropyridine (66 mg, 0.5 mmol). The vial was capped and heated outside of the glovebox at 80° C. for 18 h. $^{19}$F NMR analysis of the crude reaction mixture showed full conversion of starting material and formation of a 3.6:2.0:1.0 ratio of 4-Bpin:5-Bpin:4,6-diBpin compounds. The reaction solvent was removed by rotary evaporation. The residue was purified by flash column chromatography using pentane-EtOAc mixtures as eluent to provide a 1:1 mixture (by $^{19}$F NMR) of 4- and 5-Bpin isomers, 2-chloro-3-fluoro-4-(4,4,5,5-tetramethyl-1,3,2-dioxaborolan-2-yl)pyridine and 2-chloro-3-fluoro-5-(4,4,5,5- tetramethyl-1,3,2-dioxaborolan-2-yl)pyridine, as a colorless oil (82 mg, 32%): $^1$H NMR (500 MHz, CDCl$_3$) δ 8.52 (s, 1H, H$_e$), 8.22 (d, J=4.4 Hz, 1H, H$_a$), 7.81 (dd, J=8.3, 1.4 Hz, 1H, HO, 7.54 (dd, J=4.4, 4.4 Hz, 1H, H$_b$), 1.38 (s, 12H, 4-Bpin or 5-Bpin isomer), 1.36 (s, 12H, 4-Bpin or 5-Bpin isomer); $^{19}$F NMR (470 MHz, CDCl$_3$) δ −109.38 (4-Bpin isomer), −120.30 (d, J=8.3 Hz, 5-Bpin isomer).

Borylation of 3-Bromo-5-fluoropyridine

An oven-dried 3 mL screw-cap Wheaton® vial was charged inside a nitrogen-filled glovebox with [Ir(OMe)cod]$_2$ (3.3 mg, 0.005 mmol) and dtbpy (2.7 mg, 0.01 mmol). THF (1.0 mL) was added followed by B$_2$pin$_2$ (127 mg, 0.5 mmol) and 3-bromo-5-fluoropyridine (88 mg, 0.5 mmol). The vial was capped and heated outside of the glovebox at 80° C. for 22 h. 16% conversion was detected by $^{19}$F NMR spectroscopy from the crude reaction mixture.

Example 5

Directed C—H Activation Borylation Using Monodentate Pyridine Ligands

Monodentate pyridines were investigated as potential ligands in the borylation of arenes, including arenes substituted by a directing group. Pyridines were selected for evaluation based on the proposed intermediates in borylation reactions of arenes. During non-directed borylation in the presence of an iridium catalyst and a bidentate ligand, the metal center is coordinated by the bidentate pyridine ligand, thus leaving one open coordination site for the substrate to bind and undergo the C—H activation step. If a monodentate ligand, such as a pyridine ligand is used, an additional free coordination site is available on the metal center. As shown below, if a substrate possesses a group that is able to bind to the metal center, activation of the C—H bond ortho to this group can occur.

Chelate Directed

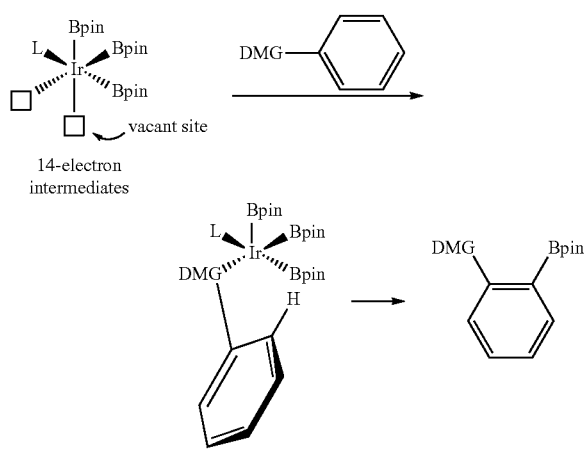

It was hypothesized that appropriately suitable monopyridine ligands might favor 14-electron intermediates 3 over 4 in the scheme below, and thus allow for directed borylation. In particular, pyridines that are electron-poor or sterically hindered were considered to be likely candidates

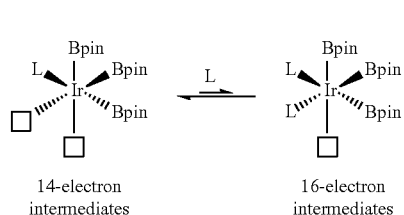

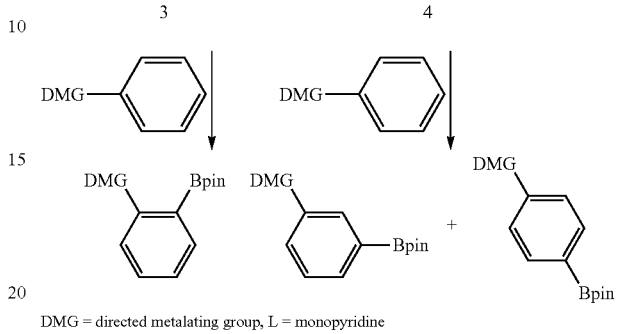

DMG = directed metalating group, L = monopyridine

First, pyridine ligands were evaluated on carbonyl containing substrates. Acetophenone was chosen as model substrate. Screening pyridine ligands for borylation of acetophenone was done using 1 mol % [Ir(OMe)cod]$_2$, 2 mol % pyridine ligand, 1 equivalent (equiv) of B$_2$pin$_2$, and 2 equiv of ketone in THF at 80° C. (Table 3).

TABLE 3

Screening of Pyridyl Ligands Using Acetophenone as a Model Substrate.

| Entry | Ligand | o/(m + p) | Total Conversion | Borylated Products |
|---|---|---|---|---|
| 1 | 3,5-diCF$_3$Py | 124:1 | 78% | 40% |
| 2 | 2-CF$_3$Py | 19:1 | 21% | 21% |
| 3 | 4-CF$_3$Py | 16.6:1 | 56% | 48% |
| 4 | 2-FPy | 17:1 | 34% | 24% |
| 5 | 2-MeOPy | 9.6:1 | 46% | 22% |
| 6 | 2-F-6-MeOPy | 96:1 | 71% | 52% |
| 7 | 2-Cl-6-MeOPy | ortho | 55% | 45% |
| 8 | 2-F-6-MePy | ortho | 23% | 23% |

The position of substituents on the pyridine ring played a significant role in the reaction outcome. The best ligand, affording both good conversion and excellent regioselectivity, was 3,5-di(trifluoromethyl)pyridine (Table 3, entry 1). Unfortunately, the cost of this pyridine ligand is high ~$49 per 250 mg. Borylation reactions suffered from the formation of an aldol condensation side product. Putting a CF$_3$ group at the 2-position of the pyridine slowed down the reaction and decreased regioselectivity (compare Table 3, entries 1 and 2). However, placing a CF$_3$ group at the 4-position improved conversion, and the regioselectivity was moderate (compare Table 3, entries 2 and 3). Smaller substituents, such as fluorine or methoxy, in the 2-position provided better conversions in comparison with —CF$_3$ groups; however, selectivity was significantly lower. Interestingly, placing substituents at the 2- and 6-position of the pyridine greatly enhanced regioselectivity. Conversions were influenced by the steric bulk of the substituents (compare Table 3, entries 6, 7, and 8). Excess of boron reagent dramatically improved reaction outcome. No aldol condensation product was detected and only the ortho borylated product was observed.

Next, preliminary scope studies were performed on ketones. Various alkyl and aryl ketones were successfully borylated. The iridium-catalyzed borylation of cyclopropyl phenyl ketone, performed using 2-methoxypyridine as the supporting ligand, afforded the ortho-borylated product in 50% yield. Borylation of 3,5-difluoroacetophenone proceeded smoothly with 4-trifluoropyridine being employed as ligand. The conversion of 47% was detected by GC with 16:1 ratio of ortho:para borylated products. The yields have not been optimized and it should be noted that if dtbpy would be used as a ligand, borylation occurred at 4-position in between fluorine substituents.

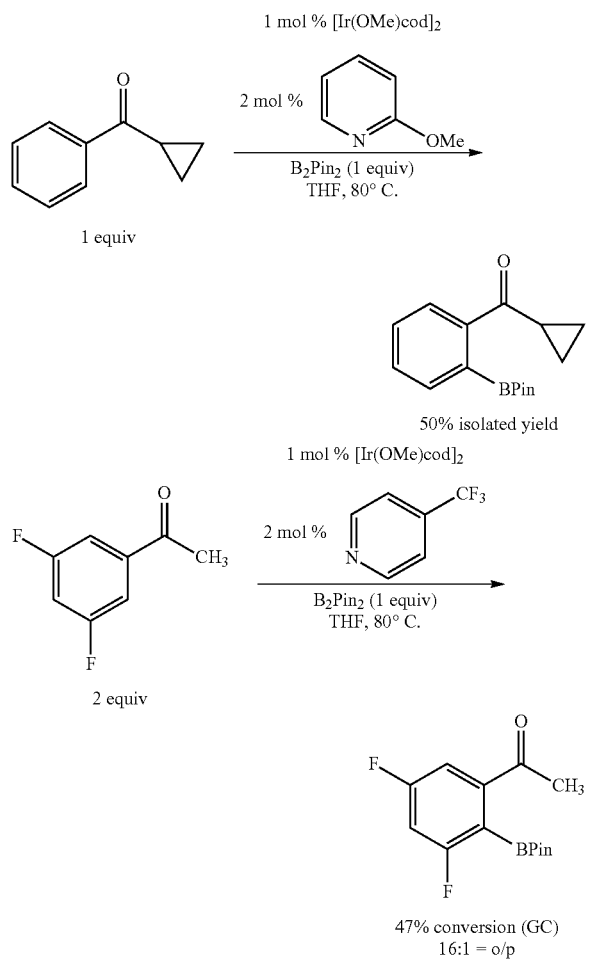

Ligand optimization studies were performed using other carbonyl-containing substrates. Methyl benzoate gave acceptable ortho selectivity (o/(m+p)=11.7:1) and good conversion when 3,5-di(trifluoromethyl)pyridine was used as ligand. The 2-CF$_3$ and 4-CF$_3$ substituted pyridines provided poor regioselectivity. Interestingly, very good ortho selectivity (o/(m+p)=10.4:1) was obtained when 2-methoxypyridine was employed. The price of 2-methoxypyridine in Aldrich is $29.70 per 25 grams, which makes it a very attractive choice as a ligand. In comparison, when the bidentate ligand dtbpy was used, methyl benzoate was exclusively borylated at the meta- and para-positions and no ortho borylated product was detected. Moreover, N,N-dimethylbenzamide provided good conversion and excellent ortho selectivity when 2-methoxypyridine was used as supporting ligand. Other monodentate pyridine ligands failed to initiate borylation of benzamide or poor conversions were obtained. These results suggest distinct differences in reaction outcomes when certain bidentate and monodentate pyridine ligands are employed.

It was hypothesized that monodentate pyridine ligands might also improve selectivities for borylation ortho to fluorine when directing groups are not present. To evaluate this hypothesis, the borylation of 3-fluorotoluene with 2-methoxypyridine was examined and compared to borylations performed using 2-(aminomethyl)pyridine and dtbpy. As shown in Table 4, superior results were obtained with 2-methoxypyridine as ligand. The ratio of isomers was improved to 4.7:1 in favor of borylation ortho to fluorine substituent. In comparison, when bidentate dtbpy was employed as ligand a 1:1 ratio of isomers was detected.

TABLE 4

Borylation of 3-Fluorotoluene.

| Entry | Ligand | 5:6 | Conversion |
|---|---|---|---|
| 1 | 2-(NH$_2$CH$_2$)Py | 2.5:1 | 24% |
| 2$^a$ | 2-MeOPy | 4.7:1 | 69% |
| 3 | dtbpy | 1:1 | 86% |

$^a$3-fluorotoluene:B$_2$pin$_2$ = 1:1, THF, 80° C.

This set of ligands was also explored in borylation of 1-chloro-2,3-difluorobenzene. Use of 2-(aminomethyl)pyridine as ligand gave good conversion and good selectivity favoring borylation ortho to the fluorine substituent (Table 5). Changing the solvent from THF to hexane slightly improved the selectivity when the same ligand was employed. The ligand is commercially available (Aldrich, $60.9 per 25 grams). Furthermore, 3.3:1 ratio of borylated products was detected when 2-methoxypyridine ligand was used. Other mono- and diborylated products were observed and total conversion of the substrate was 85% as determined by $^{19}$F NMR analysis. Interestingly, both ligands are superior to the btfbpy bipyridine ligand, which gave a 2.5:1 ratio of borylated products in THF (Table 5). This bipyridine ligand is not commercially available; however it can be prepared in a one step synthesis from 2-chloro-4-(trifluoromethyl)pyridine (Oakwood Chemical, $110 per 25 grams).

TABLE 5

Borylation of 1-Chloro-2,3-difluorobenzene.

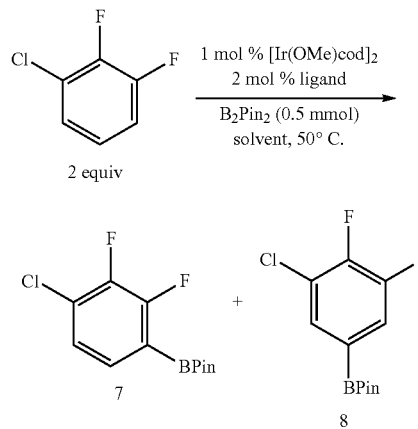

TABLE 5-continued

| Entry | Ligand | Solvent | 7:8 | Conversion |
|---|---|---|---|---|
| 1 | 2-($NH_2CH_2$)Py | THF | 2.6:1 | 44% ($^{19}$F NMR) |
| 2 | 2-($NH_2CH_2$)Py | Hex | 3.0:1 | 60% (GC) |
| 3[a] | 2-MeOPy | THF | 3.3:1 | 85% (total conv $^{19}$F NMR) |
| 3[a] | btfbpy | THF | 2.5:1 | 97% (total conv $^{19}$F NMR) |

[a]1-chloro-2,3-difluorobenzene:$B_2pin_2$ = 1:1, 80° C.

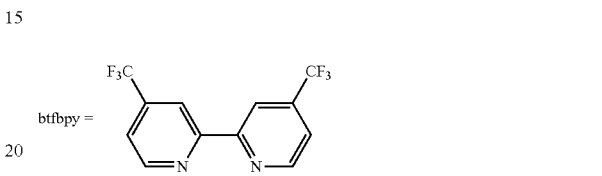

Importantly, as summarized in the schemes below, these methods complement other borylation methods utilizing alternative ligands,

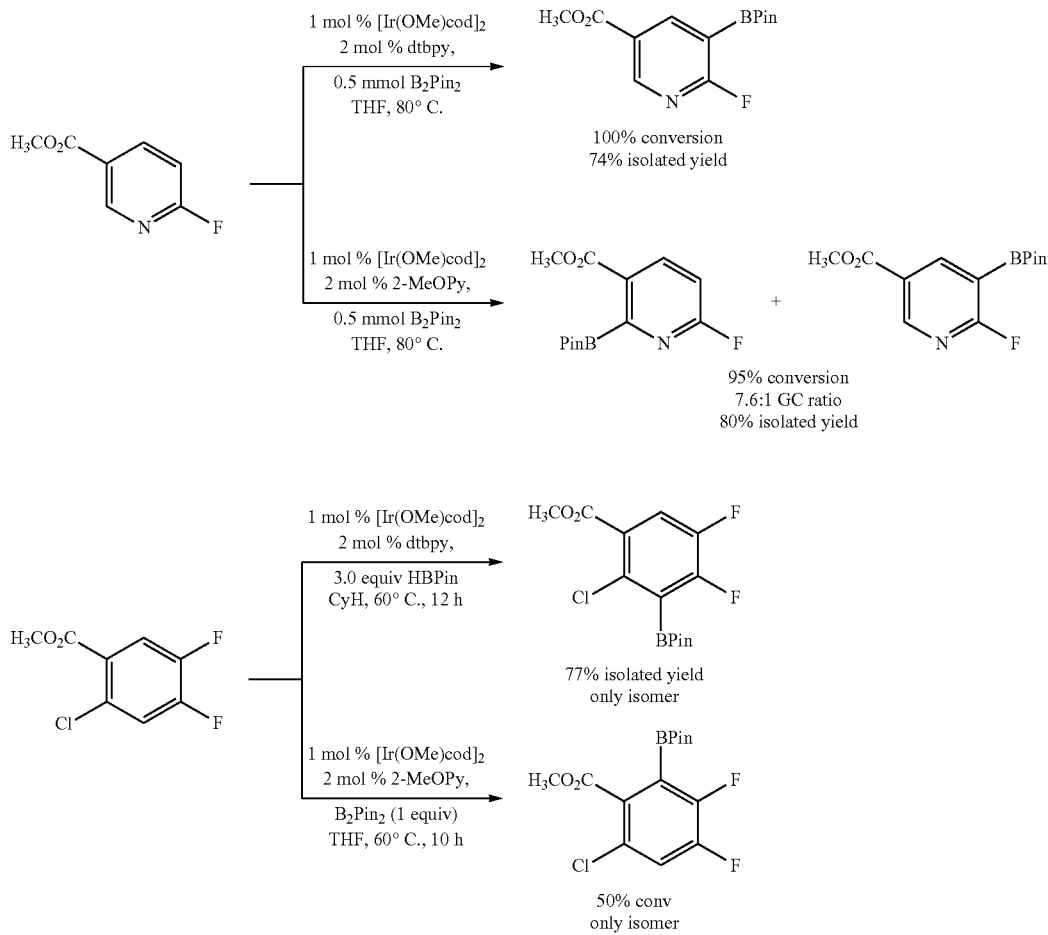

Experimental Methods

General Procedure for the Borylation of Acetophenone

In a nitrogen-filled glovebox, 3 mL Wheaton® vials were charged with [Ir(OMe)cod]$_2$ (3.3 mg, 0.005 mmol, 1 mol %), and B$_2$pin$_2$ (127 mg, 0.5 mmol) followed by THF (1.5 mL). To the resulting solutions acetophenone (116 µL, 1.0 mmol) and pyridine ligand (0.01 mmol, 2 mol %) were added. The vials were capped and removed from the glovebox. The reaction mixtures were heated at 80° C. for 15 h. The reaction mixtures were cooled to rt, opened to the air, and samples were taken for GC analysis. The results are presented in Table 3 above. Total conversion corresponds to total conversion of acetophenone.

General Procedure for Ligand Studies in Borylation of 3-Fluorotoluene

In a nitrogen-filled glovebox, a 3 mL Wheaton® vial was charged with [Ir(OMe)cod]$_2$ (3.3 mg, 0.005 mmol, 1 mol %), B$_2$pin$_2$ (127 mg, 0.5 mmol), and dtbpy (2.7 mg, 0.01 mmol, 2 mol %), followed by hexane (1.5 mL). In the case of 2-(aminomethyl)pyridine (1.0 µL, 0.01 mmol, 2 mol %), it was added last. To the resulting solutions, 3-fluorotoluene (111 µL, 1.0 mmol) was added. The vials were capped and removed from the glovebox. The reaction mixtures were heated at 70° C. for 15 h. The reaction mixtures were cooled to rt, opened to the air, and samples were taken for GC analysis. The results are presented in Table 4 above.

An alternate procedure was employed when using 2-methoxypyridine as the ligand. In a nitrogen-filled glovebox, a 3 mL Wheaton® vial was charged with [Ir(OMe)cod]$_2$ (6.6 mg, 0.01 mmol, 1 mol %) and B$_2$pin$_2$ (254 mg, 1.0 mmol), followed THF (1.5 mL). To the resulting solution 3-fluorotoluene (111 µL, 1.0 mmol) was added followed by 2-methoxypyridine (2.1 µL, 0.02 mmol, 2 mol %). The vial was capped and removed from the glovebox. The reaction mixture was heated at 80° C. for 24 h. The reaction mixture was cooled to rt, opened to the air, and a sample was taken for NMR analysis.

General Procedure the Borylation of 1-Chloro-2,3-difluorobenzene

In a nitrogen-filled glovebox, a 3 mL Wheaton® vial was charged with [Ir(OMe)cod]$_2$ (3.3 mg, 0.005 mmol, 1 mol %) and B$_2$pin$_2$ (127 mg, 0.5 mmol). 1-Chloro-2,3-difluorobenzene (148 mg, 1.0 mmol) was weighed into a test tube and transferred to the reaction vials with the appropriate solvent (1.5 mL). 2-(Aminomethyl)pyridine (1.0 µL, 0.01 mmol, 2 mol %) was then added to reaction mixture. The vials were capped and removed from the glovebox. The reaction mixtures were heated at 50° C. for 16 h. The reaction mixtures were cooled to rt, opened to the air, and samples were taken for GC and NMR analysis. The results are presented in Table 5 above.

Borylation of Cyclopropyl Phenyl Ketone

In a nitrogen-filled glovebox, a 3 mL Wheaton® vial was charged with [Ir(OMe)cod]$_2$ (6.6 mg, 0.01 mmol, 1 mol %), and B$_2$pin$_2$ (254 mg, 1.0 mmol), followed by THF (1.5 mL). To the resulting solution cyclopropyl phenyl ketone (138 µL, 1.0 mmol) and 2-methoxypyridine (2.1 µL, 0.01 mmol, 2 mol %) were added. The vial was capped and removed from the glovebox. The reaction mixtures were heated at 80° C. for 16 h. The solvent was concentrated by rotary evaporation, and the oily residue was purified by flash chromatography using EtOAc-pentane as eluent. Cyclopropyl(2-(4,4,5,5-tetramethyl-1,3,2-dioxaborolan-2-yl)phenyl)ketone was obtained as white solid (53%): $^1$H NMR (500 MHz, CDCl$_3$) δ 7.97 (d, J=7.6 Hz, 1H), 7.54-7.50 (m, 2H), 7.47-7.42 (m, 1H), 2.67-2.61 (m, 1H), 1.40 (s, 12H), 1.31-1.27 (m, 2H), 1.09-1.04 (m, 2H); $^{13}$C NMR (125 MHz, CDCl$_3$) δ 202.4, 141.9, 132.5, 132.2, 129.0, 127.6, 83.8, 25.1, 16.7, 12.4; $^{11}$B NMR (160 MHz, CDCl$_3$) δ 30.8.

Borylation of 3',5'-difluoroacetophenone

In a nitrogen-filled glovebox, a 3 mL Wheaton® vial was charged with [Ir(OMe)cod]$_2$ (3.3 mg, 0.005 mmol, 1 mol %), and B$_2$pin$_2$ (127 mg, 0.5 mmol), followed by THF (1.5 mL). To the resulting solution 3',5'-difluoroacetophenone (156 mg, 1.0 mmol) and 4-trifluoromethylpyridine (1.1 µL, 0.01 mmol, 2 mol %) were added. The vial was capped and removed from the glovebox. The reaction mixture was heated at 80° C. for 19 h. The solvent was concentrated by rotary evaporation, and the oily residue was purified by flash chromatography using Et$_2$O-pentane mixtures as eluent. Recrystallization from pentane gave 1-acetyl-3,5-difluoro-2-(4,4,5,5-tetramethyl-1,3,2-dioxaborolan-2-yl)benzene as white crystals (34%): $^1$H NMR (300 MHz, CDCl$_3$) δ 7.33 (ddd, J=8.4, 2.1, 0.4 Hz, 1H), 6.96 (ddd, J=8.5, 8.0, 2.1 Hz, 1H), 2.56 (s, 3H), 1.42 (s, 12H); $^{19}$F NMR (283 MHz, CDCl$_3$) δ −101.18, −108.04.

Borylation of N,N-dimethylbenzamide

In a nitrogen-filled glovebox, a 3 mL Wheaton® vial was charged with [Ir(OMe)cod]$_2$ (3.3 mg, 0.005 mmol, 0.5 mol %), N,N-dimethylbenzamide (149 mg, 1.0 mmol) and B$_2$pin$_2$ (254 mg, 1.0 mmol), followed THF (1.5 mL). To the resulting solution 2-methoxypyridine (1.1 µL, 0.01 mmol, 1 mol %) was added. The vial was capped and removed from the glovebox. The resulting mixture was heated at 110° C. for 17 h. The reaction mixture was cooled to rt, opened to the air, and a sample was taken for GC and NMR analysis. Conversion to ortho-borylated product was 84%, with only traces of other borylated isomers by GC analysis. Resonances in the $^1$H-NMR spectrum of the reaction mixture match those of ortho-borylated benzamide found in the literature.

Further Ligand Screening Using Methyl Benzoate Borylation

In nitrogen-filled glovebox, 3 mL Wheaton® vials were charged with [Ir(OMe)cod]$_2$ (3.3 mg, 0.005 mmol, 1 mol %) and B$_2$pin$_2$ (127 mg, 0.5 mmol). THF (1.5 mL) was added to the vials, followed by methyl benzoate (124 µL, 1.0 mmol). The appropriate pyridine ligands (0.01 mmol, 2 mol %) were added. When dtbpy was used as a ligand, it was weighed into the vial before addition of solvent. The vials were capped and removed from the glovebox. The reaction mixtures were heated at 80° C. for 18 h. The reaction mixtures were cooled to rt, and samples were taken for GC analysis. The results are presented in Table 6.

TABLE 6

Ligand Screening Using Methyl Benzoate Borylation.

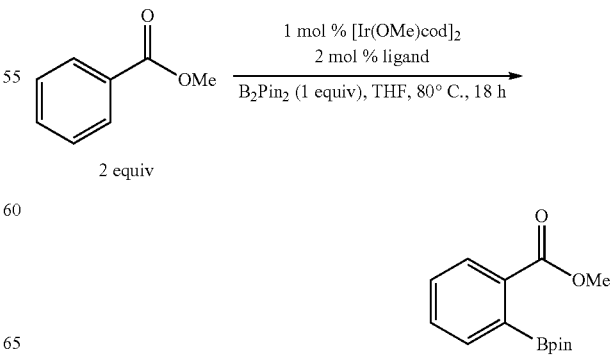

TABLE 6-continued

| Entry | Ligand | o/(m + p) | Conversion |
|---|---|---|---|
| 1 | dtbpy | 0:100 | 78%[a] |
| 2 | 3,5-diCF$_3$Py | 12:1 | 53% |
| 3 | 2-CF$_3$Py | 1.4:1 | 8% |
| 4 | 4-CF$_3$Py | 2.4:1 | 50% |
| 5 | 2-FPy | 2.3:1 | 14% |
| 6 | 2-MePy | 1:1.9 | 24% |
| 7[b] | 2-MeOPy | 10:1 | 81% |

[a]reaction run at 50° C.
[b]methyl benzoate:B$_2$pin$_2$ = 1:1

Example 6

One-Pot Borylation and Hydrodehalogenation Using Pd/C and Ammonium Formate

Tandem borylation/dehalogenation was investigated above as a strategy for the ortho-borylation of arenes that are substituted with an electron-withdrawing group. As discussed above, in the case of arenes that are substituted with an electron-withdrawing group, iridium-catalyzed C—H activation-borylation of the arene is typically governed by steric effects. In the tandem borylation/dehalogenation methods described above, the substrate can include an electron-withdrawing group, and a sacrificial atom (e.g., a halogen such as Cl or Br) positioned para to the electron-withdrawing group, so as to hinder attack of the iridium catalyst at the otherwise sterically favored position meta to the electron-withdrawing group. As a result, iridium-catalyzed C—H activation-borylation of the arene exclusively generates the ortho-borylated (electronic) product. Subsequent dehalogenation can afford exclusively the desired electronic product.

The tandem borylation-hydrodehalogenation methodologies investigated above involved two separate reactions where each product was isolated and carried on to the next step. The hydrodehalogenation process used Pd(OAc)$_2$, polymethylhydrosiloxane (PMHS) and potassium fluoride (KF) as the hydrodehalogenation reagents. This reaction could also be performed in one pot, where the C—H activation borylation reaction was carried out, then the Pd(OAc)$_2$, PMHS and KF were added to carry out the hydrodehalogenation reaction to give the desired product in excellent yields.

An improved one-pot borylation-hydrodehalogenation process was investigated that used palladium on carbon (Pd/C) and ammonium formate as the hydrodehalogenation reagents. This process can be used to prepare otherwise difficult to access borylated molecules The methodology avoids the need for cryogenic conditions to access highly functionalized borylated molecules, which are key intermediates for several high margin agrochemical molecules. The methodology also eliminates potential reactive intermediates that are formed using traditional Li—H exchange reactions to access these borylated molecules.

From a practical standpoint, the one pot methodology eliminates time for isolation, purification of intermediates, and controls waste and solvent usage. Moreover, functional group tolerance in C—H activation and hydrodehalogenation broaden the synthetic utility of this method, potentially allowing access to a broader range of borylated arenes.

Results

A general synthetic methodology for the one-pot borylation-hydrodehalogenation process is included below.

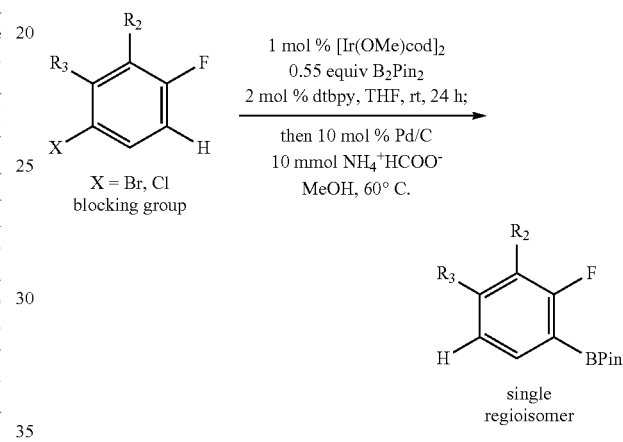

The general borylation procedure detailed in the scheme above was carried out on 1 mmol of starting arene (selected from entries 1-6 in Table 7) and the reaction was complete after 24 h as judged by NMR spectroscopy. The reaction vessel was removed from a nitrogen atmosphere glovebox, and the reaction solution transferred to an oven-dried round bottom flask. The flask was connected to a reflux condenser and purged with nitrogen for 5 min. The general hydrodehalogenation procedure detailed in the scheme above (using Pd/C and ammonium formate) was followed for 24 h at rt. The volatiles were removed by rotary evaporation to afford the reaction products. The reaction products were then characterized by NMR spectroscopy. The results are shown in Table 7 below.

TABLE 7

One-Pot Borylation and Hydrodehalogenation Using Pd/C and Ammonium Formate

| Entry | Starting Arene | Reaction method | Reaction time/temp | Dehalogenation Product (yield[a]) |
|---|---|---|---|---|
| 1 | OMe, F, Br, Bpin (structure) | Two step | 40 min/60° C. | OMe, F, Bpin (structure) 55% |

TABLE 7-continued

One-Pot Borylation and Hydrodehalogenation Using Pd/C and Ammonium Formate

| Entry | Starting Arene | Reaction method | Reaction time/temp | Dehalogenation Product (yield[a]) |
|---|---|---|---|---|
| 2 | 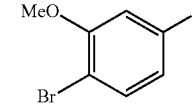 | One-pot | 1 h/60° C. | 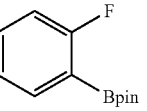 93%[b] |
| 3 | 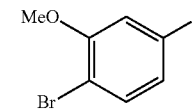 | One-pot | 24 h/rt | 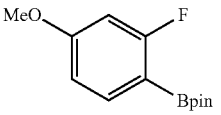 78% |
| 4 | 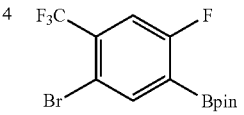 | Two step | 40 min/60 °C. | 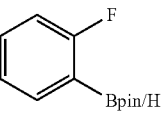 100%[b] (90:10) |
| 5 | 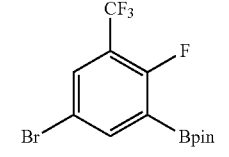 | Two step | 40 min/60° C. | 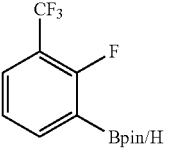 100%[b] (85:15) |
| 6 | 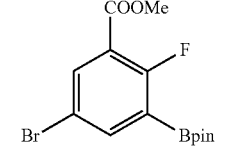 | Two step | 55 min/60° C. | 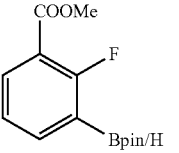 100%[b](87:13) |

[a]Isolated yield;
[b]Conversion

The compositions and methods of the appended claims are not limited in scope by the specific compositions and methods described herein, which are intended as illustrations of a few aspects of the claims. Any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

The term "comprising" and variations thereof as used herein is used synonymously with the term "including" and variations thereof and are open, non-limiting terms.

Although the terms "comprising" and "including" have been used herein to describe various embodiments, the terms "consisting essentially of" and "consisting of" can be used in place of "comprising" and "including" to provide for more specific embodiments of the invention and are also disclosed. Other than where noted, all numbers expressing geometries, dimensions, and so forth used in the specification and claims are to be understood at the very least, and not as an attempt to limit the application of the doctrine of equivalents to the scope of the claims, to be construed in light of the number of significant digits and ordinary rounding approaches.

Unless defined otherwise, all technical and scientific terms used herein have the same meanings as commonly understood by one of skill in the art to which the disclosed invention belongs. Publications cited herein and the materials for which they are cited are specifically incorporated by reference.

What is claimed is:

1. A method of forming a borylated arene comprising:
providing a substrate comprising a substituted arene ring comprising from 1 to 4 substituents, wherein the arene ring is unsubstituted at a first position that is electronically favored for CH-activation and unsubstituted at a second position that is sterically favored for CH-activation; and
contacting the substrate with an iridium precursor complex, an electron deficient bidentate ligand comprising at least one nitrogen heteroatom, and a borylation reagent under conditions effective to form a first borylated arene and optionally a second borylated arene;
wherein the electron deficient bidentate ligand comprises a compound defined by Formula IVa

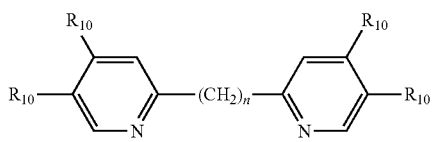

Formula IVa wherein n is 0, 1, 2, or 3 and $R_{10}$ is, independently for each occurrence, hydrogen, a halogen, a nitrile group, a nitro group, a $C_1$-$C_6$ alkyl group, or a $C_1$-$C_6$ perfluoroalkyl group, with the proviso that at least one of $R_{10}$ is chosen from a halogen, a nitrile group, a nitro group, and a $C_1$-$C_6$ perfluoroalkyl group;
wherein the first borylated arene comprises a substituted arene ring comprising from 1 to 4 substituents and a boronic acid or a boronic acid derivative in the first position,
wherein the second borylated arene, when formed, comprises a substituted arene ring comprising from 1 to 4 substituents and a boronic acid or a boronic acid derivative in the second position, and
wherein the molar ratio of the first borylated arene to the second borylated arene is at least 1:1, as determined by GC-FID.

2. The method of claim 1, wherein the arene ring comprising from 1 to 3 substituents.

3. The method of claim 1, wherein the arene ring is substituted with an electron withdrawing group selected from the group consisting of —F and —$CF_3$.

4. The method of claim 1, wherein the substrate comprises a phenyl ring substituted with an electron withdrawing group selected from the group consisting of —F and —$CF_3$, unsubstituted in a position ortho to the electron withdrawing group, and unsubstituted in a position meta to the electron withdrawing group,
wherein the first borylated arene comprises a phenyl ring substituted with an electron withdrawing group selected from the group consisting of —F and —$CF_3$, and a boronic acid or a boronic acid derivative in a position ortho to the electron withdrawing group, and
wherein the second borylated arene, when formed, comprises a phenyl ring substituted with an electron withdrawing group selected from the group consisting of —F and —$CF_3$, and a boronic acid or a boronic acid derivative in a position meta to the electron withdrawing group.

5. The method of claim 1, wherein the substrate comprises a pyridine ring selected from the group consisting of a 2-, 4-disubstituted pyridine ring, a 2-, 6-disubstituted pyridine ring, a 2-, 4-, 6-trisubstituted pyridine ring, and a 2-substituted pyridine ring.

6. The method of claim 1, wherein the substrate comprises a compound defined by Formula I

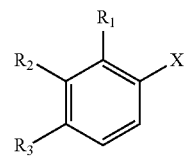

Formula I wherein
X is F or $CF_3$;
$R_1$ is hydrogen, a halogen, —$OR_4$, —$NR_5R_6$, —C(=O)$R_7$, a nitrile group, a $C_1$-$C_6$ alkyl group, or a $C_1$-$C_6$ haloalkyl group;
$R_2$ is hydrogen, a halogen, —$OR_4$, —$NR_5R_6$, —C(=O)$R_7$, a nitrile group, a $C_1$-$C_6$ alkyl group, or a $C_1$-$C_6$ haloalkyl group;
$R_3$ is hydrogen, a halogen, —$OR_4$, —$NR_5R_6$, —C(=O)$R_7$, a nitrile group, a $C_1$-$C_6$ alkyl group, or a $C_1$-$C_6$ haloalkyl group;
$R_4$, $R_5$, and $R_6$ are each, individually for each occurrence, hydrogen or a $C_1$-$C_6$ alkyl group; and
$R_7$ is, individually for each occurrence, hydrogen, —$OR_4$, —$NR_5R_6$, or a $C_1$-$C_6$ alkyl group;
the first borylated arene comprises a compound defined by Formula II

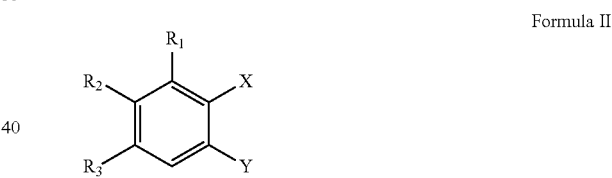

Formula II wherein
X, $R_1$, $R_2$, and $R_3$ are as described above, and Y is a boronic acid or a boronic acid derivative; and
the second borylated arene, when formed, comprises a compound defined by Formula III

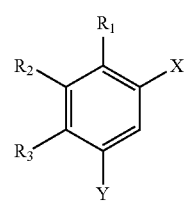

Formula III wherein
X, $R_1$, $R_2$, and $R_3$ are as described above, and Y is a boronic acid or a boronic acid derivative.

7. The method of claim 1, wherein the substrate comprises a 1-chloro-3-fluoro-2-substituted benzene.

8. The method of claim 7, wherein the substrate comprises 1-chloro-3-fluoro-2-methoxybenzene, and wherein the first borylated arene comprises (4-chloro-2-fluoro-3-methoxyphenyl)boronic acid or a (4-chloro-2-fluoro-3-methoxyphenyl)-boronic acid derivative.

9. The method of claim 1, wherein the iridium precursor complex comprises an iridium complex selected from the group consisting of an Ir(I)-cyclooctadiene precursor complex, an Ir(I)-cyclooctene precursor complex, an Ir(I)-mesitylene precursor complex, an Ir(I)-phosphine precursor complex, an Ir(I)-1,2,3,4,5-methylcyclopentadienyl precursor complex, and combinations thereof.

10. The method of claim 1, wherein the substrate, first borylated arene, and second borylated arene, when formed, comprise a substituent selected from the group consisting of —Cl and —Br.

11. The method of claim 10, wherein the substrate comprises a compound defined by the formula below

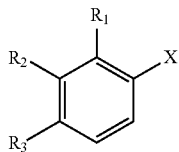

wherein
X is a moiety chosen from an electron withdrawing group or a directed metalating group;
$R_1$ is hydrogen, a halogen, —$OR_4$, —$NR_5R_6$, —C(=O)$R_7$, a nitrile group, a $C_1$-$C_6$ alkyl group, or a $C_1$-$C_6$ haloalkyl group;
$R_2$ is hydrogen, a halogen, —$OR_4$, —$NR_5R_6$, —C(=O)$R_7$, a nitrile group, a $C_1$-$C_6$ alkyl group, or a $C_1$-$C_6$ haloalkyl group;
$R_3$ is —Cl and —Br;
$R_4$, $R_5$, and $R_6$ are each, individually for each occurrence, hydrogen or a $C_1$-$C_6$ alkyl group; and
$R_7$ is, individually for each occurrence, hydrogen, —$OR_4$, —$NR_5R_6$, or a $C_1$-$C_6$ alkyl group;
the first borylated arene comprises a compound defined by formula below

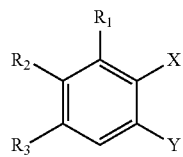

wherein
X, $R_1$, $R_2$, and $R_3$ are as described above, and Y is a boronic acid or a boronic acid derivative; and
the second borylated arene, when formed, comprises a compound defined by the formula below

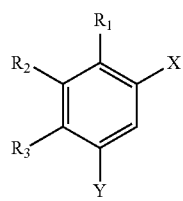

wherein
X, $R_1$, $R_2$, and $R_3$ are as described above, and Y is a boronic acid or a boronic acid derivative
wherein the molar ratio of the first borylated arene to the second borylated arene is at least 25:1, as determined by GC-FID.

12. The method of claim 11, wherein the method further comprises reductively dehalogenating the first borylated arene to obtain a dehalogenated borylated arene.

13. The method of claim 1, further comprising contacting the first borylated arene or the dehalogenated borylated arene with a reactant selected from the group consisting of an aryl halide, an aryl pseudohalide, a vinyl halide, and a vinyl pseudohalide, and a transition metal catalyst to cross-couple the first borylated arene or the dehalogenated borylated arene and the reactant.

* * * * *